(12) United States Patent
Ramesh et al.

(10) Patent No.: US 7,915,293 B2
(45) Date of Patent: Mar. 29, 2011

(54) UBIQUITIN LIGASE INHIBITORS

(75) Inventors: Usha V. Ramesh, Cupertino, CA (US); Gary Charles Look, Santa Clara, CA (US); Rajinder Singh, Belmont, CA (US); Sarkiz D. Issakani, San Jose, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 2066 days.

(21) Appl. No.: 10/858,537

(22) Filed: Jun. 1, 2004

(65) Prior Publication Data

US 2005/0009871 A1    Jan. 13, 2005

Related U.S. Application Data

(60) Provisional application No. 60/475,223, filed on May 30, 2003, provisional application No. 60/509,780, filed on Oct. 9, 2003.

(51) Int. Cl.
*A61K 31/4545* (2006.01)
*C07D 41/02* (2006.01)

(52) U.S. Cl. ........ 514/316; 514/317; 514/326; 546/186; 546/207

(58) Field of Classification Search .................... 564/84; 514/741, 331, 316, 317, 326; 546/246, 186, 546/207
See application file for complete search history.

(56) References Cited

FOREIGN PATENT DOCUMENTS

| WO | WO 98/05315 | 2/1998 |
|---|---|---|
| WO | WO 98/45259 | 10/1998 |
| WO | WO 2004005278 | * 11/2004 |

OTHER PUBLICATIONS

Hcaplus 111:146282.*
Hcaplus 111:146282, "Inhibition of carbonic anhyrase by substituted benzensulfonamides. A reinvestigation by QSAR and molecular graphics analysis", Carotti et. al., 1989.*
Hcaplus 1931:16457, "Diphenyl ether series. II. Preparation and structure of some sulfonic acids and related derivatives", 1931, Suter, C. M.*
Theodora W. Greene, Protective Groups in Organic Synthesis, Third Edition, Pharmacia and Upjohn Company, John Wiley & Sons, Inc., p. 503.*
Hcaplus 1981:417990 abstract, "(Phenthio)phenylamine derivatives as potential antiinflammatory compounds", Marcincal-Lefebvre et. al., 1981.*
Patani et. al., "Bioisosterism: A Rational Approach in Drug Design", Chem. Rev. 1996, 96, pp. 3147-3176.*
Hcaplus 1980:180816 abstract, "Diphenyl ethers and their use for treating liver infections in mammals", 1979, Gorvin et. al.*
Hcaplus Abstract 2004:41460, "Preparation of bisarylsulfonamide compounds and their use in cancer therapy", 2004, Wang et. al.*
Hcaplus 1960:28422, "Studies on aromatic fluorine compounds. IV. Synthesis of fluorine-containing toluenes and their derivatives", Fukui et. al., 1958.*
Hcaplus 2000:553560, "Preparation of substituted N-heterocyclyl benzamides and analogs as G-protein coupled heptahelical receptor binding compounds", Shiosaki et. al., 2000.*
Badawi, A., et al., "Uracil, 2,4-Dichlorophenol and Diphenylether Derivatives with Antimicrobial Activity," *Pharmazie*, vol. 38 (1983) pp. 838-841.
Chau, Nguyen, et al. "Synthesis of Aromatic Polysulfonamide Esters," *Journal of Polymer Science*, vol. 18 (1980) pp. 3499-3503.
Mastrukova, T.A., et al., "The Application of the Hammett Equation to the Theory of Tautomeric Equilibrium II" *Tetrahedron*, vol. 19 (1963) pp. 357-372.
Perola, Emanuele, et al., "Successful Virtual Screening of a Chemical Database for Farnesyltransferase Inhibitor Leads," *J. Med. Chem.*, vol. 43 (2000) pp. 401-408.
Tamura, Yoshinori, et al., "Highly Selective and Orally Active Inhibitors of Type IV Collagenase (MMP-9 and MMP-2): N-Sulfonylamino Acid Derivatives," *J. Med. Chem.*, vol. 41 (1998) pp. 640-649.
STN International queries, pp. 1-141.

* cited by examiner

*Primary Examiner* — D. Margaret Seaman
*Assistant Examiner* — Niloofar Rahmani
(74) *Attorney, Agent, or Firm* — McDonnell Boehnen Hulbert & Berghoff LLP; Travis Young

(57) ABSTRACT

This invention describes compounds useful as ubiquitin ligase inhibitors. The compounds of the invention are useful as inhibitors of the biochemical pathways of organisms in which ubiquitination is involved. The invention also provides for pharmaceutical compositions comprising the compounds described in the invention for the treatment of conditions that require inhibition of ubiquitin ligases. Furthermore, the invention provides for methods of inhibiting ubiquitination in a cell comprising contacting a cell in which inhibition of ubiquitination is desired with a compound according to the invention.

14 Claims, No Drawings

US 7,915,293 B2

UBIQUITIN LIGASE INHIBITORS

This application claims the benefit of priority of U.S. provisional application 60/475,223, filed May 30, 2003, and U.S. provisional application 60/509,780, filed Oct. 8, 2003.

FIELD OF THE INVENTION

This invention is in the field of ubiquitin ligases and inhibitors of ubiquitin ligases. Additionally, this invention is in the field of treating diseases or conditions associated with ubiquitination.

SUMMARY OF THE RELATED ART

Ubiquitin is a 76 amino acid protein present throughout the eukaryotic kingdom. It is a highly conserved protein and is essentially the identical protein in diverse organisms ranging from humans to yeasts to fruit flies. In eukaryotes, ubiquitin is the key component of the ATP-dependent pathway for protein degradation. Proteins slated for degradation are covalently linked to ubiquitin via an ATP-dependent process catalyzed by three separate enzymes.

Ubiquitin has also been implicated as key components in other biochemical processes. Ubiquitination of the Gag structural protein of Rous Sarcoma virus has been linked to the targeting of Gag to the cell membrane of the host cell where it can assemble into spherical particles and bud from the cell surface. Production of HIV particles has also been associated with ubiquitination and may constitute an important cellular pathway for producing infectious particles. Thus, the ubiquitin pathway may be an important target for treatment of HIV positive patients.

There is a need for inhibitors of ubiquitin ligases that can alter the ATP-dependent ubiquitination of proteins. Inhibition of ubiquitination can regulate the degradation of proteins in ways that assist in treating various disorders. Inhibitors of ubiquitin ligases may also help in treating infectious diseases such as bacterial and viral infections that depend on the cellular biochemical machinery.

The ubiquitination of these target proteins is known to be mediated by the enzymatic activity of three ubiquitin agents. Ubiquitin is first activated in an ATP-dependent manner by a ubiquitin activating agent, for example, an E1. The C-terminus of a ubiquitin forms a high energy thiolester bond with the ubiquitin activating agent. The ubiquitin is then transferred to a ubiquitin conjugating agent, for example, an E2 (also called ubiquitin moiety carrier protein), also linked to this second ubiquitin agent via a thiolester bond. The ubiquitin is finally linked to its target protein (e.g. substrate) to form a terminal isopeptide bond under the guidance of a ubiquitin ligating agent, for example, an E3. In this process, monomers or oligomers of ubiquitin are attached to the target protein. On the target protein, each ubiquitin is covalently ligated to the next ubiquitin through the activity of a ubiquitin ligating agent to form polymers of ubiquitin.

The enzymatic components of the ubiquitination pathway have received considerable attention (for a review, see Weissman, *Nature Reviews* 2:169-178 (2001)). The members of the E1 ubiquitin activating agents and E2 ubiquitin conjugating agents are structurally related and well characterized enzymes. There are numerous species of E2 ubiquitin conjugating agents, some of which act in preferred pairs with specific E3 ubiquitin ligating agents to confer specificity for different target proteins. While the nomenclature for the E2 ubiquitin conjugating agents is not standardized across species, investigators in the field have addressed this issue and the skilled artisan can readily identify various E2 ubiquitin conjugating agents, as well as species homologues (See Haas and Siepmann, *FASEB J.* 11:1257-1268 (1997)).

Generally, ubiquitin ligating agents contain two separate activities: a ubiquitin ligase activity to attach, via an isopeptide bond, monomers or oligomers of ubiquitin to a target protein, and a targeting activity to physically bring the ligase and substrate together. The substrate specificity of different ubiquitin ligating agents is a major determinant in the selectivity of the ubiquitin-mediated protein degradation process.

In eukaryotes, some ubiquitin ligating agents contain multiple subunits that form a complex called the SCF having ubiquitin ligating activity. SCFs play an important role in regulating G1 progression, and consists of at least three subunits, SKP1, Cullins (having at least seven family members) and an F-box protein (of which hundreds of species are known) which bind directly to and recruit the substrate to the complex. The combinatorial interactions between the SCF's and a recently discovered family of RING finger proteins, the ROC/APC11 proteins, have been shown to be the key elements conferring ligase activity to ubiquitin ligating agents. Particular ROC/Cullin combinations can regulate specific cellular pathways, as exemplified by the function of APC11-APC2, involved in the proteolytic control of sister chromatid separation and exit from telophase into G1 in mitosis (see King et al., supra; Koepp et al., *Cell* 97:431-34 (1999)), and ROC1-Cullin 1, involved in the proteolytic degradation of IκB$_0$ in NF-κB/IκB mediated transcription regulation (Tan et al., *Mol. Cell* 3(4):527-533 (1999); Laney et al., *Cell* 97:427-30 (1999)).

The best characterized ubiquitin ligating agent is the APC (anaphase promoting complex), which is multi-component complex that is required for both entry into anaphase as well as exit from mitosis (see King et al., *Science* 274:1652-59 (1996) for review). The APC plays a crucial role in regulating the passage of cells through anaphase by promoting ubiquitin-mediated proteolysis of many proteins. In addition to degrading the mitotic B-type cyclin for inactivation of CDC2 kinase activity, the APC is also required for degradation of other proteins for sister chromatid separation and spindle disassembly. Most proteins known to be degraded by the APC contain a conserved nine amino acid motif known as the "destruction box" that targets them for ubiquitin ubiquitination and subsequent degradation. However, proteins that are degraded during G1, including G1 cyclins, CDK inhibitors, transcription factors and signaling intermediates, do not contain this conserved amino acid motif. Instead, substrate phosphorylation appears to play an important role in targeting their interaction with a ubiquitin ligating agent for ubiquitin ubiquitination (see Hershko et al., *Ann. Rev. Biochem.* 67:429-75 (1998)).

Two major classes of E3 ubiquitin ligating agents are known: the HECT (homologous to E6-AP carboxy terminus) domain E3 ligating agents; and the RING finger domain E3 ligating agents. E6AP is the prototype for the HECT domain subclass of E3 ligating agents and is a multi-subunit complex that functions as a ubiquitin ligating agent for the tumor suppressor p53 which is activated by papillomavirus in cervical cancer (Huang et al. (1999) Science 286:1321-1326). Members of this class are homologous to the carboxyl terminus of E6AP and utilize a Cys active site to form a thiolester bond with ubiquitin, analogous to the E1 activating agents and E2 conjugating agents. However, in contrast, the members of the RING finger domain class of E3 ligating agents are thought to interact with an ubiquitin-conjugated-E2 intermediate to activate the complex for the transfer of ubiquitin to an acceptor. Examples of the RING domain class of E3 ligating agents are TRAF6, involved in IKK activation; Cbl, which targets insulin and EGF; Sina/Siah, which targets DCC; Itchy, which is involved in haematopoesis (B, T and mast cells); IAP, involved with inhibitors of apoptosis; and Mdm2 which is involved in the regulation of p53.

The RING finger domain subclass of E3 ligating agents can be further grouped into two subclasses. In one subclass, the RING finger domain and the substrate recognition domain are contained on different subunits of a complex forming the ubiquitin ligating agent (e.g., the RBx1 and the F-box subunit of the SCF complex). In the second subclass of ubiquitin ligating agents, the ligating agents have the RING finger domain and substrate recognition domain on a single subunit. (e.g., Mdm2 and cbl) (Tyers et al. (1999) Science 284:601, 603-604; Joazeiro et al. (2000) 102:549-552). A further class of ligating agents are those having a "PHD" domain and are homologs of the RING finger domain ligating agents (Coscoy et al. (2001) J. Cell Biol. 155(7):1265-1273), e.g., MEKK1. The PHD domain ligating agents are a novel class of membrane-bound E3 ligating agents.

In addition, a new class of ubiquitin ligases has been characterized. These are the U-box-containing proteins. (Patterson, Sci STKE 2002 (116:PE4 (220)). This class, for the present, represents a small number of ligases which have yet to be extensively characterized.

Mdm2 belongs to the second subclass of single subunit E3 ligating agents and is involved in regulating the function and stability of p53, an important tumor suppressor. In cells, p53 functions as a DNA-binding transcription factor which induces the expression of genes involved in DNA repair, apoptosis, and the arrest of cell growth. In approximately 50% of all human cancer p53 is inactivate by deletion or mutation. The level of p53 in the cell is maintained at low steady-state levels, and is induced and activated post-translationally by various signal pathways responsive to cellular stress (Lakin et al. (1999) Oncogene 18:7644-7655; Oren, M. (1999) J. Biol. Chem 274:36031-36,034). Stimuli that trigger the stress response and activate p53 include oxygen stress, inappropriate activation of oncogenes and agents that cause damage to DNA (e.g., ionizing radiation, chemicals, and ultra violet light).

The carboxyl terminus of Mdm2 contains a variant of the RING finger domain (Saurin et al. (1996) Trends Biochem. Sci. 21:208-214) that is critical for the activity of this E3 ligating agent. Recent studies have shown that Mdm2 mediates the ubiquitination of itself resulting in the formation of poly-ubiquitin chains on the protein (Zhihong et al. (2001) J.B.C. 276:31,357-31,367; Honda et al. (2000) Oncogene 19:1473-1476; Shengyun et al. (2000) 275:8945-8951). Further, the ubiquitin ligating activity of Mdm2 is dependent on its RING finger domain.

Typically, the ubiquitination of target proteins by E3 in cells results in the formation of poly-ubiquitin chains. An isopeptide bond is formed between the carboxyl terminus of the ubiquitin and the F-amino group of Lys in the target protein. The extension or formation of ubiquitin chains results from the formation of additional isopeptide bonds with the $Lys^{48}$ (and sometimes $Lys^{63}$) of a previously conjugated ubiquitin and the carboxyl-terminal Gly of an additional ubiquitin. The efficient recognition of a ubiquitinated target protein by a proteosome requires at least four ubiquitins linked in this configuration. However, in the case of Mdm2-mediated ubiquitination of p53, neither $Lys^{48}$ or $Lys^{63}$ is involved in the formation of poly-ubiquitin chains. Recent studies show that human Mdm2 mediates multiple mono-ubiquitination of p53 by a mechanism requiring enzyme isomerization (Zhihong et al. (2001) J. Biol. Chem. 276:31, 357-31,367). Further, in vitro, the transfer of ubiquitin to p53 can occur independent of E1 when using an E2 pre-conjugated with ubiquitin. These results suggest that the pre-conjugated E2 can bind to Mdm2 and thereafter transfer the ubiquitin to the Mdm2 in the absence of an E1.

Thus, ubiquitin agents, such as the ubiquitin activating agents, ubiquitin conjugating agents, and ubiquitin ligating agents, are key determinants of the ubiquitin-mediated proteolytic pathway that results in the degradation of targeted proteins and regulation of cellular processes. Consequently, agents that modulate the activity of such ubiquitin agents may be used to upregulate or downregulate specific molecules involved in cellular signal transduction. Disease processes can be treated by such up- or down regulation of signal transducers to enhance or dampen specific cellular responses. This principle has been used in the design of a number of therapeutics, including phosphodiesterase inhibitors for airway disease and vascular insufficiency, kinase inhibitors for malignant transformation and Proteasome inhibitors for inflammatory conditions such as arthritis.

Due to the importance of ubiquitin-mediated proteolysis in cellular process, for example cell cycle regulation, there is a need for a fast and simple means for identifying the physiological role of ubiquitin agents that are catalytic components of this enzymatic pathway, and for identifying which ubiquitin agents are involved in various regulatory pathways. Thus, an object of the present invention is to provide methods of assaying for the physiological role of ubiquitin agents, and for providing methods for determining which ubiquitin agents are involved together in a variety of different physiological pathways.

BRIEF SUMMARY OF THE INVENTION

The invention provides compounds and compositions for inhibiting ubiquitin ligases. These inhibitors can be used in treating various conditions where ubiquitination is involved. They can also be used as research tools to study the role of ubiquitin in various natural and pathological processes.

In a first aspect, the invention provides compounds that are useful as inhibitors of ubiquitin ligases.

In a second aspect, the invention provides a composition comprising an inhibitor of ubiquitination according to the invention and a pharmaceutically acceptable carrier, excipient, or diluent.

In a third aspect, the invention provides methods of inhibiting ubiquitination in a cell, comprising contacting a cell in which inhibition of ubiquitination is desired with an inhibitor of ubiquitin ligases of the invention.

In a fourth aspect, the invention provides methods for treating cell proliferative diseases or conditions, comprising administering to a patient in need thereof an effective amount of an inhibitor of ubiquitination of the invention.

The foregoing only summarizes certain aspects of the invention and is not intended to be limiting in nature. These aspects and other aspects and embodiments are described more fully below.

DETAILED DESCRIPTION OF THE INVENTION

The invention provides compounds and methods for inhibiting ubiquitination. The invention also provides compositions and methods for treating cell proliferative diseases and other conditions in which ubiquitination is an important component.

The invention provides for compounds of the formula (Ia):

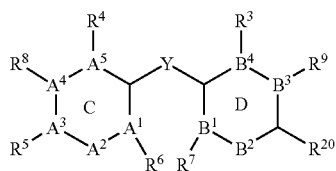

or a pharmaceutically acceptable salt or complex thereof, wherein
ring C and D are independently saturated, unsaturated, aromatic or nonaromatic;
- $R^1$ and $R^{1a}$ are independently —H, $C_{1-6}$-hydrocarbyl, $C_5$-$C_{12}$-heterocyclyl-$C_0$-$C_6$-hydrocarbyl, aryl-$C_0$-$C_6$-hydrocarbyl, $C_5$-$C_{12}$-heteroaryl-$C_0$-$C_6$-hydrocarbyl, —C(=X)-$L^1$-$R^{10}$, $C_4$-$C_{10}$-hydrocarbyl-NH—C(O)—$C_6H_4$—, aryl-oxy-$C_1$-$C_6$-hydrocarbyl-, aryl-oxy-aryl-$SO_2$—, $(CH_3)_2N$—$C_1$-$C_6$-hydrocarbyl, $(NH_2)(NH)C$—NH—$(CH_2)_3$—$CH(NH_2CO)$—, or =$C(R^{13})(R^{14})$;
- X is =O, =S, or =NH;
- $L^1$ is a covalent bond, —NH—, —O—, —S—, or $C_1$-$C_3$-hydrocarbyl;
- $R^{10}$ is $C_1$-$C_6$-hydrocarbyl, $C_5$-$C_{12}$-heterocyclyl, aryl, or $C_5$-$C_{12}$-heteroaryl;
- $R^2$ is H, $C_1$-$C_6$-hydrocarbyl, or aryl;
- or $R^1$ and $R^2$ together with the nitrogen to which they are both covalently bound are a $C_0$-$C_4$-hydrocarbyl-$C_5$-$C_{12}$-hetrocyclyl;
- or $R^1$ and $R^2$ together are =$C(R^{11})(R^{12})$;
- $R^{11}$ is —H or —NH-aryl;
- $R^{12}$ is —$N(R^{13})(R^{14})$ or —$SR^{13}$;
- $R^{13}$ and $R^{14}$ and are independently selected from —H, —OH, or $C_1$-$C_3$-hydrocarbyl;
- $R^3$ is —H, halo, —$NO_2$, NO, —$NH_2$, —NH—C(O)$R^{17}$, —CN, $C_1$-$C_5$-hydrocarbyl-C(O)—, or $C_1$-$C_6$-hydrocarbyl;
- $R^4$ is —H, halo, —$N(R^{18})_2$, —$NO_2$, NO, —C(O)$N(R^{18})_2$, $C_1$-$C_6$-hydrocarbyl, $C_1$-$C_3$-hydrocarbyl-C(O)—NH—, or —CN;
- $R^5$ is —H, —$NO_2$, NO, —$NH_2$, —NH—C(O)$R^{17}$, —$C_1$-$C_3$-hydrocarbyl, mono- to per-halogenated —$C_1$-$C_3$-hydrocarbyl, $N(R^{20})(R^{21})SO_2$—, aryl-$SO_2$—NH—, aryl-oxy-aryl-$SO_2$—NH—, aryl-NH—$SO_2$—, or aryl-CO—NH—;
- $R^{15}$ and $R^{16}$ are independently $C_1$-$C_3$-alkyl or together with the nitrogen to which they are covalently bound form a $C_5$-$C_6$-heterocyclyl;
- $R^6$ is —H, halo, —CN, —$C_1$-$C_6$-hydrocarbyl, mono- to per-halogenated —$C_1$-$C_6$-hydrocarbyl, —$SO_2$, —$NO_2$, —NO, —$NH_2$, or —NH—C(O)$R^{17}$;
- $R^{17}$ is —H or —$C_1$-$C_6$-hydrocarbyl;
- $R^{20}$ is —S(O)$_2$—$N(R^1)(R^2)$ or —$N(R^{1a})S(O)_2R^1$;
- $R^8$ is —H, halo, —OH, —$C_1$-$C_3$-hydrocarbyl-O—, mono- to per-halogenated —$C_1$-$C_3$-hydrocarbyl-O—, —$C_1$-$C_3$-hydrocarbyl, mono- to per-halogenated —$C_1$-$C_3$-hydrocarbyl-, —CN, —$SO_2$ or —$NO_2$, —NO, —$NH_2$, or —NH—C(O)$R^{17}$;
- $R^7$, and $R^9$ independently are —H, halo, —OH, $C_{1-3}$-hydrocarbyl-O—, mono- to per-halogenated —$C_1$-$C_3$-hydrocarbyl-O—, —$C_1$-$C_3$-hydrocarbyl, mono- to per-halogenated —$C_1$-$C_3$-hydrocarbyl-, —CN, —$SO_2$, —$NO_2$, —NO, —$NH_2$, or —NH—C(O)$R^{17}$;
- Y is —O—, —S—, —S(O)—, —$SO_2$—, —C(O)—, or —$NR^{18}$;
- $R^{18}$ is —H, $C_1$-$C_6$-hydrocarbyl, —C(O)$R^{19}$, —$SO_2R^{19}$, $C(O)NHR^{19}$, $CSNHR^{19}$, $CNNHR^{19}$, or $CO_2R^{19}$;
- $R^{19}$ is —H, —OH, or $C_1$-$C_3$-hydrocarbyl;
- $A^1$, $A^2$, $A^3$, $A^4$, $A^5$, $B^1$, $B^2$, $B^3$, and $B^4$ are independently oxygen, sulfur, nitrogen or carbon with the proviso that when any one of $A^1$, $A^3$, $A^4$, $A^5$, $B^1$, $B^3$, and $B^4$ is nitrogen and ring C and D are aromatic, then the substituent bonded to that position is absent and when any one of $A^1$, $A^3$, $A^4$, $A^5$, $B^1$, $B^3$, and $B^4$ is oxygen or sulfur and ring C and D are saturated, then the substitutent bonded at that position is absent, and further provided that when one of $A^1$, $A^2$, $A^3$, $A^4$, $A^5$, $B^1$, $B^2$, $B^3$, and $B^4$ are S or O, it is not adjacent to another annular S or O;
- wherein each of the aryl, heteroaryl, heterocyclyl, and hydrocarbyl groups of $R^1$ to $R^{19}$ is optionally substituted by one or more groups selected from halo, —OH, —$NH_2$, $C_1$-$C_6$-hydrocarbyl-C(O)—, oxo, $C_1$-$C_6$-hydrocarbyl-(O)—, mono- to per-halogenated $C_1$-$C_6$-hydrocarbyl-O—, $C_1$-$C_6$-hydrocarbyl, mono- to per-halogenated $C_1$-$C_6$-hydrocarbyl, —CN, —$NO_2$, —NO, —$NH_2$, —NH—C(O)$R^{22}$, or —$SO_2$; and
- provided that the compound is not one of the following combinations:

| $R^1$ | $R^2$ | $R^3$ | $R^4$ | $R^5$ | $R^6$ | $R^7$ | $R^8$ | $R^9$ |
|---|---|---|---|---|---|---|---|---|
| ![3-pyridyl C(=NH)CH3] | H | Cl | Cl | —$NO_2$ | H | Cl | H | H |
| ![CH2Cl C(=NH)] | H | Cl | Cl | $NO_2$ | H | Cl | H | H |
| ![4-Cl-phenyl C(=NH)CH3] | H | Cl | H | $NO_2$ | H | Cl | H | H |
| H | H | Cl | H | $NO_2$ | H | Cl | H | H |
| H | H | Cl | Cl | $NO_2$ | H | Cl | H | H |

-continued

| R¹ | R² | R³ | R⁴ | R⁵ | R⁶ | R⁷ | R⁸ | R⁹ |
|---|---|---|---|---|---|---|---|---|
| 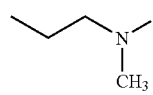 | —CH₃ | NO₂ | H | NO₂ | H | H | H | H |
| —CH₃ | —CH₃ | Cl | H | NO₂ | H | H | H | H |
| H | H | H | H | NO₂ | H | Cl | H | H |
|  | H | H | H | NO₂ | H | H | H | H |
| 3,5-dichlorophenyl | H | Cl | Cl | NO₂ | H | Cl | H | H |
| 3-chloro,4-fluoro phenyl | H | Cl | Cl | NO₂ | H | Cl | H | H |
| CH₃ | CH₃ | H | H | NO₂ | CN | H | H | H |
| CH₃CH₂ | CH₃CH₂ | H | H | NO₂ | CN | H | H | H |
| Cyclohexyl | H | H | H | NO₂ | H | H | H | H |
| CH₃ | CH₃ | H | H | NO₂ | H | H | H | H |
| CH₃ | H | H | H | NO₂ | H | H | H | H |
| NH₂ | H | H | H | NO₂ | H | H | H | H |
| NH₂ | H | Cl | H | NO₂ | H | H | H | H |
| NH₂ | H | Cl | H | NO₂ | H | Cl | H | H |
| CH₃CH₂ | CH₃ | Cl | Cl | NO₂ | H | H | H | H |
| CH₃C=O | H | H | H | NO₂ | H | H | H | H |
| H | H | H | H | NO₂ | H | H | H | H |

The invention also provides for compounds of the formula (I):

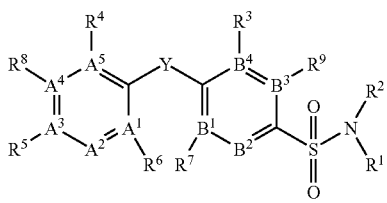

or a pharmaceutically acceptable salt or complex thereof, wherein $R^1$ is —H, $C_{1-6}$-hydrocarbyl, $C_5$-$C_{12}$-heterocyclyl-$C_0$-$C_6$-hydrocarbyl, aryl-$C_0$-$C_6$-hydrocarbyl, $C_5$-$C_{12}$-heteroaryl-$C_0$-$C_6$-hydrocarbyl, —C(=X)-$L^1$-$R^{10}$, $C_4$-$C_{10}$-hydrocarbyl-NH—C(O)—$C_6H_4$—, aryl-oxy-$C_1$-$C_6$-hydrocarbyl-, aryloxy-aryl-SO₂—, (CH₃)₂N—$C_1$-$C_6$-hydrocarbyl, or (NH₂)(NH)C—NH—(CH₂)₃—CH(NH₂CO)—;

X is =O, =S, or =NH;

$L^1$ is a covalent bond, —NH—, —O—, —S—, or $C_1$-$C_3$-hydrocarbyl;

$R^{10}$ is $C_1$-$C_6$-hydrocarbyl, $C_5$-$C_{12}$-heterocyclyl, aryl, or $C_5$-$C_{12}$-heteroaryl;

$R^2$ is H, $C_1$-$C_6$-hydrocarbyl, or aryl;

or $R^1$ and $R^2$ together with the nitrogen to which they are both covalently bound are a $C_0$-$C_4$-hydrocarbyl-$C_5$-$C_{12}$-hetrocyclyl;

or $R^1$ and $R^2$ together are =C($R^{11}$)($R^{12}$);

$R^{11}$ is —H or —NH-aryl;

$R^{12}$ is —N($R^{13}$)($R^{14}$) or —S$R^{13}$;

$R^{13}$ and $R^{14}$ are independently selected from —H, —OH, or $C_1$-$C_3$-hydrocarbyl;

$R^3$ is —H, halo, —NO₂, NO, —NH₂, or —NH—C(O)$R^{17}$, —CN, $C_1$-$C_5$-hydrocarbyl-C(O)—, or $C_1$-$C_6$-hydrocarbyl;

$R^4$ is —H, halo, —N($R^{18}$)₂, —NO₂, NO, —C(O)N($R^{18}$)₂, $C_1$-$C_6$-hydrocarbyl, $C_1$-$C_3$-hydrocarbyl-C(O)—NH—, or —CN;

$R^5$ is —H, —NO₂, NO, —NH₂, —NH—C(O)$R^{17}$, —$C_1$-$C_3$-hydrocarbyl, mono- to per-halogenated —$C_1$-$C_3$-hydrocarbyl, N($R^{15}$)($R^{16}$)SO₂—, aryl-SO₂—NH—, aryl-oxy-aryl-SO₂—NH—, aryl-NH—SO₂—, or aryl-CO—NH—;

$R^{15}$ and $R^{16}$ are independently $C_1$-$C_3$-alkyl or together with the nitrogen to which they are covalently bound form a $C_5$-$C_6$-heterocyclyl;

$R^6$ is —H, halo, —CN, —$C_1$-$C_6$-hydrocarbyl, mono- to per-halogenated —$C_1$-$C_6$-hydrocarbyl, —SO₂, —NO₂, —NO, —NH₂, or —NH—C(O)$R^{17}$;

$R^{17}$ is —H or —$C_1$-$C_6$-hydrocarbyl;

$R^8$ is —H, halo, —OH, —$C_1$-$C_3$-hydrocarbyl-O—, mono- to per-halogenated —$C_1$-$C_3$-hydrocarbyl-O—, —$C_1$-$C_3$-hydrocarbyl, mono- to per-halogenated —$C_1$-$C_3$-hydrocarbyl-, —CN, —SO₂, —NO₂, —NO, —NH₂, or —NH—C(O)$R^{17}$;

$R^7$ and $R^9$ independently are —H, halo, —OH, —$C_1$-$C_3$-hydrocarbyl-O—, mono- to per-halogenated $C_1$-$C_3$-hydrocarbyl-O—, $C_1$-$C_3$-hydrocarbyl, mono- to per-halogenated $C_1$-$C_3$-hydrocarbyl-, —CN, —SO₂, —NO₂, —NO, —NH₂, or —NH—C(O)$R^{17}$;

Y is —O—, —S—, —S(O)—, —SO₂—, —C(O)—, or —N($R^{18}$)—;

$R^{18}$ is —H, $C_1$-$C_6$-hydrocarbyl, —C(O)$R^{19}$, —SO₂$R^{19}$, C(O)NH$R^{19}$, CSNH$R^{19}$, CNNH$R^{19}$, or CO₂$R^{19}$;

$R^{19}$ is —H, —OH, or $C_1$-$C_3$-hydrocarbyl;

$A^1$, $A^2$, $A^3$, $A^4$, $A^5$, $B^1$, $B^2$, $B^3$, and $B^4$ are independently nitrogen or carbon with the proviso that when any one of $A^1$, $A^3$, $A^4$, $A^5$, $B^1$, $B^3$, and $B^4$ is nitrogen, then the substituent bonded to that position is absent, and further provided that when one of $A^1$, $A^2$, $A^3$, $A^4$, $A^5$, $B^1$, $B^2$, $B^3$, and $B^4$ are S or O, it is not adjacent to another annular S or O;

wherein each of the aryl, heteroaryl, heterocyclyl, and hydrocarbyl groups of $R^1$ to $R^{19}$ is independently optionally substituted by one or more groups selected from halo, —OH, —NH$_2$, C$_1$-C$_6$-hydrocarbyl-C(O)—, oxo, C$_1$-C$_6$-hydrocarbyl-(O)—, mono- to per-halogenated C$_1$-C$_6$-hydrocarbyl-O—, C$_1$-C$_6$-hydrocarbyl, mono- to per-halogenated C$_1$-C$_6$-hydrocarbyl, —CN, —NO$_2$, —NO, —NH$_2$, —NH—C(O)R$^{22}$, or —SO$_2$; and provided that the compound is not one of the following combinations:

ferred embodiment, the invention provides for compounds wherein $R^9$ is —H or —F.

In one embodiment, the invention provides for compounds wherein $R^3$ is —H, —Cl, or —NO$_2$; $R^4$ is —H, —Cl, or —NO$_2$; $R^5$ is —H or —NO$_2$; $R^6$ is —H or —Cl; $R^7$ is —H or —Cl; $R^8$ is —H or —Cl; and $R^9$ is —H or —F.

In another embodiment of the invention, the compounds are compounds wherein $R^1$ is aryl optionally substituted by from 1-3 moieties independently selected from halo and mono- to per-halogenated C$_1$-C$_3$-hydrocarbyl-O—, mono to

| $R^1$ | $R^2$ | $R^3$ | $R^4$ | $R^5$ | $R^6$ | $R^7$ | $R^8$ | $R^9$ |
|---|---|---|---|---|---|---|---|---|
| 1-(pyridin-3-yl)ethanimine (HN=C(CH$_3$)-pyridyl) | H | Cl | Cl | —NO$_2$ | H | Cl | H | H |
| 1-chloro-propan-2-imine (ClCH$_2$-C(CH$_3$)=NH) | H | Cl | Cl | NO$_2$ | H | Cl | H | H |
| 1-(4-chlorophenyl)ethanimine | H | Cl | H | NO$_2$ | H | Cl | H | H |
| H | H | Cl | H | NO$_2$ | H | Cl | H | H |
| H | H | Cl | Cl | NO$_2$ | H | Cl | H | H |
| (CH$_3$)$_2$N-CH$_2$CH$_2$CH$_2$- | —CH$_3$ | NO$_2$ | H | NO$_2$ | H | H | H | H |
| —CH$_3$ | —CH$_3$ | Cl | H | NO$_2$ | H | H | H | H |
| H | H | H | H | NO$_2$ | H | Cl | H | H |
| 2-methylthiazol-4-yl | H | H | H | NO$_2$ | H | H | H | H |
| 3,5-dichlorophenyl | H | Cl | Cl | NO$_2$ | H | Cl | H | H |
| 3-chloro,4-fluoro phenyl | H | Cl | Cl | NO$_2$ | H | Cl | H | H |
| CH$_3$ | CH$_3$ | H | H | NO$_2$ | CN | H | H | H |
| CH$_3$CH$_2$ | CH$_3$CH$_2$ | H | H | NO$_2$ | CN | H | H | H |
| cyclohexyl | H | H | H | NO$_2$ | H | H | H | H |
| CH$_3$ | CH$_3$ | H | H | NO$_2$ | H | H | H | H |
| CH$_3$ | H | H | H | NO$_2$ | H | H | H | H |
| NH$_2$ | H | H | H | NO$_2$ | H | H | H | H |
| NH$_2$ | H | Cl | H | NO$_2$ | H | H | H | H |
| NH$_2$ | H | Cl | H | NO$_2$ | H | Cl | H | H |
| CH$_3$CH$_2$ | CH$_3$ | Cl | Cl | NO$_2$ | H | H | H | H |
| CH$_3$C=O | H | H | H | NO$_2$ | H | H | H | H |
| H | H | H | H | NO$_2$ | H | H | H | H |

In a preferred embodiment, the invention provides for compounds wherein $R^3$ is —H, —Cl, or —NO$_2$. In another preferred embodiment, the invention provides for compounds wherein $R^4$ is —H, —Cl, or —NO$_2$. In yet another preferred embodiment, the invention provides for compounds wherein $R^5$ is —H or —NO$_2$. In still another preferred embodiment, the invention provides for compounds wherein $R^6$ is —H or —Cl. In another preferred embodiment, the invention provides for compounds wherein $R^7$ is —H or —Cl. In yet another preferred embodiment, the invention provides for compounds wherein $R^8$ is —H or —Cl. In still another preper halogenated C$_1$-C$_3$-hydrocarbyl. More preferably, $R^1$ is selected from CF$_3$-phenyl, 1-chloro, 4-fluorophenyl, 2,4-difluorophenyl, 3,5-dichlorophenyl.

In another embodiment, the invention provides for compounds wherein $R^1$ and $R^2$ together with the nitrogen atom to which they are both attached form a piperidinyl which is optionally substituted by one or more groups selected from halo, —OH, —NH$_2$, C$_1$-C$_4$-hydrocarbyl-C(O)—, oxo, C$_1$-C$_3$-hydrocarbyl-(O)—, mono- to per-halogenated C$_1$-C$_3$-hydrocarbyl-O—, C$_1$-C$_3$-hydrocarbyl, mono- to per-halogenated C$_{1-3}$-hydrocarbyl, aryl-O—, —CN, —NO$_2$, or —SO$_2$. More preferably, the piperidinyl is 3,5-dimethylpiperidinyl.

In yet another embodiment, the invention provides for compound wherein $R^1$ is $C_1$-$C_3$-hydrocarbyl-C(=NH)- which is optionally substituted by one or more groups selected from halo, —OH, —NH$_2$, $C_1$-$C_4$-hydrocarbyl-C(O)—, oxo, $C_1$-$C_3$-hydrocarbyl-(O)—, mono- to per-halogenated $C_1$-$C_3$-hydrocarbyl-O—, $C_1$-$C_3$-hydrocarbyl, mono- to per-halogenated $C_{1-3}$-hydrocarbyl, aryl-O—, —CN, —NO$_2$, or —SO$_2$. More preferrably $R^1$ is CH$_3$—C(=NH)—.

The invention also provides, in another particular aspect, compounds wherein $R^1$ is $C_4$-$C_{10}$-hydrocarbyl-NH—CO— $C_6H_4$- which is optionally substituted by one or more groups selected from halo, —OH, —NH$_2$, $C_1$-$C_4$-hydrocarbyl-C(O)—, oxo, $C_1$-$C_3$-hydrocarbyl-(O)—, mono- to per-halogenated $C_1$-$C_3$-hydrocarbyl-O—, $C_1$-$C_3$-hydrocarbyl, mono- to per-halogenated $C_1$-$C_3$-hydrocarbyl, aryl-O—, —CN, —NO$_2$, or —SO$_2$. More preferably $R^1$ is cyclopropyl-CH$_2$—NH—CO-phenyl.

In a more preferred embodiment, the invention provides for compounds wherein $R^1$ is selected from the following groups:

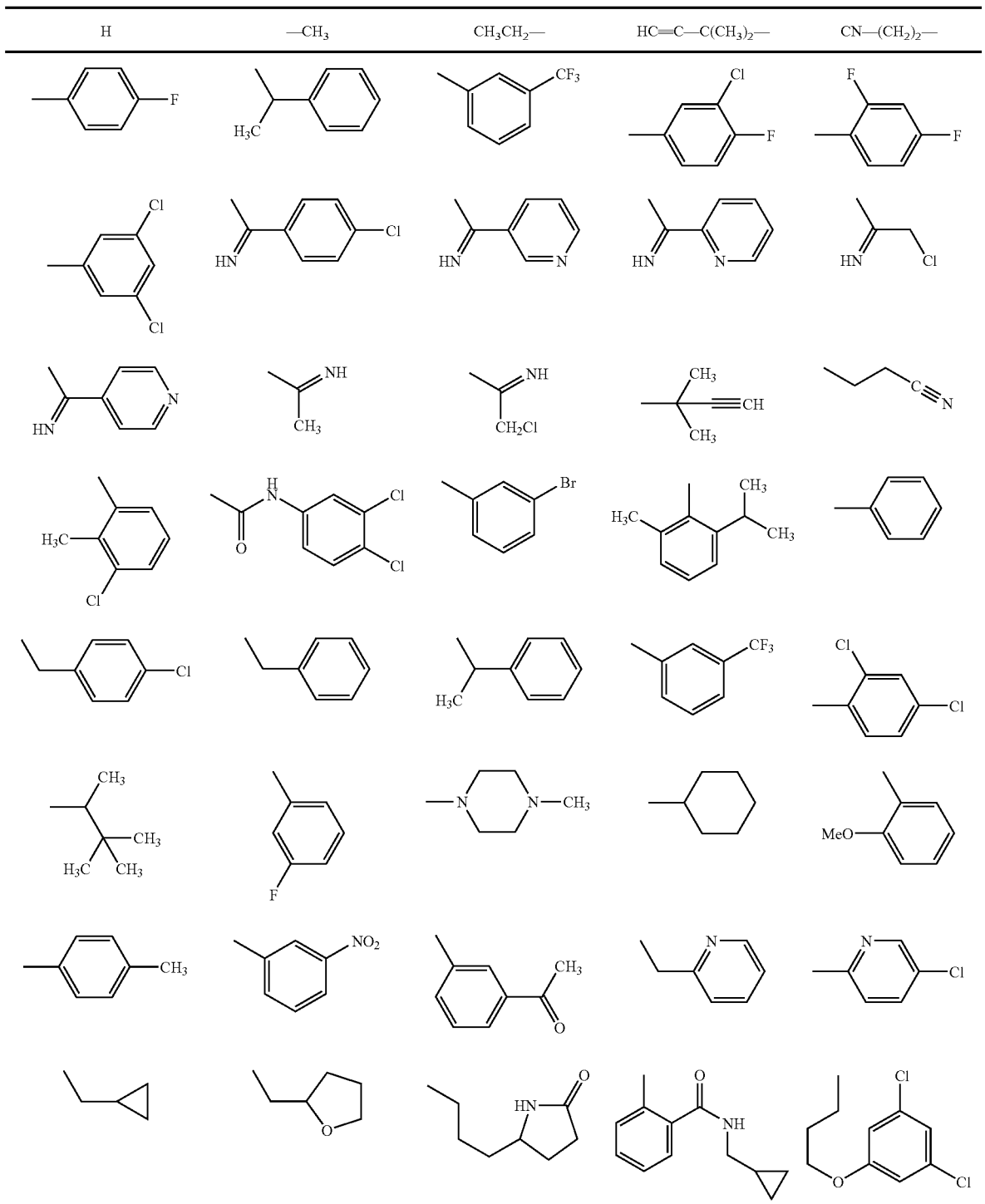

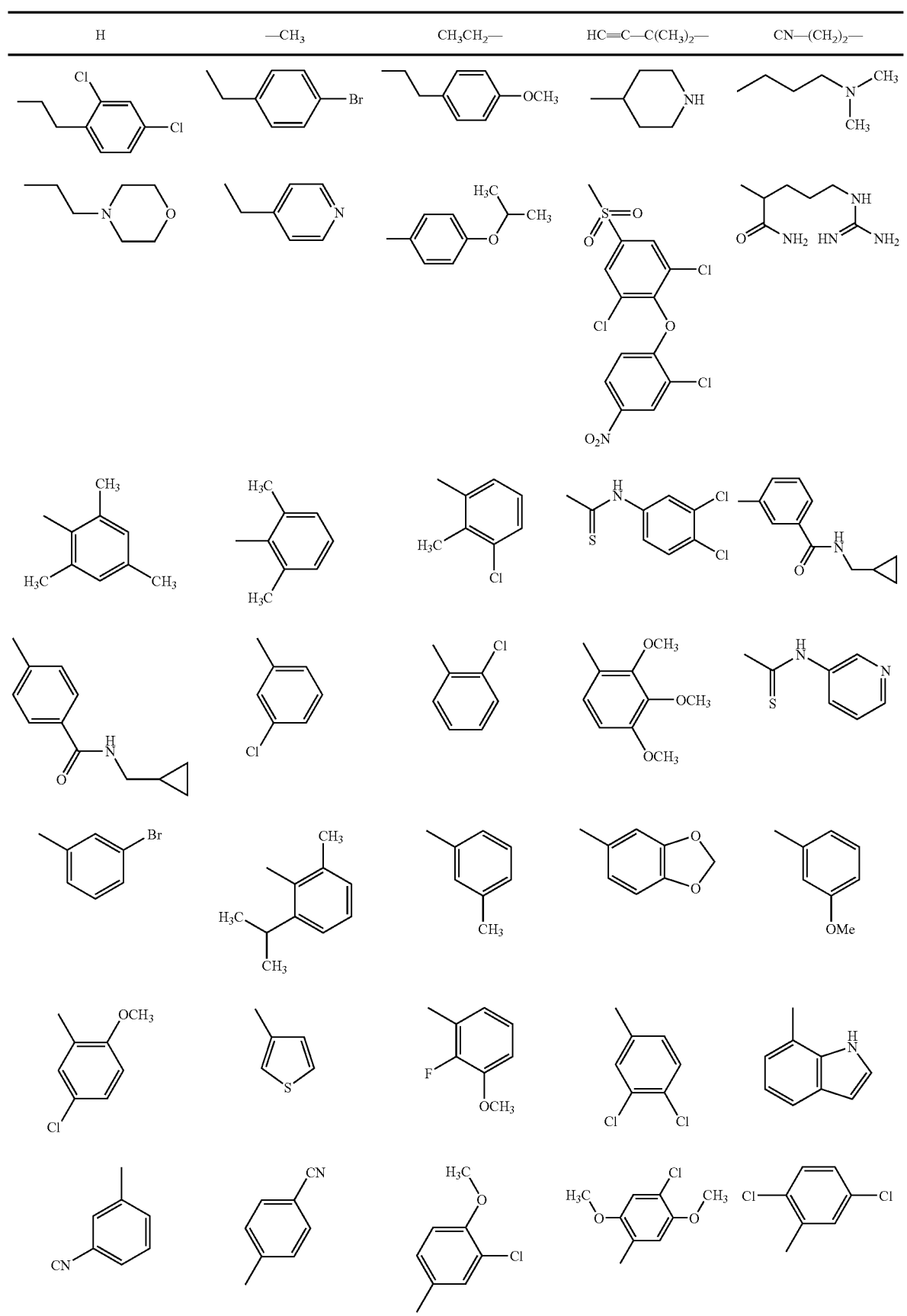

-continued

| H | —CH₃ | CH₃CH₂— | HC≡C—C(CH₃)₂— | CN—(CH₂)₂— |
|---|---|---|---|---|

-continued
| H | —CH₃ | CH₃CH₂— | HC≡C—C(CH₃)₂— | CN—(CH₂)₂— |
|---|---|---|---|---|
| 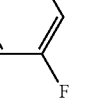 | 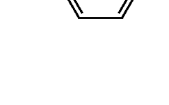 | 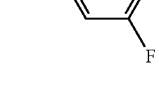 | 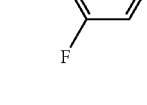 | 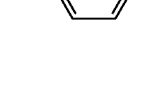 |
| 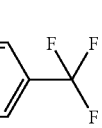 | 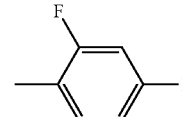 | 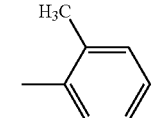 | 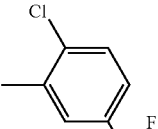 | 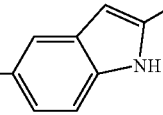 |
| 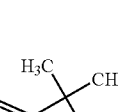 | 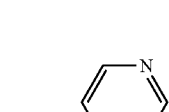 | 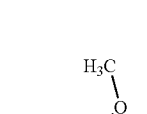 | 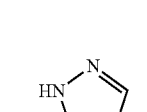 | 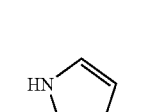 |
|  | 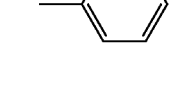 | 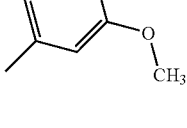 | 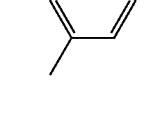 | 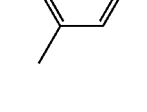 |
| 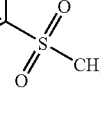 | 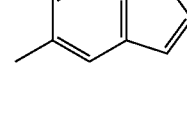 | 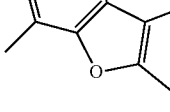 | 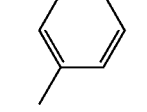 | 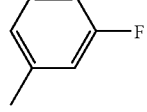 |
| 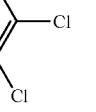 | 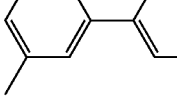 | 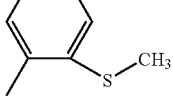 | 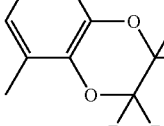 | 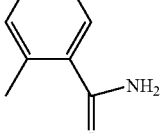 |
| 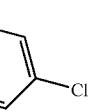 | 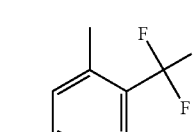 | 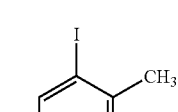 | 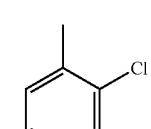 | 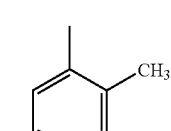 |

-continued

| H | —CH₃ | CH₃CH₂— | HC≡C—C(CH₃)₂— | CN—(CH₂)₂— |
|---|---|---|---|---|

-continued

In still another aspect, the invention provides for compounds wherein $R^2$ is selected from

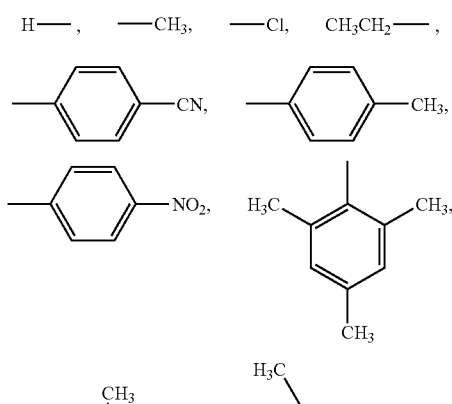

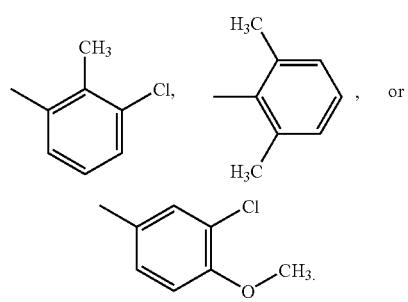

In another preferred embodiment, the compounds of the invention are compounds wherein $R^1$ and $R^2$ together with the nitrogen to which they are both covalently bound form a moiety selected from the following groups:

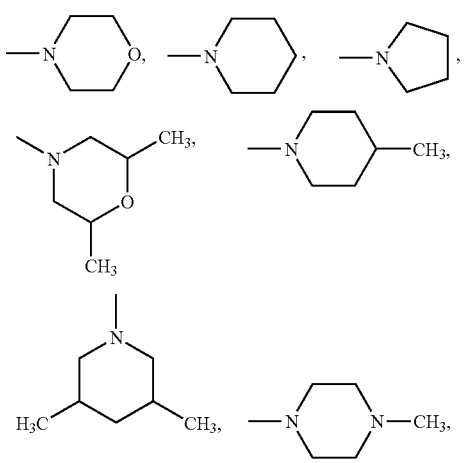

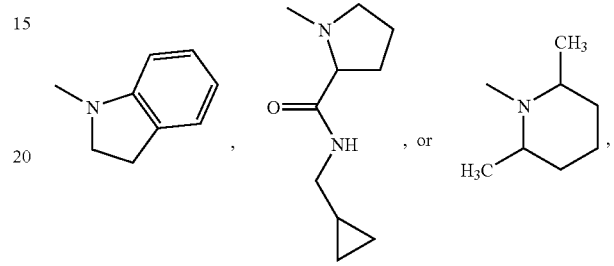

In a more preferred embodiment, the invention provides for compounds wherein $R^1$ and $R^2$ together form one of the following groups:

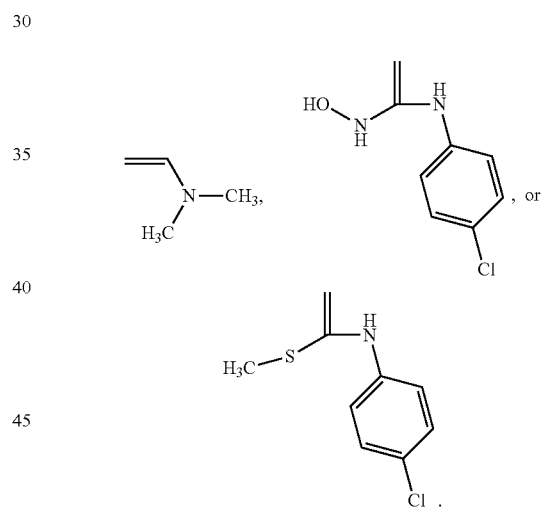

In one preferred embodiment ring C and D are independently pyrimidine, pyridazine, pyrazine, triazine, piperazine, piperidine, morpholine or thiomorpholine.

In another aspect, the invention provides compounds of formula (II):

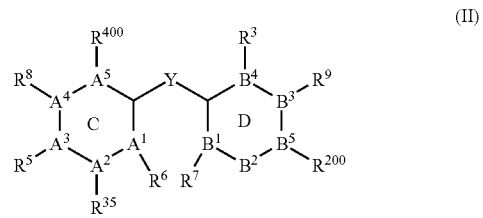

or pharmaceutically acceptable salts or complexes thereof, wherein ring C and D are independently saturated, unsaturated, aromatic or nonaromatic;

$R^1$ and $R^{1a}$ are independently —H, $C_{1-6}$-hydrocarbyl, $C_5$-$C_{12}$-heterocyclyl-$C_0$-$C_6$-hydrocarbyl, aryl-$C_0$-$C_6$-hydrocarbyl, $C_5$-$C_{12}$-heteroaryl-$C_1$-$C_6$-hydrocarbyl, —C(=X)-$L^1$-$R^{10}$, $C_4$-$C_{10}$-hydrocarbyl-NH—C(O)$C_6H_4$—, aryl-oxy-$C_1$-$C_6$-hydrocarbyl-, aryl-oxy-aryl-$SO_2$—, $(CH_3)_2N$—$C_1$-$C_6$-hydrocarbyl, $(NH_2)(NH)C$—NH—$(CH_2)_3$—$CH(NH_2CO)$—, or =C($R^{13}$)($R^{14}$);

X is =O, =S, or =NH;

$L^1$ is a covalent bond, —NH—, —O—, —S—, or $C_1$-$C_3$-hydrocarbyl;

$R^{10}$ is $C_1$-$C_6$-hydrocarbyl, $C_5$-$C_{12}$-heterocyclyl, aryl, or $C_5$-$C_{12}$-heteroaryl;

$R^2$ is H, $C_1$-$C_6$-hydrocarbyl, or aryl;

or $R^1$ and $R^2$ together with the nitrogen to which they are both covalently bound are a $C_0$-$C_4$-hydrocarbyl-$C_5$-$C_{12}$-hetrocyclyl;

or $R^1$ and $R^2$ together are =C($R^{11}$)($R^{12}$);

$R^{11}$ is —H or —NH-aryl;

$R^{12}$ is —N($R^{13}$)($R^{14}$) or —S$R^{13}$;

$R^{13}$ and $R^{14}$ and are independently selected from —H, —OH, or $C_1$-$C_3$-hydrocarbyl;

$R^3$ is —H, halo, —$NO_2$, NO, —$NH_2$, —NH—C(O)$R^{17}$, —CN, $C_1$-$C_5$-hydrocarbyl-C(O)—, or $C_1$-$C_6$-hydrocarbyl;

$R^{400}$ is —H, halo, —N($R^{18}$)$_2$, —$NO_2$, NO, —C(O)N($R^{18}$)$_2$, $C_1$-$C_6$-hydrocarbyl, $C_1$-$C_3$-hydrocarbyl-C(O)—NH—, mono- to per-halogenated —$C_1$-$C_6$-hydrocarbyl, or —CN;

$R^5$ and $R^{35}$ independently are —H, —$NO_2$, NO, —$NH_2$, —NH—C(O)$R^{17}$, —$C_1$-$C_3$-hydrocarbyl, mono- to per-halogenated —$C_1$-$C_3$-hydrocarbyl, N($R^1$)($R^2$)$SO_2$—, aryl-$SO_2$—NH—, aryl-oxy-aryl-$SO_2$—NH—, aryl-NH—$SO_2$—, or aryl-CO—NH—;

$R^6$ is —H, halo, —CN, —$C_1$-$C_6$-hydrocarbyl, mono- to per-halogenated —$C_1$-$C_6$-hydrocarbyl, —$SO_2$, —$NO_2$, —NO, —$NH_2$, or —NH—C(O)$R^{17}$;

$R^{17}$ is —H or —$C_1$-$C_6$-hydrocarbyl;

$R^{200}$ is —S(O)$_2$—N($R^1$)($R^2$), —N($R^{1a}$)S(O)$_2$$R^1$, —S(O)$_2$$R^1$, —C(O)NH$R^1$, —NHC(O)$R^1$, or NHC(O)NH$R^1$;

$R^8$ is, —H, halo, —OH, —$C_{1-3}$-hydrocarbyl-O—, mono- to per-halogenated —$C_1$-$C_3$-hydrocarbyl-O—, —$C_1$-$C_3$-hydrocarbyl, mono- to per-halogenated —$C_1$-$C_3$-hydrocarbyl-, —CN, —$SO_2$ or —$NO_2$, —NO, —$NH_2$, or —NH—C(O)$R^{17}$;

$R^7$, and $R^9$ independently are —H, halo, —OH, $C_{1-3}$-hydrocarbyl-O—, mono- to per-halogenated —$C_1$-$C_3$-hydrocarbyl-O—, —$C_1$-$C_3$-hydrocarbyl, mono- to per-halogenated —$C_1$-$C_3$-hydrocarbyl-, —CN, —$SO_2$, —$NO_2$, —NO, —$NH_2$, or —NH—C(O)$R^{17}$;

Y is —O—, —S—, —S(O)—, —$SO_2$—, —C(O)—, or —N$R^{18}$;

$R^{18}$ is —H, $C_1$-$C_6$-hydrocarbyl, —C(O)$R^{19}$, —$SO_2$$R^{19}$, C(O)NH$R^{19}$, CSNH$R^{19}$, CNNH$R^{19}$, or CO$_2$$R^{19}$;

$R^{19}$ is —H, —OH, or $C_1$-$C_3$-hydrocarbyl;

$A^1$, $A^2$, $A^3$, $A^4$, $A^5$, $B^1$, $B^2$, $B^3$, $B^4$, and $B^5$ are independently oxygen, sulfur, nitrogen or carbon with the proviso that when any one of $A^1$, $A^3$, $A^4$, $A^5$, $B^1$, $B^3$, $B^4$ and $B^5$ is nitrogen and ring C and D are aromatic, then the substituent bonded to that position is absent and when any one of $A^1$, $A^3$, $A^4$, $A^5$, $B^1$, $B^3$, $B^4$ and $B^5$ is oxygen or sulfur and ring C and D are saturated, then the substitutent bonded at that position is absent, and further provided that when one of $A^1$, $A^2$, $A^3$, $A^4$, $A^5$, $B^1$, $B^2$, $B^3$, $B^4$ and $B^5$ are S or O, it is not adjacent to another annular S or O;

wherein each of the aryl, heteroaryl, heterocyclyl, and hydrocarbyl groups above is optionally substituted by one or more groups selected from halo, —OH, —$NH_2$, $C_1$-$C_6$-hydrocarbyl-C(O)—, oxo, $C_1$-$C_6$-hydrocarbyl-(O)—, mono- to per-halogenated $C_1$-$C_6$-hydrocarbyl-O—, $C_1$-$C_6$-hydrocarbyl, mono- to per-halogenated $C_1$-$C_6$-hydrocarbyl, —CN, —$NO_2$, —NO, —$NH_2$, —NH—C(O)$R^{18}$, or —$SO_2$; and provided that when $R^{35}$ is H and $R^{200}$ is —S(O)$_2$—N($R^1$)($R^2$) or —N($R^{1a}$)S(O)$_2$$R^1$, the compound is not one of the following combinations:

| $R^1$ | $R^2$ | $R^3$ | $R^4$ | $R^5$ | $R^6$ | $R^7$ | $R^8$ | $R^9$ |
|---|---|---|---|---|---|---|---|---|
| HN=C(CH₃)-(3-pyridyl) | H | Cl | Cl | —$NO_2$ | H | Cl | H | H |
| HN=C(CH₂Cl)- | H | Cl | Cl | $NO_2$ | H | Cl | H | H |
| HN=C(CH₃)-(4-Cl-phenyl) | H | Cl | H | $NO_2$ | H | Cl | H | H |
| H | H | Cl | H | $NO_2$ | H | Cl | H | H |
| H | H | Cl | Cl | $NO_2$ | H | Cl | H | H |
| (CH₃)₂N-CH₂CH₂CH₂- | —$CH_3$ | —$CH_3$ | $NO_2$ | H | $NO_2$ | H | H | H |
| —$CH_3$ | —$CH_3$ | Cl | H | $NO_2$ | H | H | H | H |
| H | H | H | H | $NO_2$ | H | Cl | H | H |

-continued

| R¹ | R² | R³ | R⁴ | R⁵ | R⁶ | R⁷ | R⁸ | R⁹ |
|---|---|---|---|---|---|---|---|---|
| 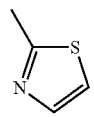 | H | H | H | NO₂ | H | H | H | H |
| 3,5-dichlorophenyl | H | Cl | Cl | NO₂ | H | Cl | H | H |
| 3-chloro,4-fluoro phenyl | H | Cl | Cl | NO₂ | H | Cl | H | H |
| CH₃ | CH₃ | H | H | NO₂ | CN | H | H | H |
| CH₃CH₂ | CH₃CH₂ | H | H | NO₂ | CN | H | H | H |
| Cyclohexyl | H | H | H | NO₂ | H | H | H | H |
| CH₃ | CH₃ | H | H | NO₂ | H | H | H | H |
| CH₃ | H | H | H | NO₂ | H | H | H | H |
| NH₂ | H | H | H | NO₂ | H | H | H | H |
| NH₂ | H | Cl | H | NO₂ | H | H | H | H |
| NH₂ | H | Cl | H | NO₂ | H | Cl | H | H |
| CH₃CH₂ | CH₃ | Cl | Cl | NO₂ | H | H | H | H |
| CH₃C=O | H | H | H | NO₂ | H | H | H | H |
| H | H | H | H | NO₂ | H | H | H | H |

In one preferred embodiment of the compounds of paragraph [0039], the compounds are of the formula (IIa):

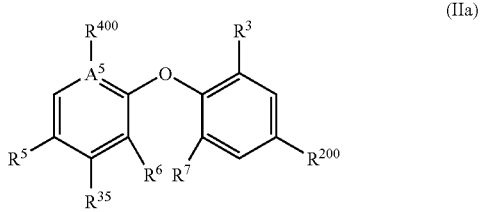

(IIa)

or pharmaceutically acceptable salts or complexes thereof, wherein $R^1$ and $R^{1a}$ are independently —H, $C_{1-6}$-hydrocarbyl, $C_5$-$C_{12}$-heterocyclyl-$C_0$-$C_6$-hydrocarbyl, aryl-$C_0$-$C_6$-hydrocarbyl, $C_5$-$C_{12}$-heteroaryl-$C_0$-$C_6$-hydrocarbyl, —C(=X)-$L^1$-$R^{10}$, $C_4$-$C_{10}$-hydrocarbyl-NH—C(O)$C_6H_4$—, aryl-oxy-$C_1$-$C_6$-hydrocarbyl-, aryl-oxy-aryl-SO₂—, $(CH_3)_2$N—$C_1$-$C_6$-hydrocarbyl, $(NH_2)(NH)C$—NH—$(CH_2)_3$—CH(NH₂CO)—, or =$C(R^{13})(R^{14})$;

X is =O, =S, or =NH;

$L^1$ is a covalent bond, —NH—, —O—, —S—, or $C_1$-$C_3$-hydrocarbyl;

$R^{10}$ is $C_1$-$C_6$-hydrocarbyl, $C_5$-$C_{12}$-heterocyclyl, aryl, or $C_5$-$C_{12}$-heteroaryl;

$R^2$ is H, $C_1$-$C_6$-hydrocarbyl, or aryl;

or $R^1$ and $R^2$ together with the nitrogen to which they are both covalently bound are a $C_0$-$C_4$-hydrocarbyl-$C_5$-$C_{12}$-hetrocyclyl;

or $R^1$ and $R^2$ together are =$C(R^{11})(R^{12})$;

$R^{11}$ is —H or —NH-aryl;

$R^{12}$ is —$N(R^{13})(R^{14})$ or —$SR^{13}$;

$R^{13}$ and $R^{14}$ and are independently selected from —H, —OH, or $C_1$-$C_3$-hydrocarbyl;

$R^3$ is —H, halo, —NO₂, NO, —NH₂, —NH—C(O)$R^{17}$, —CN, $C_1$-$C_5$-hydrocarbyl-C(O)—, or $C_1$-$C_6$-hydrocarbyl;

$R^{400}$ is —H, halo, —$N(R^{18})_2$, —NO₂, NO, —C(O)N$(R^{18})_2$, $C_1$-$C_6$-hydrocarbyl, $C_1$-$C_3$-hydrocarbyl-C(O)—NH—, mono- to per-halogenated —$C_1$-$C_6$-hydrocarbyl, or —CN;

$R^5$ and $R^{35}$ independently are —H, —NO₂, NO, —NH₂, —NH—C(O)$R^{17}$, —$C_1$-$C_3$-hydrocarbyl, mono- to per-halogenated —$C_1$-$C_3$-hydrocarbyl, $N(R^1)(R^2)SO_2$—, aryl-SO₂—NH—, aryl-oxy-aryl-SO₂—NH—, aryl-NH—SO₂—, or aryl-CO—NH—;

$R^6$ is —H, halo, —CN, —$C_1$-$C_6$-hydrocarbyl, mono- to per-halogenated —$C_1$-$C_6$-hydrocarbyl, —SO₂—, —NO₂, —NO, —NH₂, or —NH—C(O)$R^{17}$;

$R^{17}$ is —H or —$C_1$-$C_6$-hydrocarbyl;

$R^{200}$ is —$S(O)_2$—$N(R^1)(R^2)$, —$N(R^{1a})S(O)_2R^1$, —NHC(O)$R^1$, or NHC(O)NHR¹;

$R^7$ is —H, halo, —OH, $C_{1-3}$-hydrocarbyl-O—, mono- to per-halogenated —$C_1$-$C_3$-hydrocarbyl-O—, —$C_1$-$C_3$-hydrocarbyl, mono- to per-halogenated —$C_1$-$C_3$-hydrocarbyl-, —CN, —SO₂, —NO₂, —NO, —NH₂, or —NH—C(O)$R^{17}$;

$R^{18}$ is —H, $C_1$-$C_6$-hydrocarbyl, —C(O)$R^{19}$, —$SO_2R^{19}$, C(O)NHR¹⁹, CSNHR¹⁹, CNNHR¹⁹, or CO₂R¹⁹;

$R^{19}$ is —H, —OH, or $C_1$-$C_3$-hydrocarbyl;

$A^5$ is nitrogen or carbon with the proviso that when $A^5$ is nitrogen, then the substituent bonded to that position is absent;

wherein each of the aryl, heteroaryl, heterocyclyl, and hydrocarbyl groups above is optionally substituted by one or more groups selected from halo, —OH, —NH₂, $C_1$-$C_6$-hydrocarbyl-C(O)—, OXO, $C_1$-$C_6$-hydrocarbyl-(O)—, mono- to per-halogenated $C_1$-$C_6$-hydrocarbyl-O—, $C_1$-$C_6$-hydrocarbyl, mono- to per-halogenated $C_1$-$C_6$-hydrocarbyl, —CN, —NO₂, —NO, —NH₂, —NH—C(O)$R^{18}$, or —SO₂.

In a preferred embodiment of the compounds of paragraph [0040], $A^5$ is carbon and $R^{200}$ is —$S(O)_2$—$N(R^1)(R^2)$.

In a preferred embodiment of the compounds of paragraph [0041], $R^1$ is hydrogen and $R^2$ is phenyl, wherein phenyl is optionally substituted with halogen and/or trifluoromethoxy.

In a preferred embodiment of the compounds of paragraph [0042], $R^{35}$ and $R^6$ are both hydrogen, $R^5$ is —NO₂, and $R^3$, $R^7$ and $R^{400}$ are each halogen.

In another preferred embodiment of the compounds of paragraph [0040], $A^5$ is nitrogen and $R^{200}$ is —$N(R^{1a})S(O)_2R^1$.

In a preferred embodiment of the compounds of paragraph [0044], $R^{1a}$ is hydrogen and $R^1$ is phenyl, wherein phenyl is optionally substituted with halogen and/or trifluoromethyl.

In a preferred embodiment of the compounds of paragraph [0045], $R^3$ and $R^7$ are both hydrogen, and $R^5$, $R^6$, and $R^{35}$ are independently selected from hydrogen, halogen, and trifluoromethyl.

In another preferred embodiment of the compounds of paragraph [0040], $A^5$ is carbon and $R^{200}$ is —NHC(O)$R^1$.

In a preferred embodiment of the compounds of paragraph [0047], $R^1$ is phenyl optionally substituted with halogen.

In a preferred embodiment of the compounds of paragraph [0048], $R^{400}$, $R^{35}$, $R^6$, and $R^7$ are each hydrogen, and $R^3$ and $R^5$ are independently halogen.

In another preferred embodiment of the compounds of paragraph [0040], $A^5$ is carbon and $R^{200}$ is NHC(O)NH$R^1$.

In a preferred embodiment of the compounds of paragraph [0050], $R^1$ is phenyl optionally substituted with halogen.

In a preferred embodiment of the compounds of paragraph [0051], $R^{400}$, $R^{35}$, $R^6$, and $R^7$ are each hydrogen, and $R^3$ and $R^5$ are independently halogen.

In another preferred embodiment of the compounds of paragraph [0039], the compounds are of the formula (IIb):

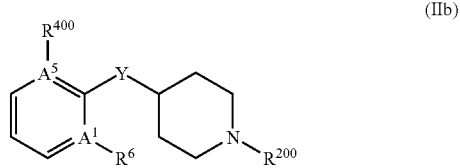

(IIb)

and pharmaceutically acceptable salts and complexes thereof, wherein $R^6$ is —H, halo, —N($R^{18}$)$_2$, —NO$_2$, NO, —C(O)N($R^{18}$)$_2$, $C_1$-$C_6$-hydrocarbyl, $C_1$-$C_3$-hydrocarbyl-C(O)—NH—, mono- to per-halogenated —$C_1$-$C_6$-hydrocarbyl, or —CN $R^{400}$ independently are —H, halo, —CN, —$C_1$-$C_6$-hydrocarbyl, mono- to per-halogenated —$C_1$-$C_6$-hydrocarbyl, —SO$_2$, —NO$_2$, —NO, —NH$_2$, or —NH—C(O)$R^{17}$;

$R^{17}$ is —H or $C_1$-$C_6$-hydrocarbyl;

$R^{200}$ is —S(O)$_2$$R^{25}$ or —C(O)NH$R^{25}$;

$R^{25}$ is $C_5$-$C_{12}$-heterocyclyl, aryl, or $C_5$-$C_{12}$-heteroaryl;

Y is —O—, —S—, —S(O)—, —SO$_2$—, —C(O)—, or —N$R^{18}$;

$R^{18}$ is —H, $C_1$-$C_6$-hydrocarbyl, —C(O)$R^{19}$, —SO$_2$$R^{19}$, C(O)NH$R^{19}$, CSNH$R^{19}$, CNNH$R^{19}$, or CO$_2$$R^{19}$;

$R^{19}$ is —H, —OH, or $C_1$-$C_3$-hydrocarbyl; and $A^1$ and $A^5$ are independently nitrogen or carbon with the proviso that when any one of $A^1$ or $A^5$ is nitrogen, then the substituent bonded to that position is absent;

wherein each of the aryl, heteroaryl, heterocyclyl, and hydrocarbyl groups above is optionally substituted by one or more groups selected from halo, —OH, —NH$_2$, $C_1$-$C_6$-hydrocarbyl-C(O)—, oxo, $C_1$-$C_6$-hydrocarbyl-(O)—, mono- to per-halogenated $C_1$-$C_6$-hydrocarbyl-, $C_1$-$C_6$-hydrocarbyl, mono- to per-halogenated $C_1$-$C_6$-hydrocarbyl, —CN, —NO$_2$, —NO, —NH$_2$, —NH—C(O)$R^{18}$, or —SO$_2$.

In one preferred embodiment of the compounds according to paragraph [0053], $A^1$ and $A^5$ are both carbon.

In another preferred embodiment of the compounds according to paragraph [0053], $A^1$ and $A^5$ are both nitrogen.

In a preferred embodiment of the compounds according to paragraph [0054], $R^6$ and $R^{400}$ are independently H, halo, —CN, mono- to per-halogenated —$C_1$-$C_6$-hydrocarbyl, or —NH$_2$.

In a preferred embodiment of the compounds according to paragraph [0056], $R^6$ and $R^{400}$ are independently H, halo, or —CF$_3$.

In a preferred embodiment of the compounds according to paragraph [0057], $R^6$ and $R^{400}$ are independently H or —CF$_3$.

In one preferred embodiment of the compounds according to any of paragraphs [0053] to [0058], Y is oxygen.

In one preferred embodiment of the compounds according to any of paragraphs [0053] to [0054] and [0056] to [0059], $R^{200}$ is —S(O)$_2$$R^{25}$.

In a preferred embodiment of the compounds according to paragraph [0060], $R^{25}$ is aryl, optionally substituted as indicated in paragraph [0053].

In a preferred embodiment of the compounds according to paragraph [0061], $R^{25}$ is phenyl, optionally substituted as indicated in paragraph [0053].

In a preferred embodiment of the compounds according to paragraph [0062], $R^{25}$ is phenyl, optionally substituted with halo and/or —CF$_3$.

In one preferred embodiment of the compounds according to any of paragraphs [0053] to [0059], $R^{200}$ is —C(O)NH$R^{25}$.

In a preferred embodiment of the compounds according to paragraph [0064], $R^{25}$ is aryl, optionally substituted as indicated in paragraph [0053].

In a preferred embodiment of the compounds according to paragraph [0065], $R^{25}$ is phenyl, optionally substituted as indicated in paragraph [0053].

In a preferred embodiment of the compounds according to paragraph [0066], $R^{25}$ is phenyl, optionally substituted with halo and/or —CF$_3$.

The invention also provides for a pharmaceutical composition comprising a compound according to the invention together with a pharmaceutically acceptable carrier or excipient. The invention also provides for methods of inhibiting ubiquitination in a cell comprising contacting a cell in which inhibition of ubiquitination is desired with a compound according to the invention.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. CH$_3$—CH$_2$—), in certain circumstances a bivalent linking moiety can be "alkyl," in which case those skilled in the art will understand the alkyl to be a divalent radical (e.g., CH$_2$—CH$_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as (A)$_a$-B-, wherein a is 0 or 1. In such instances, when a is 0 the moiety is B- and when a is 1 the moiety is A-B-. Also, a number of moieties disclosed herein exist in multiple tautomeric forms, all of which are intended to be encompassed by any given tautomeric structure. Other stereochemical forms of the compounds of the invention are also encompassed including but not limited to enantiomers, diastereomers, and other isomers such as rotamers.

For simplicity, when a substituent can be of a particular chemical class differing by the number of atoms or groups of the same kind in the moiety (e.g., alky, which can be $C_1$, $C_2$, $C_3$, etc.), the number of repeated atoms or groups is represented by a range (e.g., $C_1$-$C_6$-alkyl). In such instances each and every number in that range and all sub-ranges are specifically contemplated. Thus, $C_1$-$C_3$-alkyl means $C_1$-, $C_2$-, $C_3$-, $C_{1-2}$, $C_{1-3}$-, and $C_{2-3}$-alkyl.

In addition to individual preferred embodiments of each substituent defined herein, the invention also comprises all combinations of preferred substituents.

The term "alkyl" as employed herein refers to straight and branched chain aliphatic groups having from 1 to 12 carbon atoms, preferably 1-8 carbon atoms, more preferably 1-6 carbon atoms, which is optionally substituted with one, two or three substituents. Unless otherwise specified, the alkyl group may be saturated, unsaturated, or partially unsaturated. As used herein, therefore, the term "alkyl" is specifically intended to include alkenyl and alkynyl groups, as well as saturated alkyl groups, unless expressly stated otherwise. Preferred alkyl groups include, without limitation, methyl, ethyl, propyl, isopropyl, butyl, tertbutyl, isobutyl, pentyl, hexyl, vinyl, allyl, isobutenyl, ethynyl, and propynyl.

As employed herein, a "substituted" alkyl, cycloalkyl, aryl, or heterocyclic group is one having between one and about four, preferably between one and about three, more preferably one or two, non-hydrogen substituents. Suitable substituents include, without limitation, halo, hydroxy, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The term "cycloalkyl" as employed herein includes saturated and partially unsaturated cyclic hydrocarbon groups having 3 to 12, preferably 3 to 8 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "hydrocarbyl" as employed herein includes all alkyl moieties and all cycloalkyl moieties (both as defined above), each alone or in combination. Thus, for example, hydrocarbyl includes methyl, ethyl, propyl, n-butyl, i-butyl, cyclopropyl, cyclohexyl, cyclopropyl-$CH_2$—, cyclohexyl-$(CH_2)_3$—, etc.

An "aryl" group is a $C_6$-$C_{14}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $C_1$-$C_6$-alkyl-($C_6$-$C_{10}$)aryl, including, without limitation, benzyl, phenethyl, and naphthylmethyl. An "alkaryl" or "alkylaryl" group is an aryl group having one or more alkyl substituents. Examples of alkaryl groups include, without limitation, tolyl, xylyl, mesityl, ethylphenyl, tert-butylphenyl, and methylnaphthyl.

A "heterocyclic" group (or "heterocyclyl") is a non-aromatic mono-, bi-, or tricyclic structure having from about 3 to about 14 atoms, wherein one or more atoms are selected from the group consisting of N, O, and S. One ring of a bicyclic heterocycle or two rings of a tricyclic heterocycle may be aromatic, as in indan and 9,10-dihydro-anthracene. The heterocyclic group is optionally substituted on carbon with oxo or with one of the substituents listed above. The heterocyclic group may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino.

In certain preferred embodiments, the heterocyclic group is a heteroaryl group. As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, between one and about three heteroatoms selected from the group consisting of N, O, and S. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

In certain other preferred embodiments, the heterocyclic group is fused to an aryl or heteroaryl group. Examples of such fused heterocycles include, without limitation, tetrahydroquinolinyl and dihydrobenzofuranyl.

Additional preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, 1H-indazolyl, indolenyl, indolinyl, indolizinyl, 3H-indolyl, isobenzofuranyl, isochromanyl, isoindazolyl, isoindolinyl, isoindolyl, isothiazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazolidinyl, pyrazolinyl, pyridazinyl, pyridooxazole, pyridoimidazole, pyridothiazole, pyridinyl, pyrrolidinyl, pyrrolinyl, 2H-pyrrolyl, quinazolinyl, 4H-quinolizinyl, quinuclidinyl, tetrahydroisoquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A moiety that is substituted is one in which one or more hydrogens have been independently replaced with another chemical substituent. As a nonlimiting example, substituted phenyls include 2-fluorphenyl, 3,4-dichlorophenyl, 3-chloro-4-fluoro-phenyl, 2-fluor-3-propylphenyl. As another nonlimiting example, substituted n-octyls include 2,4 dimethyl-5-ethyl-octyl and 3-cyclopentyl-octyl. Included within this definition are methylenes (—$CH_2$—) substituted with oxygen to form carbonyl —CO—).

Unless otherwise stated, as employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above; and (c) —$(CH_2)_s$—$NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$-$C_8$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents from (a), above.

The term "halogen" or "halo" as employed herein refers to chlorine, bromine, fluorine, or iodine As herein employed, the term "acyl" refers to an alkylcarbonyl or arylcarbonyl substituent.

The term "acylamino" refers to an amide group attached at the nitrogen atom. The term "carbamoyl" refers to an amide group attached at the carbonyl carbon atom. The nitrogen atom of an acylamino or carbamoyl substituent may be additionally substituted. The term "sulfonamido" refers to a sulfonamide substituent attached by either the sulfur or the nitrogen atom. The term "amino" is meant to include $NH_2$, alkylamino, arylamino, and cyclic amino groups.

The compounds in the table immediately below were prepared essentially using the methods described herein and illustrated below in the schemes. All of the compounds in this application were named using Chemdraw Ultra version 6.0.2, which is available through Cambridgesoft.co, 100 Cambridge Park Drive, Cambridge, Mass. 02140, Namepro version 5.09, which is available from ACD labs, 90 Adelaide Street West, Toronto, Ontario, M5H, 3V9, Canada, or were derived therefrom.

| Example | Structure | Names |
|---|---|---|
| 1 | 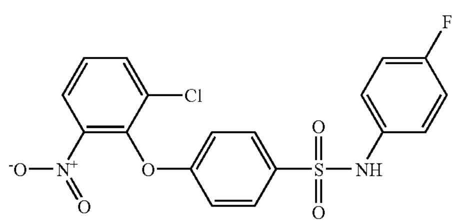 | 4-(2-chloro-6-nitrophenoxy)-N-(4-fluorophenyl)benzenesulfonamide |
| 2 | 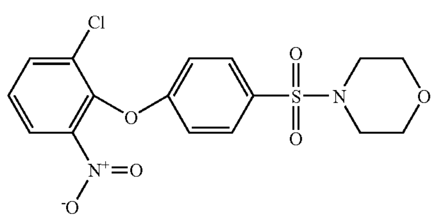 | 4-{[4-(2-chloro-6-nitrophenoxy)phenyl]sulfonyl}morpholine |
| 3 | 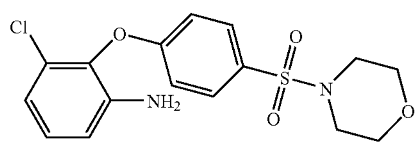 | {3-chloro-2-[4-(morpholin-4-ylsulfonyl)phenoxy]phenyl}amine |
| 4 | 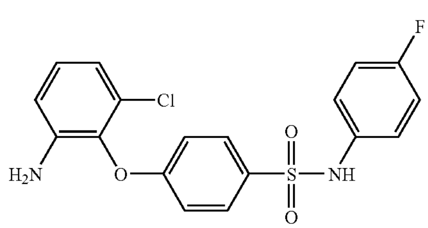 | 4-(2-amino-6-chlorophenoxy)-N-(4-fluorophenyl)benzenesulfonamide |

-continued

| Example | Structure | Names |
|---|---|---|
| 5 | 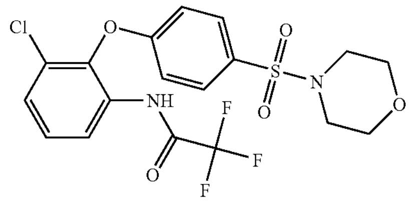 | N-{3-chloro-2-[4-(morpholin-4-ylsulfonyl)phenoxy]phenyl}-2,2,2-trifluoroacetamide |
| 6 | 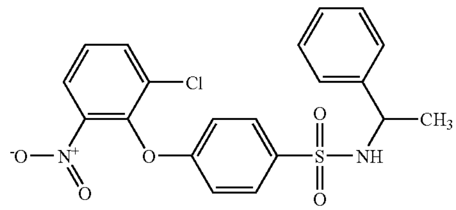 | 4-(2-chloro-6-nitrophenoxy)-N-(1-phenyl-ethyl)benzenesulfonamide |
| 7 | 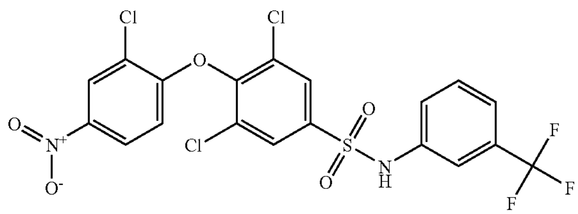 | 3,5-dichloro-4-(2-chloro-4-nitrophenoxy)-N-[3-(trifluoromethyl)phenyl]benzene-sulfonamide |
| 8 | 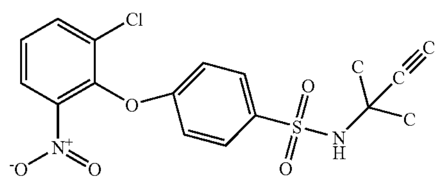 | 4-(2-chloro-6-nitrophenoxy)-N-(1,1-di-methylpropyl)benzenesulfonamide |
| 9 | 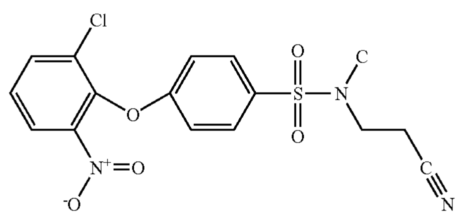 | N-(3-aminopropyl)-4-(2-chloro-6-nitro-phenoxy)-N-methylbenzenesulfonamide |
| 10 | 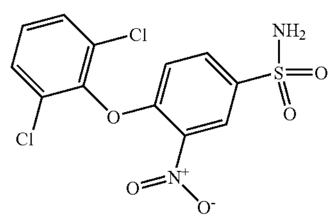 | 4-(2,6-dichlorophenoxy)-3-nitrobenzene sulfonamide |
| 11 | 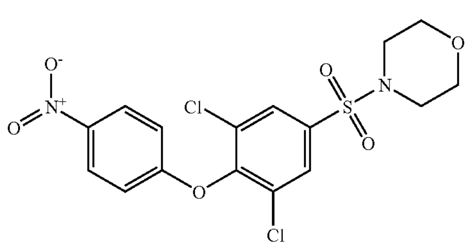 | 4-{[3,5-dichloro-4-(4-nitrophenoxy)phenyl]sulfonyl}morpholine |

-continued

| Example | Structure | Names |
|---|---|---|
| 12 | 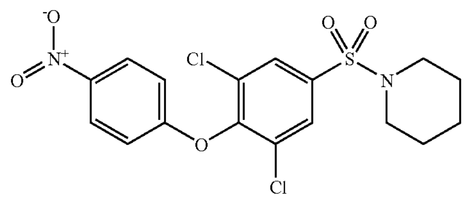 | 1-{[3,5-dichloro-4-(4-nitrophenoxy)phenyl]sulfonyl}piperidine |
| 13 | 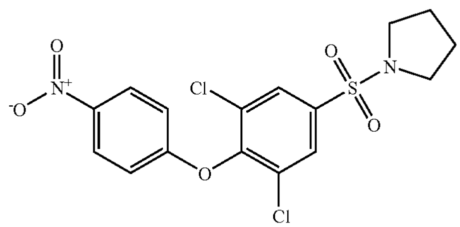 | 1-{[3,5-dichloro-4-(4-nitrophenoxy)phenyl]sulfonyl}pyrrolidine |
| 14 | 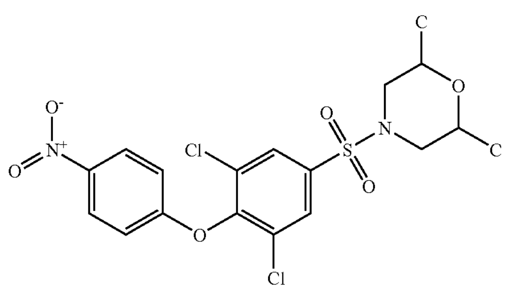 | 4-{[3,5-dichloro-4-(4-nitrophenoxy)phenyl]sulfonyl}-2,6-dimethylmorpholine |
| 15 | 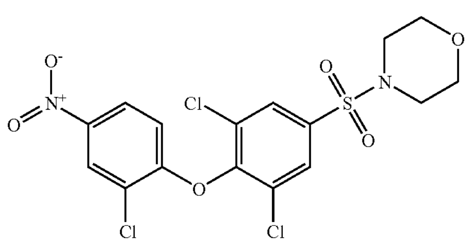 | 4-{[3,5-dichloro-4-(2-chloro-4-nitrophenoxy)phenyl]sulfonyl}morpholine |
| 16 | 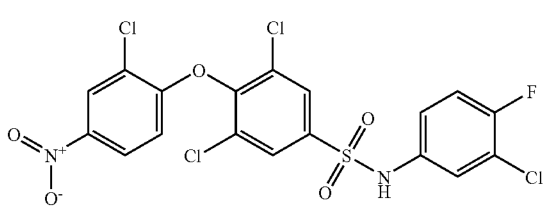 | 3,5-dichloro-N-(3-chloro-4-fluorophenyl)-4-(2-chloro-4-nitrophenoxy)benzenesulfonamide |
| 17 | 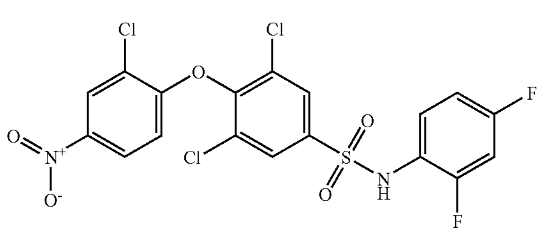 | 3,5-dichloro-4-(2-chloro-4-nitrophenoxy)-N-(2,4-difluorophenyl)benzenesulfonamide |

-continued

| Example | Structure | Names |
|---|---|---|
| 18 | 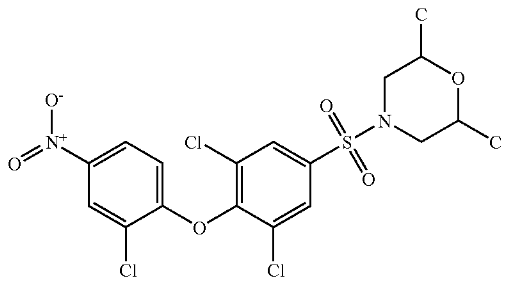 | 4-{[3,5-dichloro-4-(2-chloro-4-nitrophenoxy)phenyl]sulfonyl}-2,6-dimethylmorpholine |
| 19 | 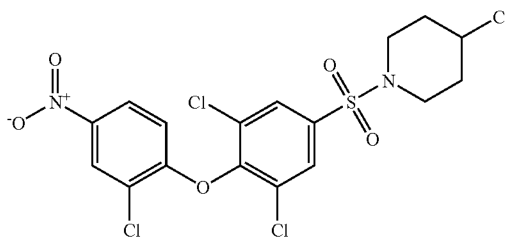 | 1-{[3,5-dichloro-4-(2-chloro-4-nitrophenoxy)phenyl]sulfonyl}-4-methylpiperidine |
| 20 | 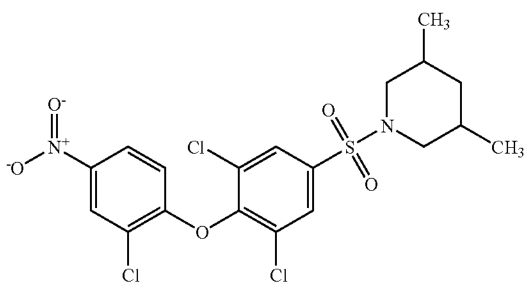 | 1-{[3,5-dichloro-4-(2-chloro-4-nitrophenoxy)phenyl]sulfonyl}-3,5-dimethylpiperidine |
| 21 | 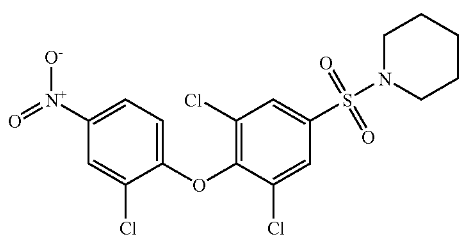 | 1-{[3,5-dichloro-4-(2-chloro-4-nitrophenoxy)phenyl]sulfonyl}piperidine |
| 22 | 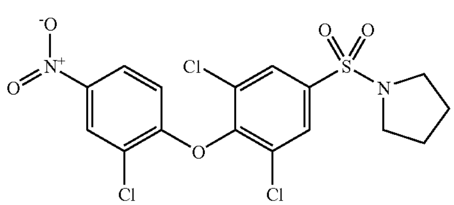 | 1-{[3,5-dichloro-4-(2-chloro-4-nitrophenoxy)phenyl]sulfonyl}pyrrolidine |
| 23 | 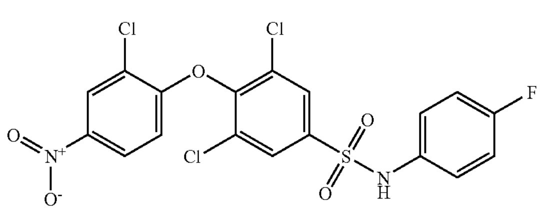 | 3,5-dichloro-4-(2-chloro-4-nitrophenoxy)-N-(4-fluorophenyl)benzenesulfonamide |

| Example | Structure | Names |
| --- | --- | --- |
| 24 | 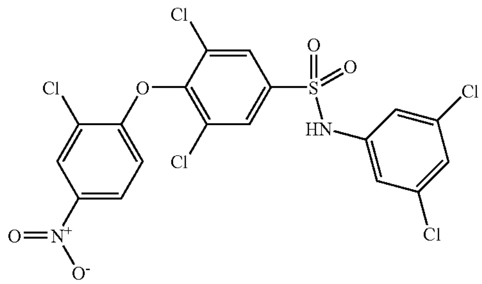 | 3,5-dichloro-4-(2-chloro-4-nitrophenoxy)-N-(3,5-dichlorophenyl)benzenesulfonamide |
| 25 | 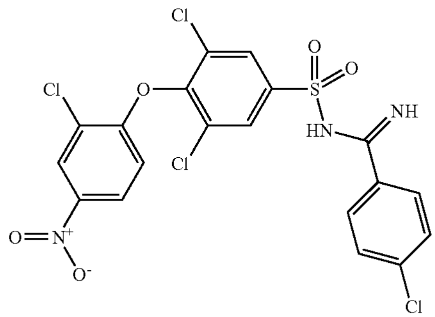 | 4-chloro-N-{[3,5-dichloro-4-(2-chloro-4-nitrophenoxy)phenyl]sulfonyl}benzene-carboximidamide |
| 26 | 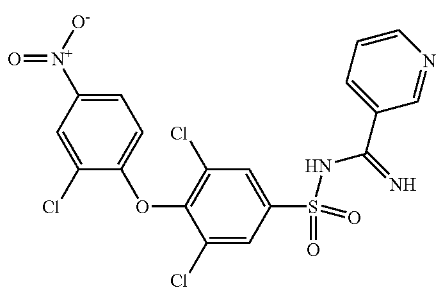 | N-{[3,5-dichloro-4-(2-chloro-4-nitrophenoxy)phenyl]sulfonyl}pyridine-3-carboximidamide |
| 27 | 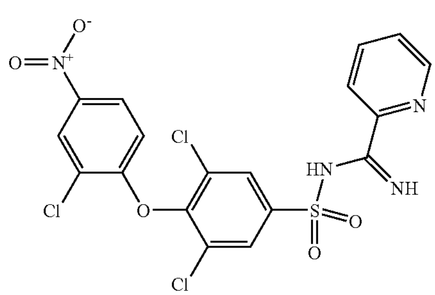 | N-{[3,5-dichloro-4-(2-chloro-4-nitrophenoxy)phenyl]sulfonyl}pyridine-2-carboximidamide |
| 28 | 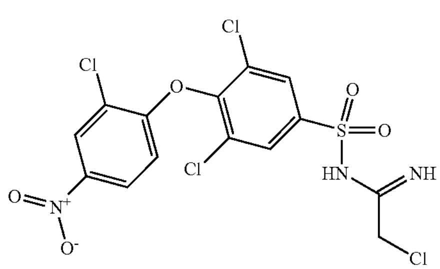 | 2-chloro-N-{[3,5-dichloro-4-(2-chloro-4-nitrophenoxy)phenyl]sulfonyl}ethanimidamide |

| Example | Structure | Names |
|---|---|---|
| 29 | 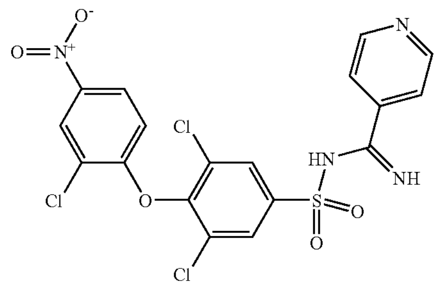 | N-{[3,5-dichloro-4-(2-chloro-4-nitrophenoxy)phenyl]sulfonyl}pyridine-4-carboximidamide |
| 30 | 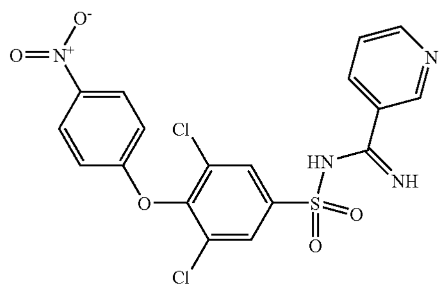 | N-{[3,5-dichloro-4-(4-nitrophenoxy)phenyl]sulfonyl}pyridine-3-carboximidamide |
| 31 | 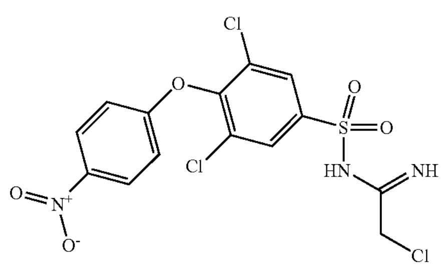 | 2-chloro-N-{[3,5-dichloro-4-(4-nitrophenoxy)phenyl]sulfonyl}ethanimidamide |
| 32 | 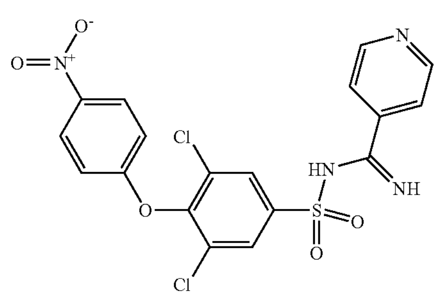 | N-{[3,5-dichloro-4-(4-nitrophenoxy)phenyl]sulfonyl}pyridine-4-carboximidamide |
| 33 | 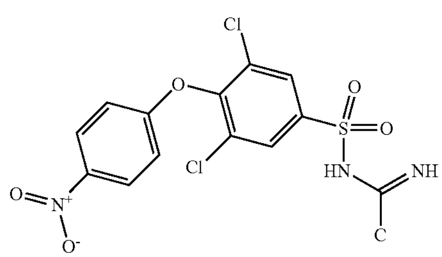 | N-{[3,5-dichloro-4-(4-nitrophenoxy)phenyl]sulfonyl}ethanimidamide |

| Example | Structure | Names |
|---|---|---|
| 34 | 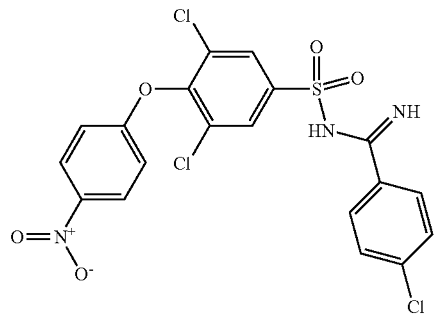 | 4-chloro-N-{[3,5-dichloro4-(4-nitrophenoxy)phenyl]sulfonyl}benzenecarboximidamide |
| 35 | 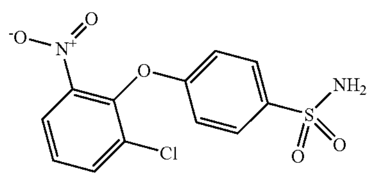 | 4-(2-chloro-6-nitrophenoxy)benzenesulfonamide |
| 36 | 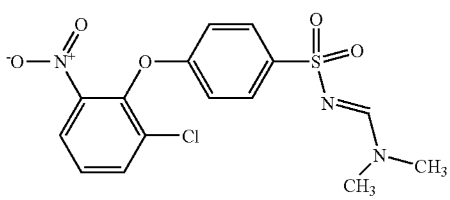 | 4-(2-chloro-6-nitrophenoxy)-N-[(1E)-(dimethylamino)methylene]benzenesulfonamide |
| 37 | 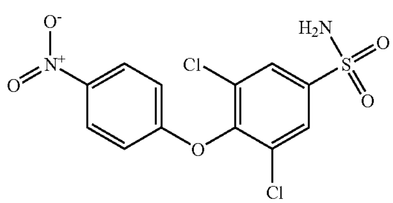 | 3,5-dichloro-4-(4-nitrophenoxy)benzenesulfonamide |
| 38 | 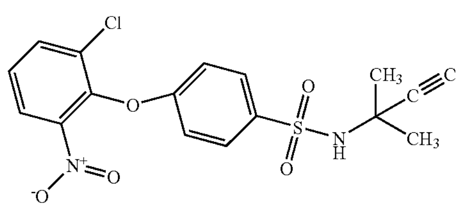 | 4-(2-chloro-6-nitrophenoxy)-N-(1,1-dimethylpropyl)benzenesulfonamide |
| 39 | 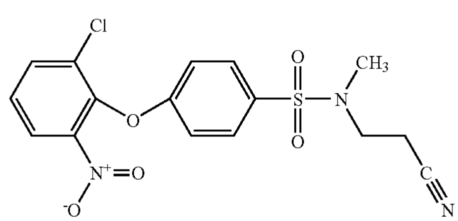 | N-(3-aminopropyl)-4-(2-chloro-6-nitrophenoxy)-N-methylbenzenesulfonamide |
| 40 | 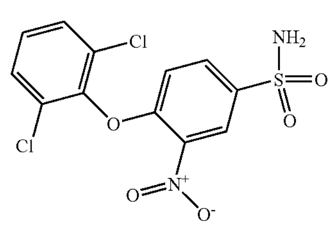 | 4-(2,6-dichlorophenoxy)-3-nitrobenzenesulfonamide |

| Example | Structure | Names |
|---|---|---|
| 41 | 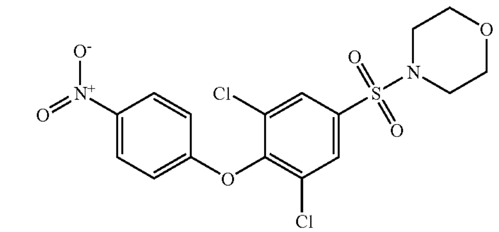 | 4-{[3,5-dichloro-4-(4-nitrophenoxy)phenyl]sulfonyl}morpholine |
| 42 | 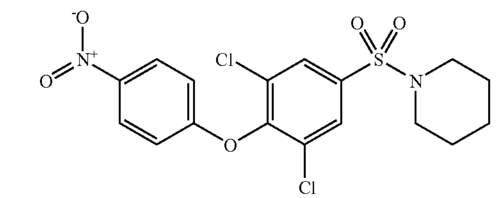 | 1-{[3,5-dichloro-4-(4-nitrophenoxy)phenyl]sulfonyl}piperidine |
| 43 | 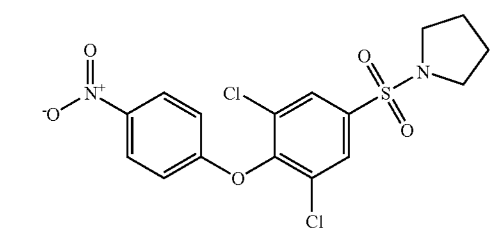 | 1-{[3,5-dichloro-4-(4-nitrophenoxy)phenyl]sulfonyl}pyrrolidine |
| 44 | 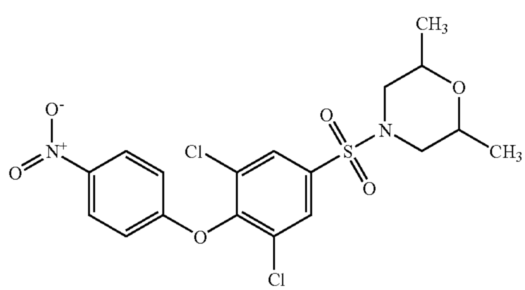 | 4-{[3,5-dichloro-4-(4-nitrophenoxy)phenyl]sulfonyl}-2,6-dimethylmorpholine |
| 45 | 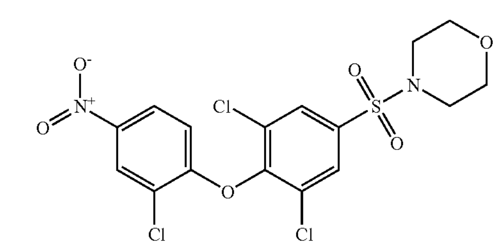 | 4-{[3,5-dichloro-4-(2-chloro-4-nitrophenoxy)phenyl]sulfonyl}morpholine |
| 46 | 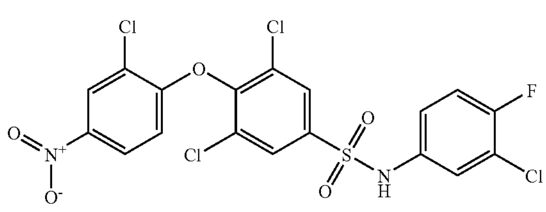 | 3,5-dichloro-N-(3-chloro-4-fluorophenyl)-4-(2-chloro-4-nitrophenoxy)benzenesulfonamide |

-continued

| Example | Structure | Names |
|---|---|---|
| 47 | 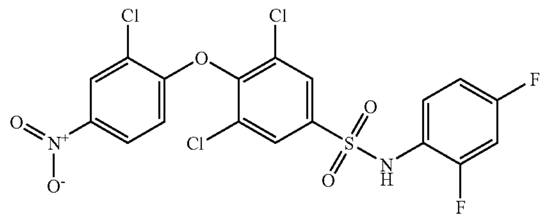 | 3,5-dichloro-4-(2-chloro-4-nitrophenoxy)-N-(2,4-difluorophenyl)benzenesulfonamide |
| 48 | 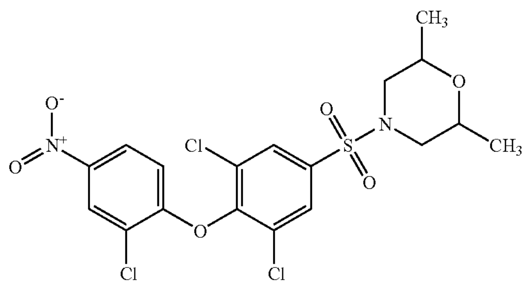 | 4-{[3,5-dichloro-4-(2-chloro-4-nitrophenoxy)phenyl]sulfonyl}-2,6-dimethylmorpholine |
| 49 | 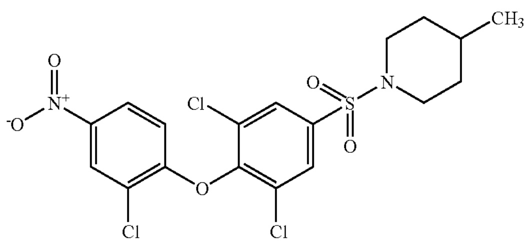 | 4-{[3,5-dichloro-4-(2-chloro-4-nitrophenoxy)phenyl]sulfonyl}-4-methylpiperidine |
| 50 | 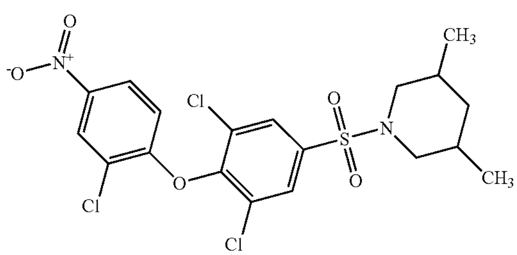 | 1-{[3,5-dichloro-4-(2-chloro-4-nitrophenoxy)phenyl]sulfonyl}-3,5-dimethylpiperidine |
| 51 | 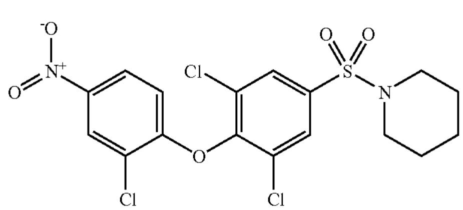 | 1-{[3,5-dichloro-4-(2-chloro-4-nitrophenoxy)phenyl]sulfonyl}piperidine |
| 52 | 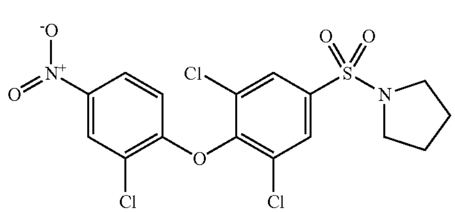 | 1-{[3,5-dichloro-4-(2-chloro-4-nitrophenoxy)phenyl]sulfonyl}pyrrolidine |

| Example | Structure | Names |
|---|---|---|
| 53 | 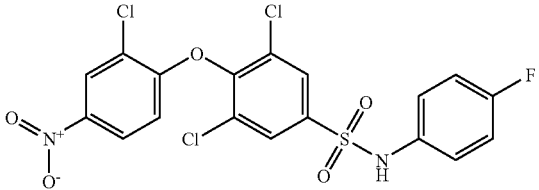 | 3,5-dichloro-4-(2-chloro-4-nitrophenoxy)-N-(4-fluorophenyl)benzenesulfonamide |
| 54 | 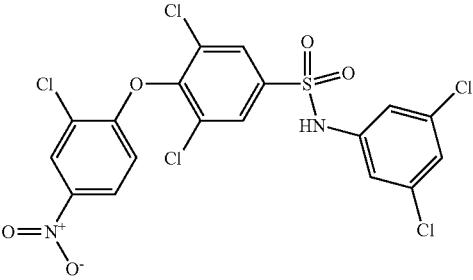 | 3,5-dichloro-4-(2-chloro-4-nitrophenoxy)-N-(3,5-dichlorophenyl)benzenesulfonamide |
| 55 | 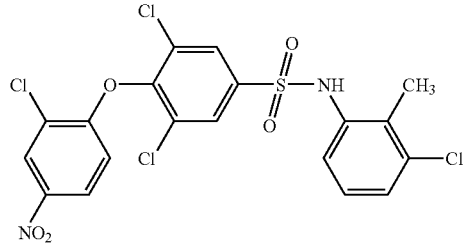 | 3,5-dichloro-N-(3-chloro-2-methylphenyl)-4-(2-chloro-4-nitrophenoxy)benzene-sulfonamide |
| 56 | 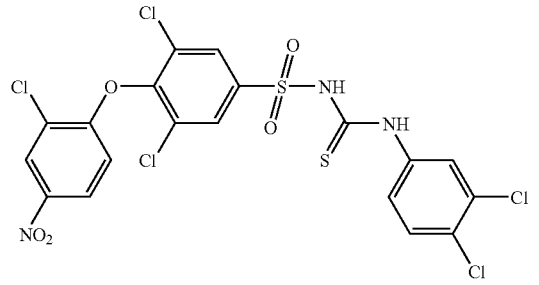 | 3,5-dichloro-4-(2-chloro-4-nitrophenoxy)-N-{[(3,4-dichlorophenyl)amino]carbono-thioyl}benzenesulfonamide |
| 57 | 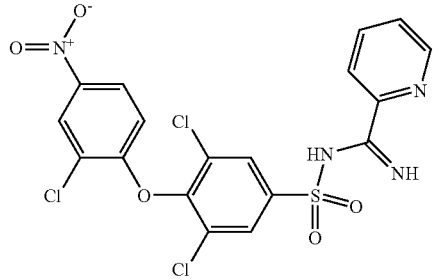 | N-{[3,5-dichloro-4-(2-chloro-4-nitrophenoxy)phenyl]sulfonyl}pyridine-2-carboximidamide |
| 58 | 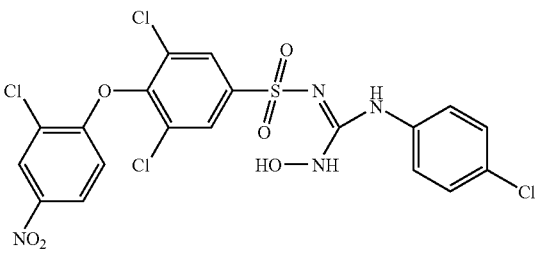 | 3,5-dichloro-4-(2-chloro-4-nitrophenoxy)-N-[(1Z)-[(4-chlorophenyl)amino](hydroxy-amino)methylene]benzenesulfonamide |

| Example | Structure | Names |
|---|---|---|
| 59 | 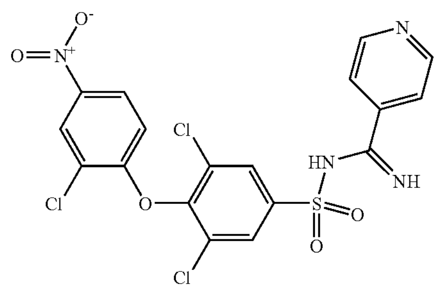 | N-{[3,5-dichloro-4-(2-chloro-4-nitrophenoxy)phenyl]sulfonyl}pyridine-4-carboximidamide |
| 60 | 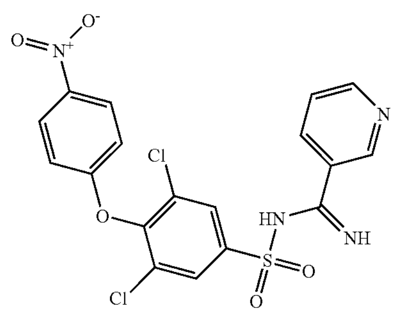 | N-{[3,5-dichloro-4-(4-nitrophenoxy)phenyl]sulfonyl}pyridine-3-carboximidamide |
| 61 | 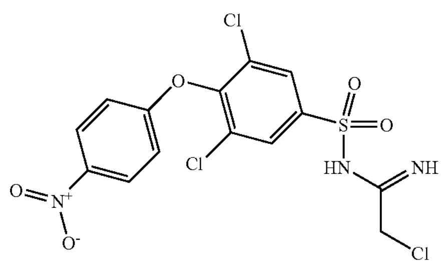 | 2-chloro-N-{[3,5-dichloro-4-(4-nitrophenoxy)phenyl]sulfonyl}ethanimidamide |
| 62 | 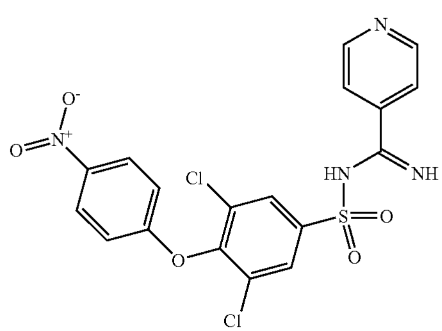 | N-{[3,5-dichloro-4-(4-nitrophenoxy)phenyl]sulfonyl}pyridine-4-carboximidamide |
| 63 | 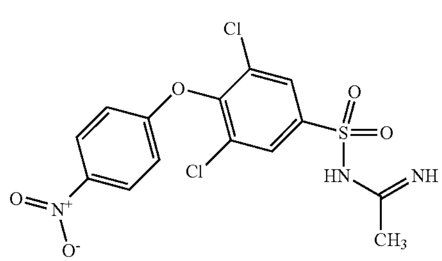 | N-{[3,5-dichloro-4-(4-nitrophenoxy)phenyl]sulfonyl}ethanimidamide |

-continued

| Example | Structure | Names |
|---|---|---|
| 64 | 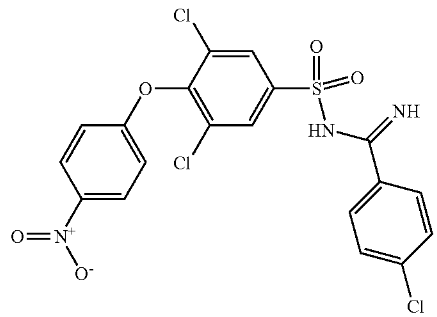 | 4-chloro-N-{[3,5-dichloro-4-(4-nitrophenoxy)phenyl]sulfonyl}benzenecarboximidamide |
| 65 | 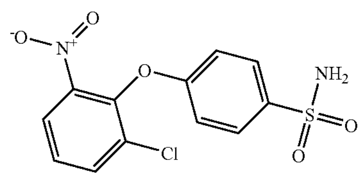 | 4-(2-chloro-6-nitrophenoxy)benzenesulfonamide |
| 66 | 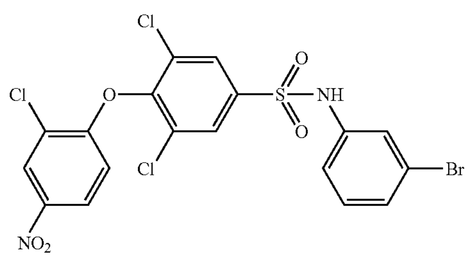 | N-(3-bromophenyl)-3,5-dichloro-4-(2-chloro-4-nitrophenoxy)benzenesulfonamide |
| 67 | 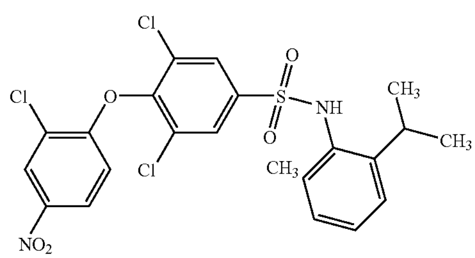 | 3,5-dichloro-4-(2-chloro-4-nitrophenoxy)-N-(2-isopropyl-6-methylphenyl)benzenesulfonamide |
| 68 | 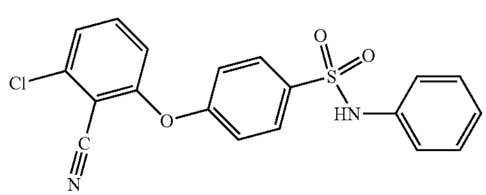 | 4-[2-(aminomethyl)-3-chlorophenoxy]-N-phenylbenzenesulfonamide |
| 69 | 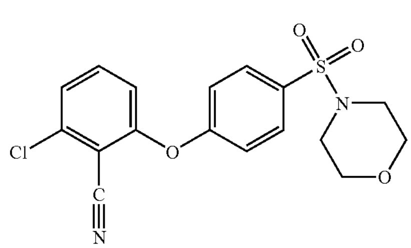 | {2-chloro-6-[4-(morpholin-4-ylsulfonyl)phenoxy]benzyl}amine |

-continued

| Example | Structure | Names |
|---|---|---|
| 70 | 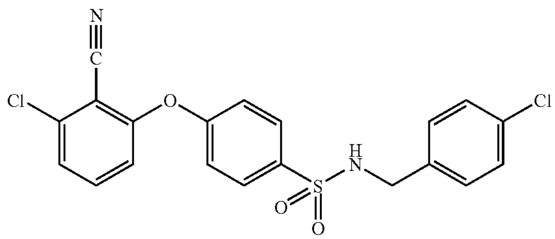 | 4-[2-(aminomethyl)-3-chlorophenoxy]-N-(4-chlorobenzyl)benzenesulfonamide |
| 71 | 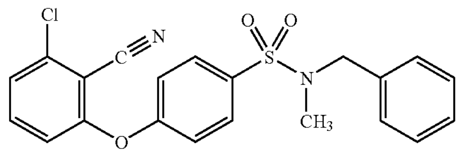 | 4-[2-(aminomethyl)-3-chlorophenoxy]-N-benzyl-N-methylbenzenesulfonamide |
| 72 | 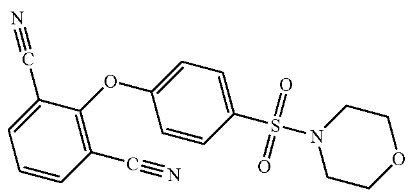 | {2-[4-(morpholin-4-ylsulfonyl)phenoxy]-1,3-phenylene}dimethanamine |
| 73 | 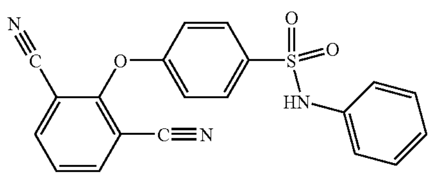 | 4-[2,6-bis(aminomethyl)phenoxy]-N-phenylbenzenesulfonamide |
| 74 | 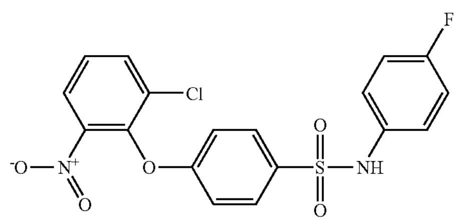 | 4-(2-chloro-6-nitrophenoxy)-N-(4-fluorophenyl)benzenesulfonamide |
| 75 | 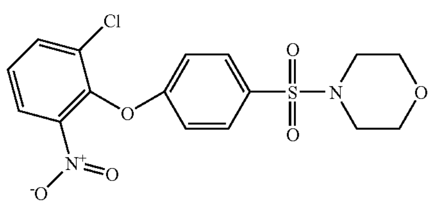 | 4-{[4-(2-chloro-6-nitrophenoxy)phenyl]sulfonyl}morpholine |
| 76 | 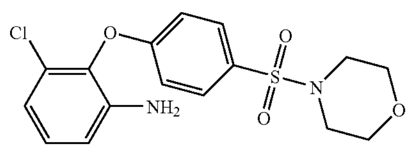 | 3-chloro-2-[4-(morpholin-4-ylsulfonyl)phenoxy]aniline |
| 77 | 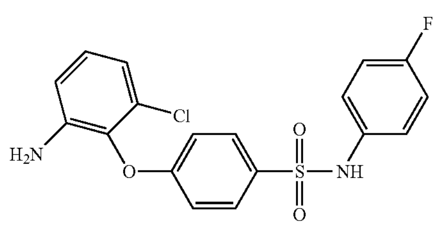 | 4-(2-amino-6-chlorophenoxy)-N-(4-fluorophenyl)benzenesulfonamide |

-continued

| Example | Structure | Names |
|---|---|---|
| 78 | 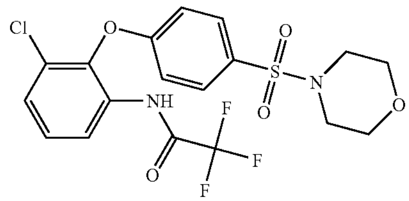 | N-{3-chloro-2-[4-(morpholin-4-ylsulfonyl)phenoxy]phenyl}-2,2,2-trifluoroacetamide |
| 79 | 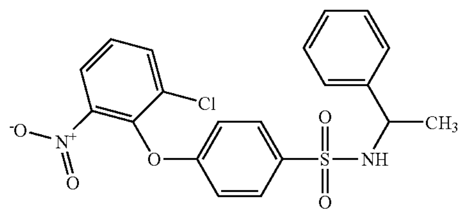 | 4-(2-chloro-6-nitrophenoxy)-N-(1-phenylethyl)benzenesulfonamide |
| 80 | 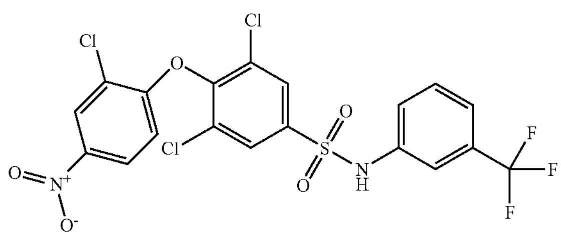 | 3,5-dichloro-4-(2-chloro-4-nitrophenoxy)-N-[3-(trifluoromethyl)phenyl]benzenesulfonamide |
| 81 | 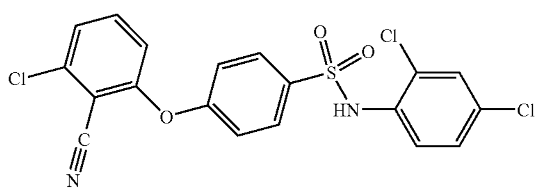 | 4-[2-(aminomethyl)-3-chlorophenoxy]-N-(2,4-dichlorophenyl)benzenesulfonamide |
| 82 | 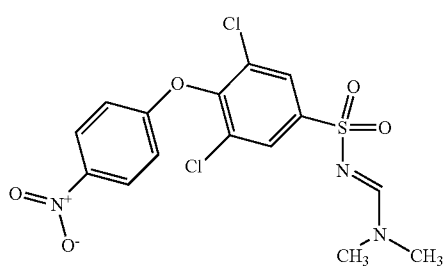 | 3,5-dichloro-N-[(1E)-(dimethylamino)methylene]-4-(4-nitrophenoxy)benzenesulfonamide |
| 83 | 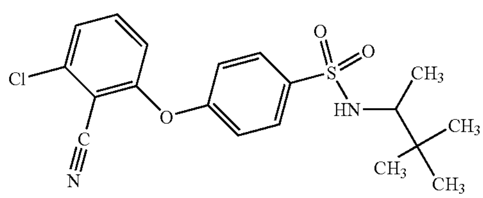 | 4-[2-(aminomethyl)-3-chlorophenoxy]-N-(1,2,2-trimethylpropyl)benzenesulfonamide |
| 84 | 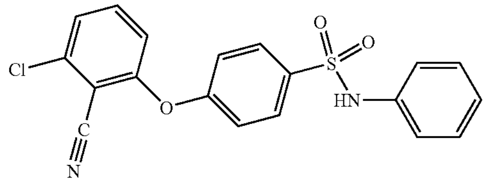 | 4-[2-(aminomethyl)-3-chlorophenoxyl-N-phenylbenzenesulfonamide |

-continued

| Example | Structure | Names |
|---------|-----------|-------|
| 85 | 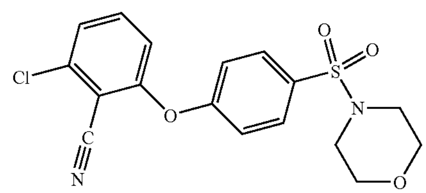 | 1-{2-chloro-6-[4-(morpholin-4-ylsulfonyl)phenoxy]phenyl}methanamine |
| 86 | 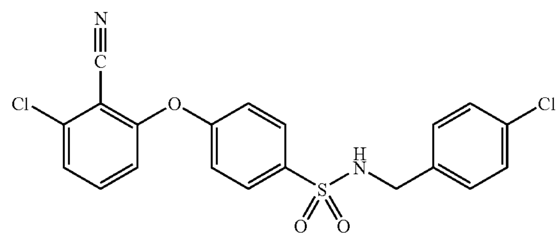 | 4-[2-(aminomethyl)-3-chlorophenoxy]-N-(4-chlorobenzyl)benzenesulfonamide |
| 87 | 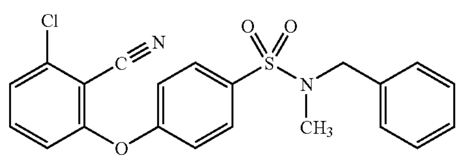 | 4-[2-(aminomethyl)-3-chlorophenoxy]-N-benzyl-N-methylbenzenesulfonamide |
| 88 | 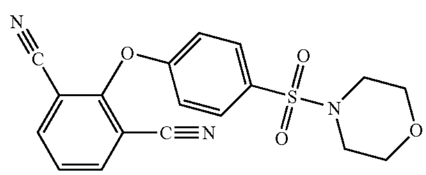 | {2-[4-(morpholin-4-ylsulfonyl)phenoxy]-1,3-phenylene}dimethanamine |
| 89 | 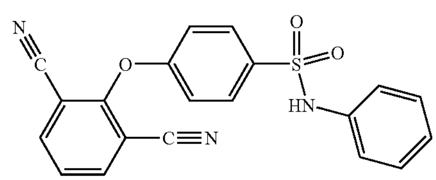 | 4-[2,6-bis(aminomethyl)phenoxy]-N-phenylbenzenesulfonamide |
| 90 | 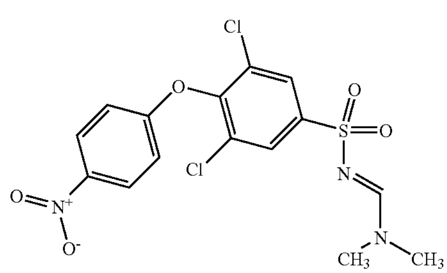 | 3,5-dichloro-N-[(1E)-(dimethylamino)methylene]-4-(4-nitrophenoxy)benzenesulfonamide |
| 91 | 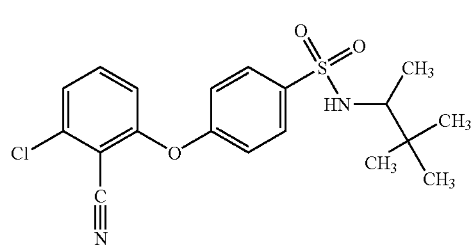 | 4-[2-(aminomethyl)-3-chlorophenoxy]-N-(1,2,2-trimethylpropyl)benzenesulfonamide |

-continued
| Example | Structure | Names |
|---|---|---|
| 92 | 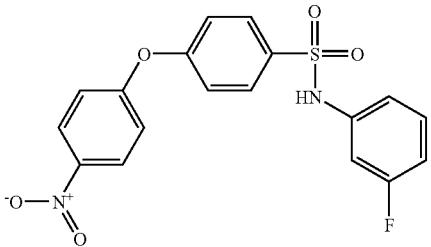 | N-(3-fluorophenyl)-4-(4-nitrophenoxy)benzenesulfonamide |
| 93 | 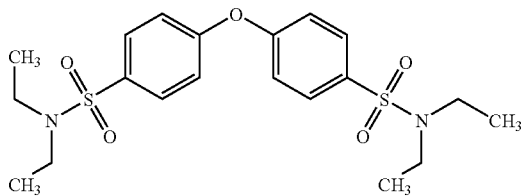 | 4,4'-oxybis(N,N-diethylbenzenesulfonamide) |
| 94 | 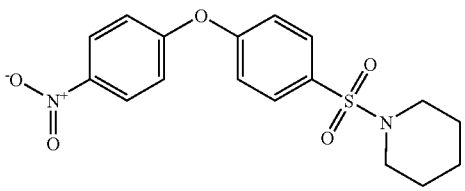 | 1-{[4-(4-nitrophenoxy)phenyl]sulfonyl}piperidine |
| 95 | 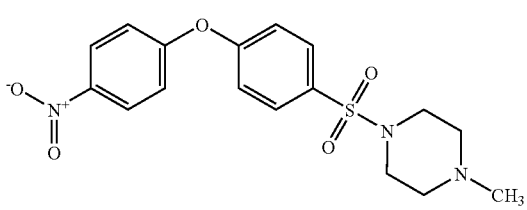 | 1-methyl-4-{[4-(4-nitrophenoxy)phenyl]sulfonyl}piperazine |
| 96 | 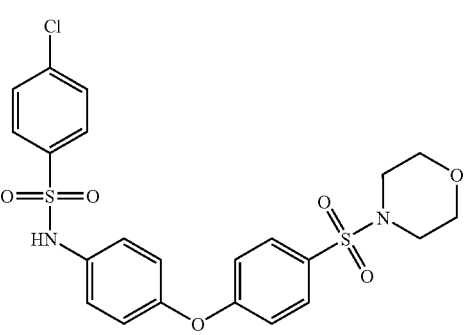 | 4-chloro-N-{4-[4-(morpholin-4-ylsulfonyl)phenoxy]phenyl}benzenesulfonamide |
| 97 | 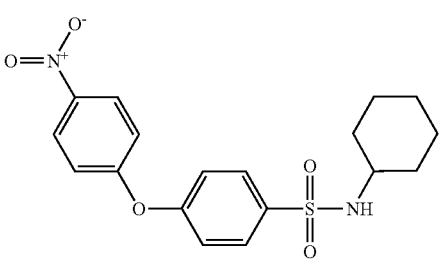 | N-cyclohexyl-4-(4-nitrophenoxy)benzenesulfonamide |

-continued

| Example | Structure | Names |
| --- | --- | --- |
| 98 | 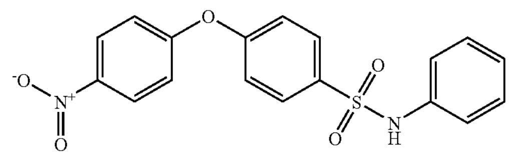 | 4-(4-nitrophenoxy)-N-phenylbenzene-sulfonamide |
| 99 | 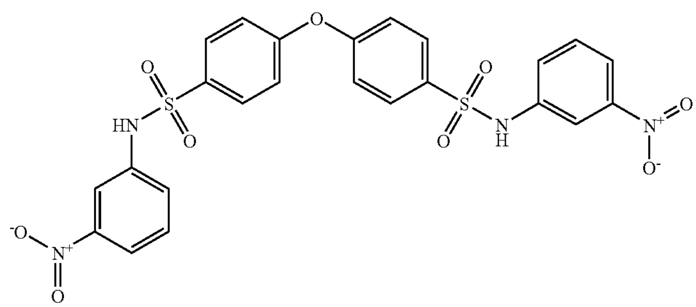 | 4,4'-oxybis[N-(3-nitrophenyl)benzene-sulfonamide] |
| 100 | 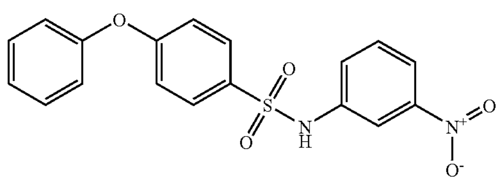 | N-(3-nitrophenyl)-4-phenoxybenzene-sulfonamide |
| 101 | 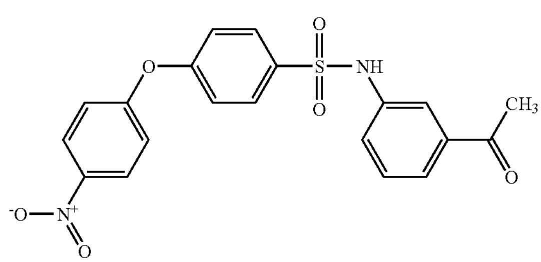 | N-(3-acetylphenyl)-4-(4-nitrophenoxy)benzenesulfonamide |
| 102 | 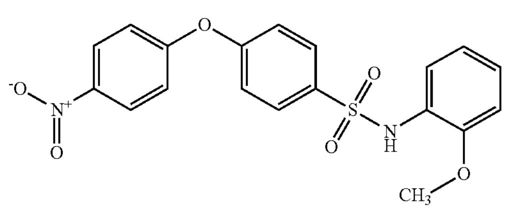 | N-(2-methoxyphenyl)-4-(4-nitrophenoxy)benzenesulfonamide |
| 103 | 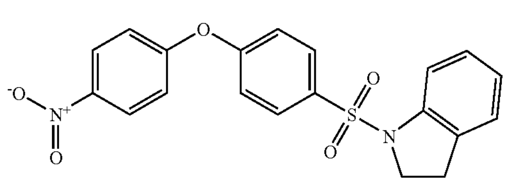 | 1-{[4-(4-nitrophenoxy)phenyl]sulfonyl}indoline |
| 104 | 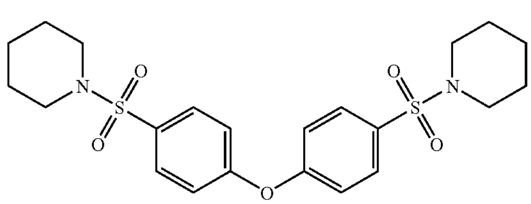 | 1,1'-[oxybis(4,1-phenylenesulfonyl)]dipiperidine |

-continued

| Example | Structure | Names |
|---|---|---|
| 105 | 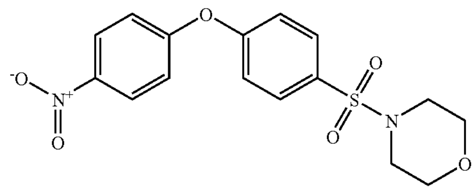 | 4-{[4-(4-nitrophenoxy)phenyl]sulfonyl}morpholine |
| 106 | 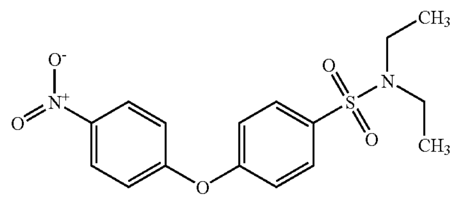 | N,N-diethyl-4-(4-nitrophenoxy)benzenesulfonamide |
| 107 | 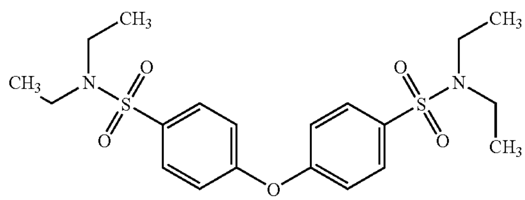 | 4,4'-oxybis(N,N-diethylbenzenesulfonamide) |
| 108 | 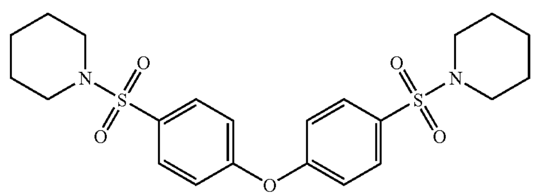 | 1,1'-[oxybis(4,1-phenylenesulfonyl)]dipiperidine |
| 109 | 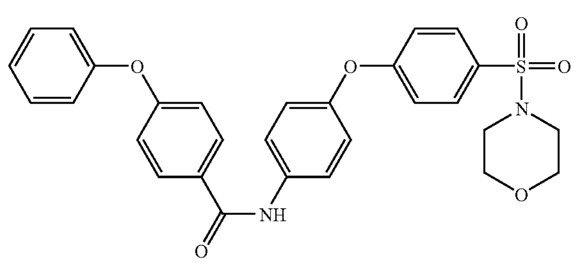 | N-{4-[4-(morpholin-4-ylsulfonyl)phenoxy]phenyl}-4-phenoxybenzamide |
| 110 | 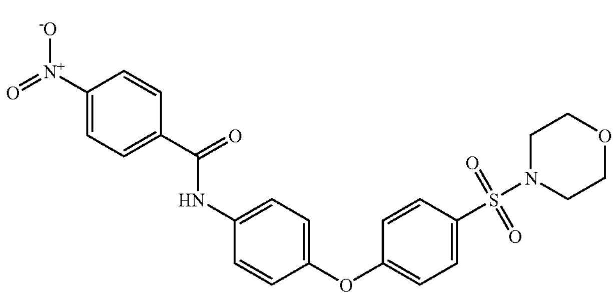 | N-{4-[4-(morpholin-4-ylsulfonyl)phenoxy]phenyl}-4-nitrobenzamide |

-continued

| Example | Structure | Names |
|---|---|---|
| 111 | 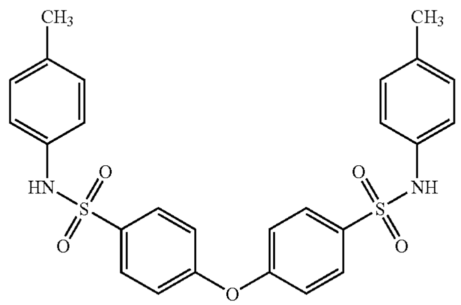 | 4,4'-oxybis[N-(4-methylphenyl)benzene-sulfonamide] |
| 112 | 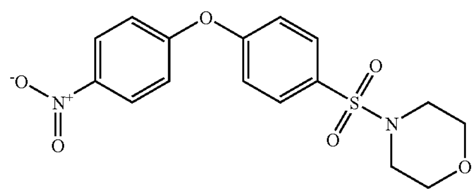 | 4-{[4-(4-nitrophenoxy)phenyl]sulfonyl}morpholine |
| 113 | 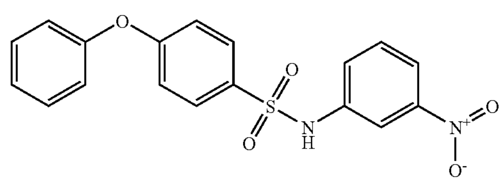 | N-(3-nitrophenyl)-4-phenoxybenzene-sulfonamide |
| 114 | 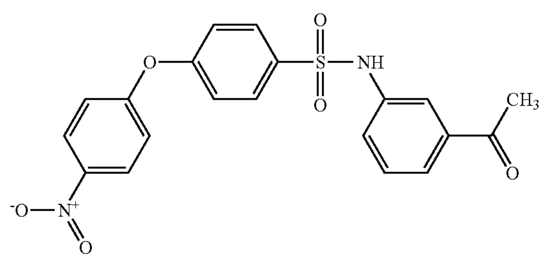 | N-(3-acetylphenyl)-4-(4-nitrophenoxy)benzenesulfonamide |
| 115 | 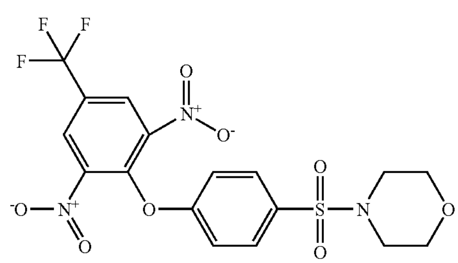 | 4-({4-[2,6-dinitro-4-(trifluoromethyl)phenoxy]phenyl}sulfonyl)morpholine |
| 116 | 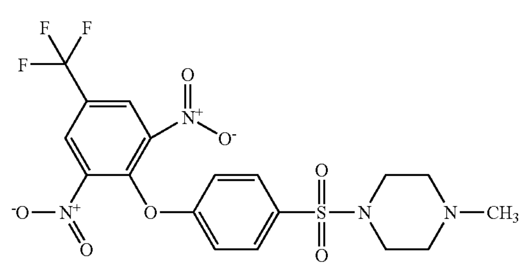 | 1-({4-[2,6-dinitro-4-(trifluoromethyl)phenoxy]phenyl}sulfonyl)-4-methylpiperazine |

| Example | Structure | Names |
|---|---|---|
| 117 | 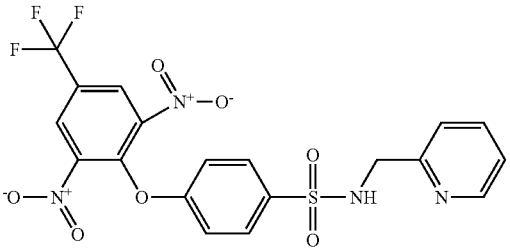 | 4-[2,6-dinitro-4-(trifluoromethyl)phenoxy]-N-(pyridin-2-ylmethyl)benzenesulfonamide |
| 118 | 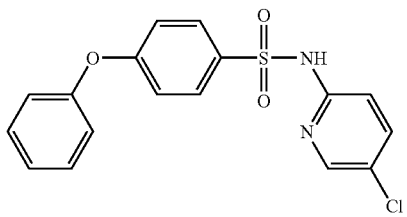 | N-(5-chloropyridin-2-yl)-4-phenoxybenzenesulfonamide |
| 119 | 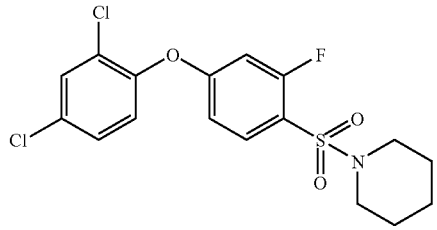 | 1-{[4-(2,4-dichlorophenoxy)-2-fluorophenyl]sulfonyl}piperidine |
| 120 | 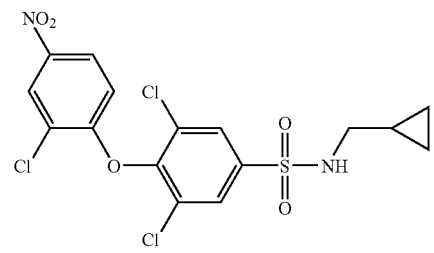 | 3,5-dichloro-4-(2-chloro-4-nitrophenoxy)-N-(cyclopropylmethyl)benzenesulfonamide |
| 121 | 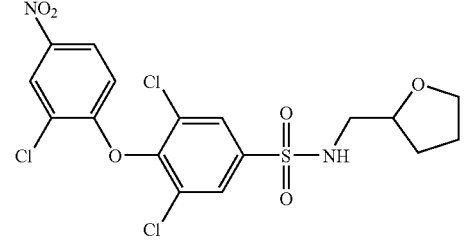 | 3,5-dichloro-4-(2-chloro-4-nitrophenoxy)-N-(tetrahydrofuran-2-ylmethyl)benzenesulfonamide |
| 122 | 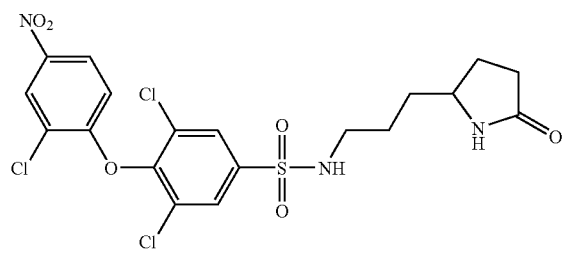 | 3,5-dichloro-4-(2-chloro-4-nitrophenoxy)-N-[3-(5-oxopyrrolidin-2-yl)propyl]benzenesulfonamide |

-continued

| Example | Structure | Names |
|---|---|---|
| 123 | 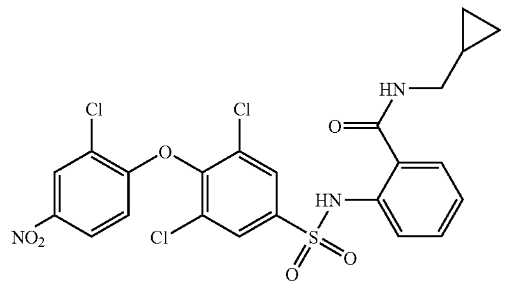 | N-(cyclopropylmethyl)-2-({[3,5-dichloro-4-(2-chloro-4-nitrophenoxy)phenyl]sulfonyl}amino)benzamide |
| 124 | 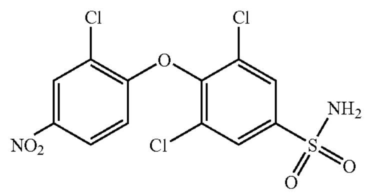 | 3,5-dichloro-4-(2-chloro-4-nitrophenoxy)benzenesulfonamide |
| 125 | 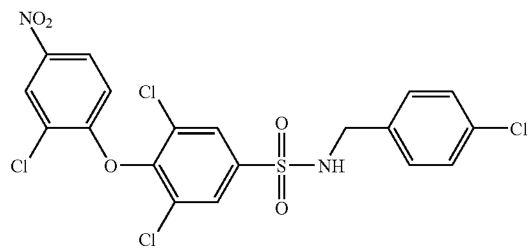 | 3,5-dichloro-N-(4-chlorobenzyl)-4-(2-chloro-4-nitrophenoxy)benzenesulfonamide |
| 126 | 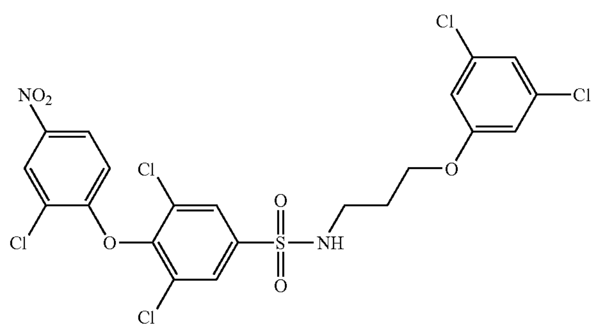 | 3,5-dichloro-4-(2-chloro-4-nitrophenoxy)-N-[3-(3,5-dichlorophenoxy)propyl]benzenesulfonamide |
| 127 | 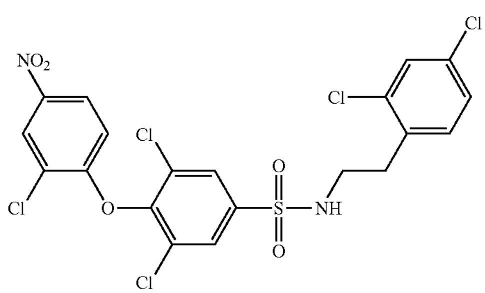 | 3,5-dichloro-4-(2-chloro-4-nitrophenoxy)-N-[2-(2,4-dichlorophenyl)ethyl]benzenesulfonamide |
| 128 | 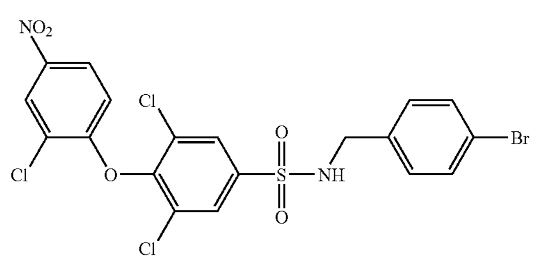 | N-(4-bromobenzyl)-3,5-dichloro-4-(2-chloro-4-nitrophenoxy)benzenesulfonamide |

-continued

| Example | Structure | Names |
|---|---|---|
| 129 | 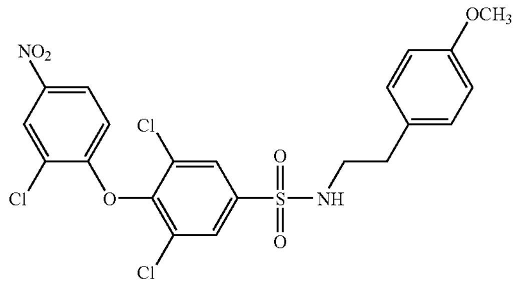 | 3,5-dichloro-4-(2-chloro-4-nitrophenoxy)-N-[2-(4-methoxyphenyl)ethyl]benzenesulfonamide |
| 130 | 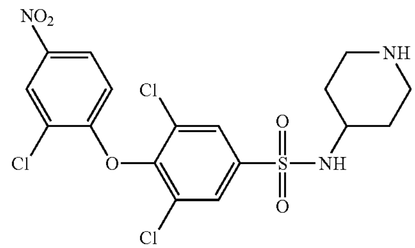 | 3,5-dichloro-4-(2-chloro-4-nitrophenoxy)-N-piperidin-4-ylbenzenesulfonamide |
| 131 | 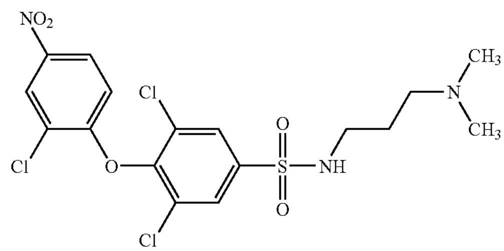 | 3,5-dichloro-4-(2-chloro-4-nitrophenoxy)-N-[3-dimethylamino)propyl]benzenesulfonamide |
| 132 | 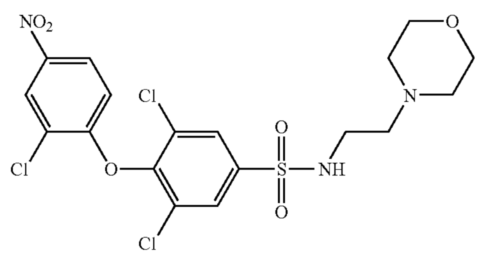 | 3,5-dichloro-4-(2-chloro-4-nitrophenoxy)-N-(2-morpholin-4-ylethyl)benzenesulfonamide |
| 133 | 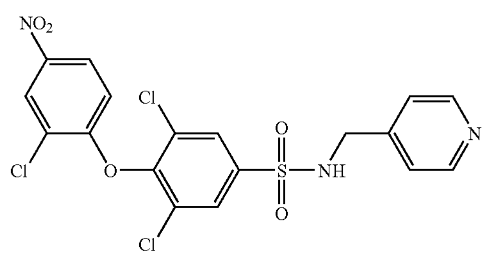 | 3,5-dichloro-4-(2-chloro-4-nitrophenoxy)-N-(pyridin-4-ylmethyl)benzenesulfonamide |
| 134 | 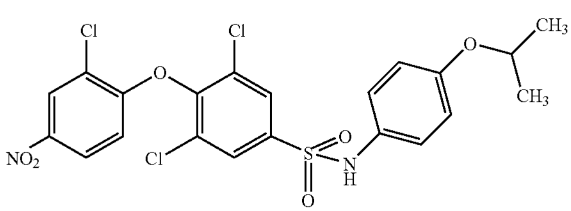 | 3,5-dichloro-4-(2-chloro-4-nitrophenoxy)-N-(4-isopropoxyphenyl)benzenesulfonamide |

| Example | Structure | Names |
|---|---|---|
| 135 | 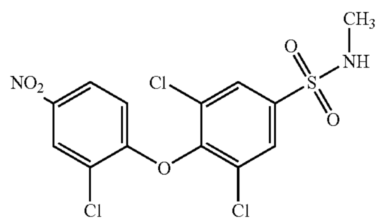 | 3,5-dichloro-4-(2-chloro-4-nitrophenoxy)-N-methylbenzenesulfonamide |
| 136 | 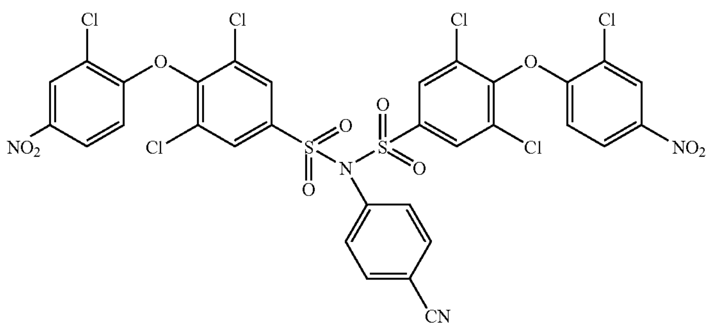 | 3,5-dichloro-4-(2-chloro-4-nitrophenoxy)-N-(4-cyanophenyl)-N-(1,3-dichloro-2-(2-chloro-4-nitrophenoxy)-5-sulfonylbenzene)-benzenesulfonamide |
| 137 | 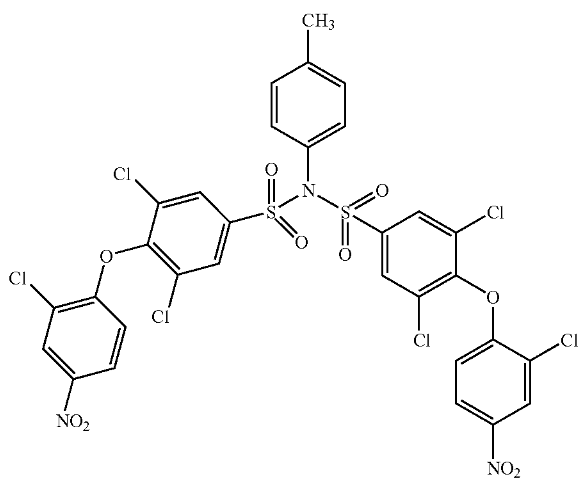 | 3,5-dichloro-4-(2-chloro-4-nitrophenoxy)-N-(4-methylphenyl)-N-(1,3-dichloro-2-(2-chloro-4-nitrophenoxy)-5-sulfonylbenzene) benzenesulfonamide |
| 138 | 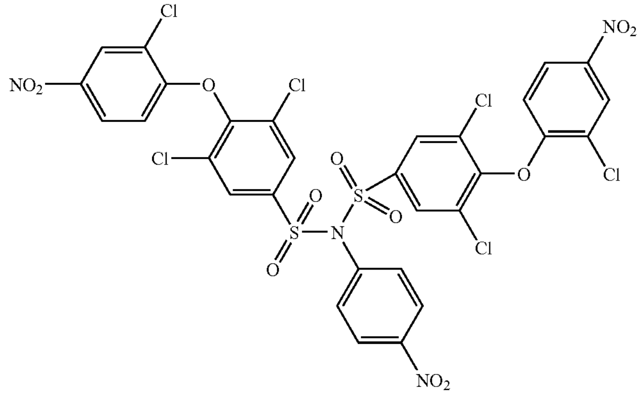 | 3,5-dichloro-4-(2-chloro-4-nitrophenoxy)-N-(1,3-dichloro-2-(2-chloro-4-nitrophenoxy)-5-sulfonylbenzene)-N-(4-nitrophenyl) benzenesulfonamide |

-continued

| Example | Structure | Names |
| --- | --- | --- |
| 139 | 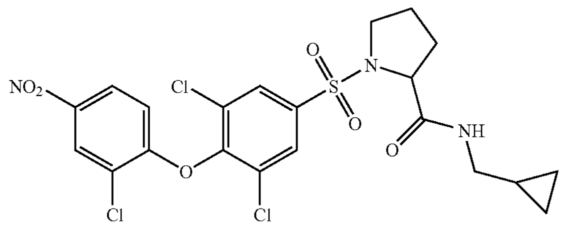 | N-(cyclopropylmethyl)-1-{[3,5-dichloro-4-(2-chloro-4-nitrophenoxy)phenyl]sulfonyl} prolinamide |
| 140 | 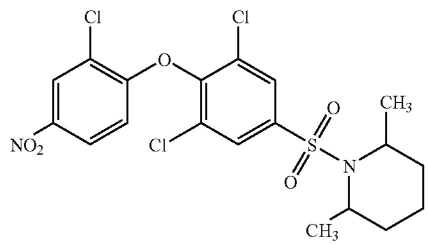 | 1-{[3,5-dichloro-4-(2-chloro-4-nitrophenoxy) phenyl]sulfonyl}-2,6-dimethylpiperidine |
| 141 | 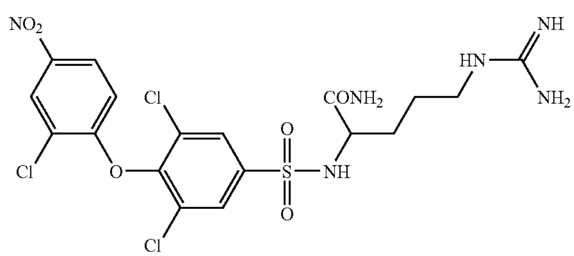 | $N^2$-{[3,5-dichloro-4-(2-chloro-4-nitrophenoxy) phenyl]sulfonyl}argininamide |
| 142 | 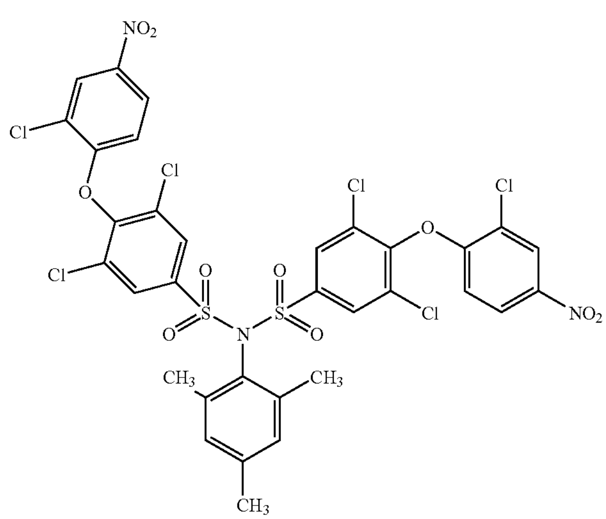 | 3,5-dichloro-4-(2-chloro-4-nitrophenoxy)-N-mesityl-N-(1,3-dichloro-2-(2-chloro-4-nitrophenoxy)-5-sulfonylbenzene)benzene-sulfonamide |

| Example | Structure | Names |
|---|---|---|
| 143 | 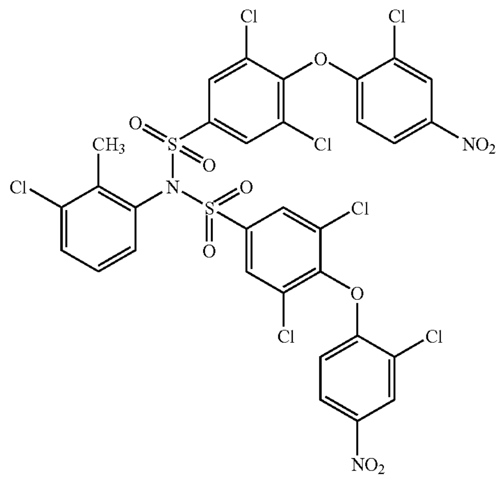 | 3,5-dichloro-N-(3-chloro-2-methylphenyl)-4-(2-chloro-4-nitrophenoxy)-N-(1,3-dichloro-2-(2-chloro-4-nitrophenoxy)-5-sulfonylbenzene)benzenesulfonamide |
| 144 | 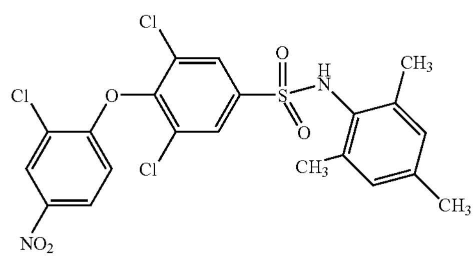 | 3,5-dichloro-4-(2-chloro-4-nitrophenoxy)-N-mesitylbenzenesulfonamide |
| 145 | 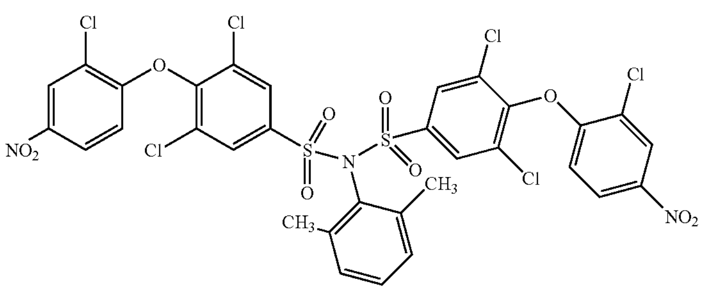 | 3,5-dichloro-4-(2-chloro-4-nitrophenoxy)-N-(2,6-dimethylphenyl)-N-(1,3-dichloro-2-(2-chloro-4-nitrophenoxy)5-sulfonyl benzene)benzenesulfonamide |
| 146 | 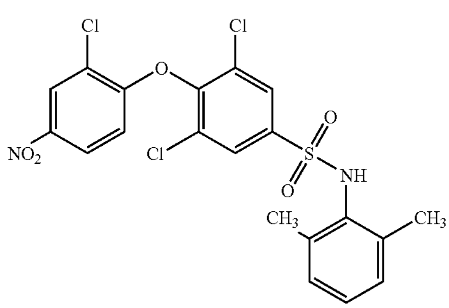 | 3,5-dichloro-4-(2-chloro-4-nitrophenoxy)-N-(2,6-dimethylphenyl)benzenesulfonamide |

-continued

| Example | Structure | Names |
|---|---|---|
| 147 | 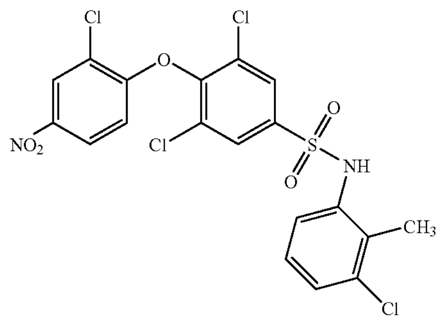 | 3,5-dichloro-N-(3-chloro-2-methylphenyl)-4-(2-chloro-4-nitrophenoxy)benzenesulfonamide |
| 148 | 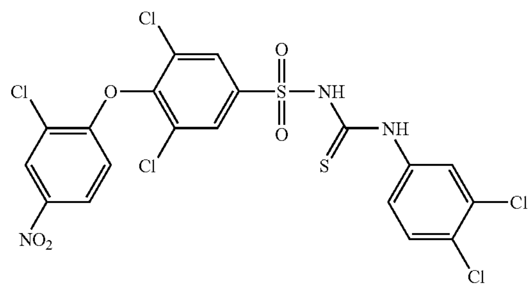 | 3,5-dichloro-4-(2-chloro-4-nitrophenoxy)-N-{[(3,4-dichlorophenyl)amino]carbonothioyl}benzenesulfonamide |
| 149 | 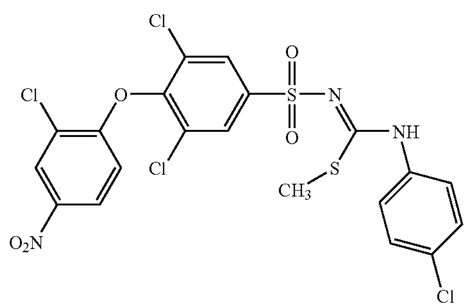 | methyl N-(4-chlorophenyl)-N'-{[3,5-dichloro-4-(2-chloro-4-nitrophenoxy)phenyl]sulfonyl} imidothiocarbamate |
| 150 | 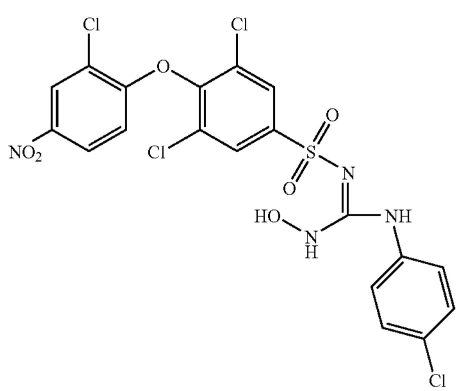 | 3,5-dichloro-4-(2-chloro-4-nitrophenoxy)-N-[(1Z)-[(4-chlorophenyl)amino](hydroxyamino)methylene]benzenesulfonamide |
| 151 | 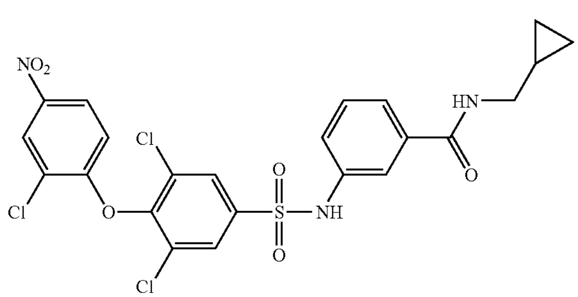 | N-(cyclopropylmethyl)-3-({[3,5-dichloro-4-(2-chloro-4-nitrophenoxy)phenyl]sulfonyl}amino)benzamide |

| Example | Structure | Names |
|---|---|---|
| 152 | 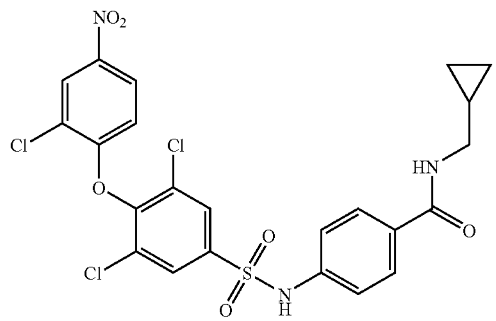 | N-(cyclopropylmethyl)-4-({[3,5-dichloro-4-(2-chloro-4-nitrophenoxy)phenyl]sulfonyl}amino)benzamide |
| 153 | 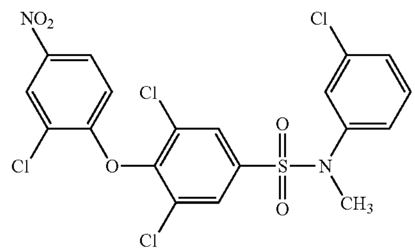 | 3,5-dichloro-4-(2-chloro-4-nitrophenoxy)-N-(3-chlorophenyl)-N-methylbenzenesulfonamide |
| 154 | 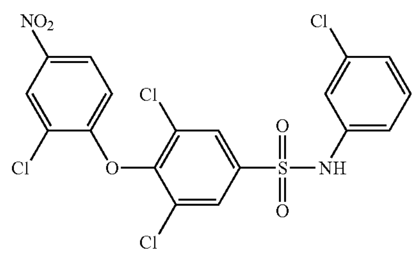 | 3,5-dichloro-4-(2-chloro-4-nitrophenoxy)-N-(3-chlorophenyl)benzenesulfonamide |
| 155 | 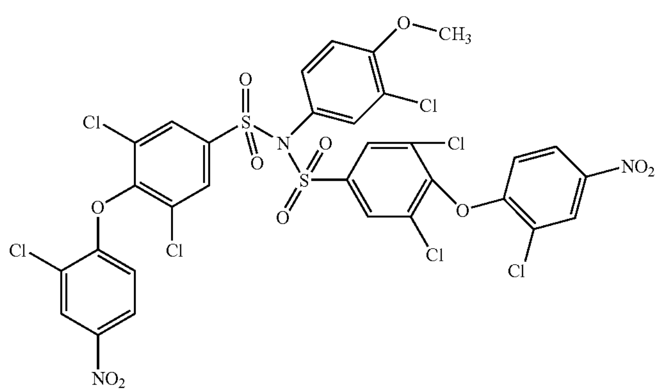 | 3,5-dichloro-N-(3-chloro-4-methoxyphenyl)-4-(2-chloro-4-nitrophenoxy)-N-(1,3-dichloro-2-(2-chloro-4-nitrophenoxy)-5-sulfonylbenzene)benzenesulfonamide |
| 156 | 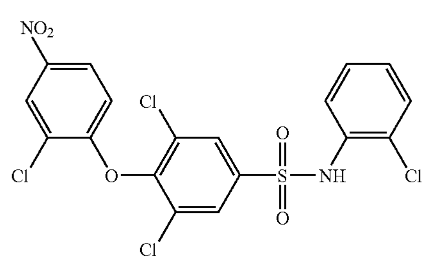 | 3,5-dichloro-4-(2-chloro-4-nitrophenoxy)-N-(2-chlorophenyl)benzenesulfonamide |

-continued

| Example | Structure | Names |
|---|---|---|
| 157 | 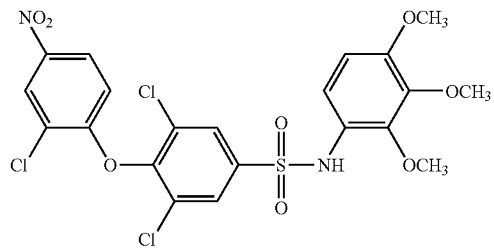 | 3,5-dichloro-4-(2-chloro-4-nitrophenoxy)-N-(2,3,4-trimethoxyphenyl)benzenesulfonamide |
| 158 | 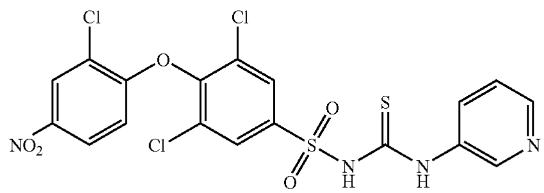 | 3,5-dichloro-4-(2-chloro-4-nitrophenoxy)-N-[(pyridin-3-ylamino)carbonothioyl]benzenesulfonamide |
| 159 | 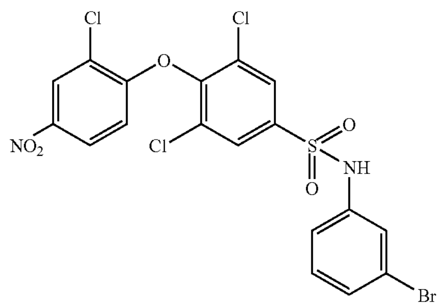 | N-(3-bromophenyl)-3,5-dichloro-4-(2-chloro-4-nitrophenoxy)benzenesulfonamide |
| 160 | 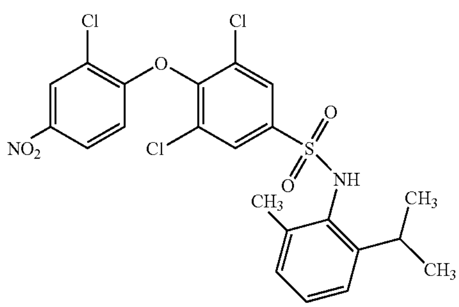 | 3,5-dichloro-4-(2-chloro-4-nitrophenoxy)-N-(2-isopropyl-6-methylphenyl)benzenesulfonamide |
| 161 | 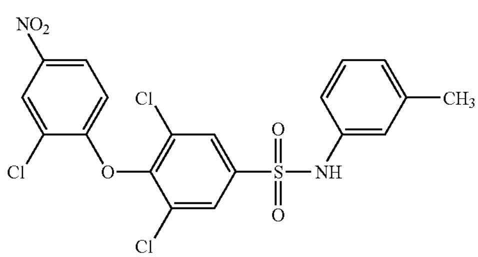 | 3,5-dichloro-4-(2-chloro-4-nitrophenoxy)-N-(3-methylphenyl)benzenesulfonamide |

| Example | Structure | Names |
|---|---|---|
| 162 | 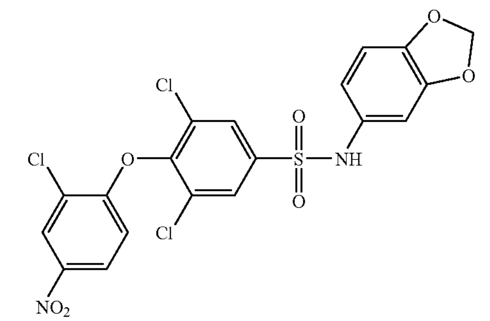 | N-1,3-benzodioxol-5-yl-3,5-dichloro-4-(2-chloro-4-nitrophenoxy)benzenesulfonamide |
| 163 | 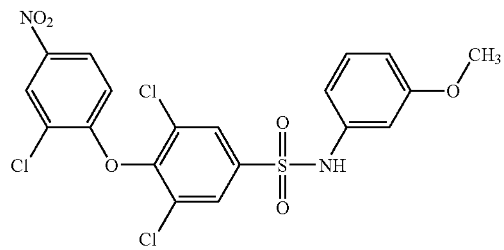 | 3,5-dichloro-4-(2-chloro-4-nitrophenoxy)-N-(3-methoxyphenyl)benzenesulfonamide |
| 164 | 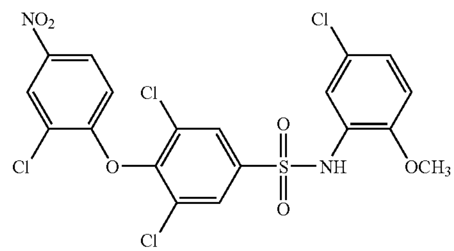 | 3,5-dichloro-N-(5-chloro-2-methoxyphenyl)-4-(2-chloro-4-nitrophenoxy)benzenesulfonamide |
| 165 | 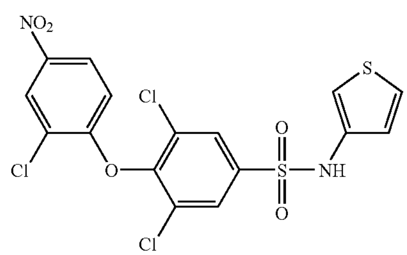 | 3,5-dichloro-4-(2-chloro-4-nitrophenoxy)-N-3-thienylbenzenesulfonamide |
| 166 | 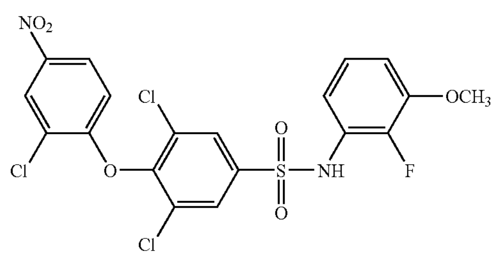 | 3,5-dichloro-4-(2-chloro-4-nitrophenoxy)-N-(2-fluoro-3-methoxyphenyl)benzenesulfonamide |
| 167 | 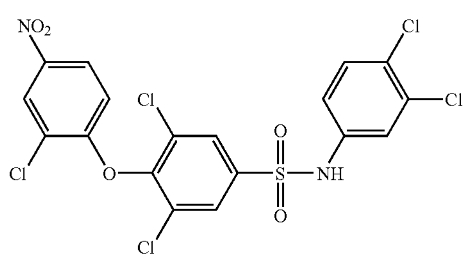 | 3,5-dichloro-4-(2-chloro-4-nitrophenoxy)-N-(3,4-dichlorophenyl)benzenesulfonamide |

| Example | Structure | Names |
|---|---|---|
| 168 | 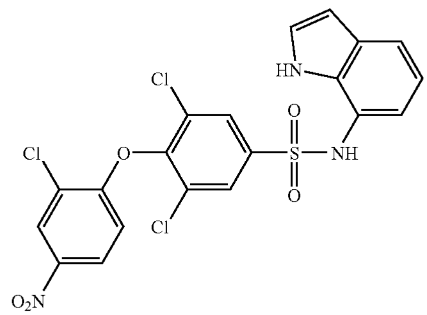 | 3,5-dichloro-4-(2-chloro-4-nitrophenoxy)-N-1H-indol-7-ylbenzenesulfonamide |
| 169 | 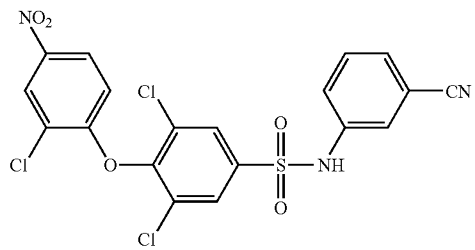 | 3,5-dichloro-4-(2-chloro-4-nitrophenoxy)-N-(3-cyanophenyl)benzenesulfonamide |
| 170 | 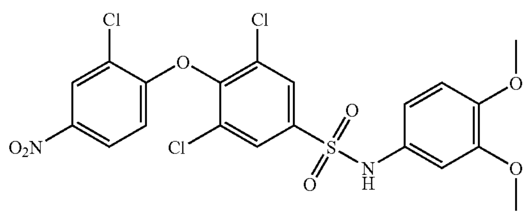 | 3,5-dichloro-4-(2-chloro-4-nitrophenoxy)-N-(3,4-dimethoxyphenyl)benzenesulfonamide |
| 171 | 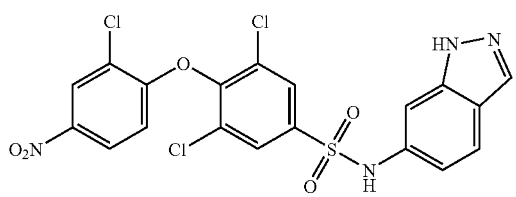 | 3,5-dichloro-4-(2-chloro-4-nitrophenoxy)-N-1H-indazol-6-ylbenzenesulfonamide |
| 172 | 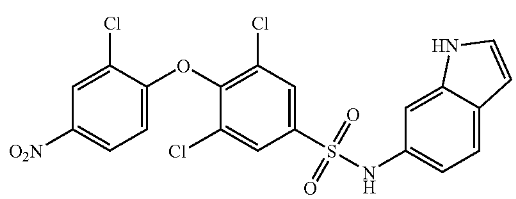 | 3,5-dichloro-4-(2-chloro-4-nitrophenoxy)-N-1H-indol-6-ylbenzenesulfonamide |
| 173 | 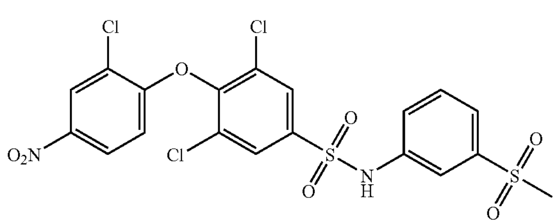 | 3,5-dichloro-4-(2-chloro-4-nitrophenoxy)-N-[3-(methylsulfonyl)phenyl]benzenesulfonamide |
| 174 | 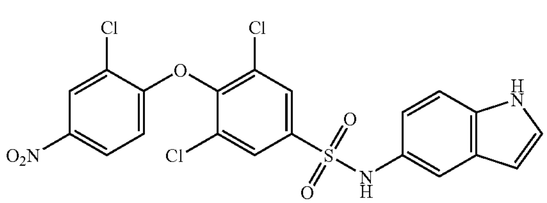 | 3,5-dichloro-4-(2-chloro-4-nitrophenoxy)-N-1H-indol-5-ylbenzenesulfonamide |

| Example | Structure | Names |
|---|---|---|
| 175 | 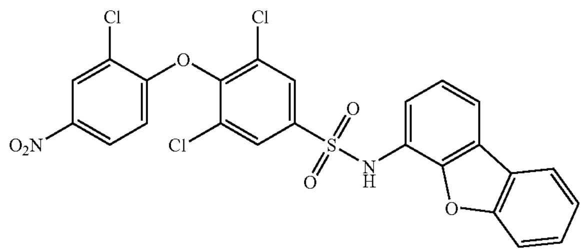 | 3,5-dichloro-4-(2-chloro-4-nitrophenoxy)-N-dibenzo[b,d]furan-4-ylbenzenesulfonamide |
| 176 | 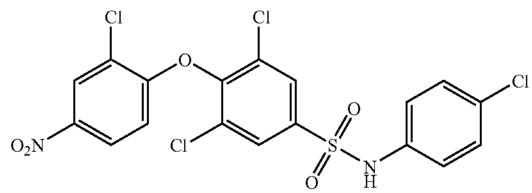 | 3,5-dichloro-4-(2-chloro-4-nitrophenoxy)-N-(4-chlorophenyl)benzenesulfonamide |
| 177 | 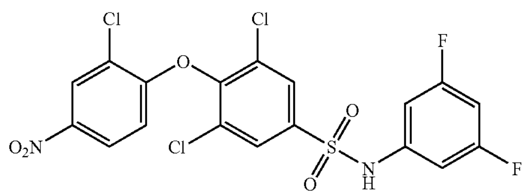 | 3,5-dichloro-4-(2-chloro-4-nitrophenoxy)-N-(3,5-difluorophenyl)benzenesulfonamide |
| 178 | 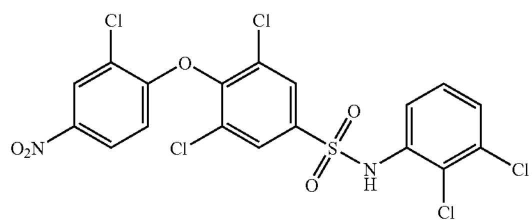 | 3,5-dichloro-4-(2-chloro-4-nitrophenoxy)-N-(2,3-dichlorophenyl)benzenesulfonamide |
| 179 | 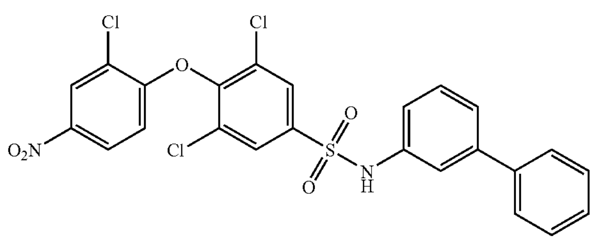 | N-biphenyl-3-yl-3,5-dichloro-4-(2-chloro-4-nitrophenoxy)benzenesulfonamide |
| 180 | 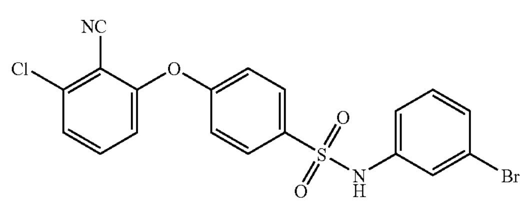 | N-(3-bromophenyl)-4-(3-chloro-2-cyanophenoxy)benzenesulfonamide |
| 181 | 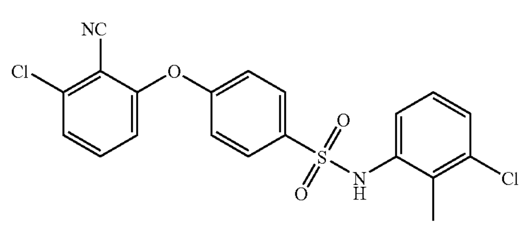 | 4-(3-chloro-2-cyanophenoxy)-N-(3-chloro-2-methylphenyl)benzenesulfonamide |

| Example | Structure | Names |
|---|---|---|
| 182 | 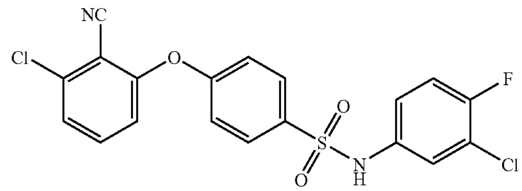 | 4-(3-chloro-2-cyanophenoxy)-N-(3-chloro-4-fluorophenyl)benzenesulfonamide |
| 183 | 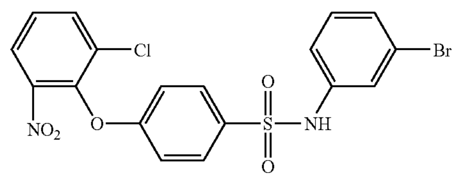 | N-(3-bromophenyl)-4-(2-chloro-6-nitrophenoxy)benzenesulfonamide |
| 184 | 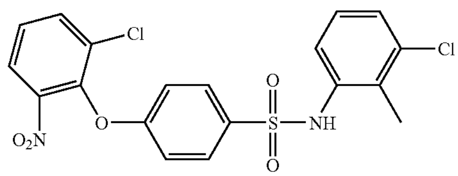 | N-(3-chloro-2-methylphenyl)-4-(2-chloro-6-nitrophenoxy)benzenesulfonamide |
| 185 | 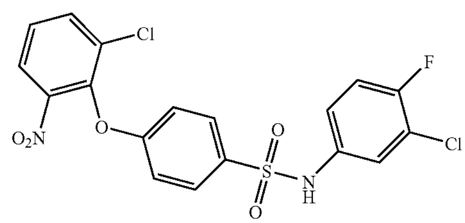 | N-(3-chloro-4-fluorophenyl)-4-(2-chloro-6-nitrophenoxy)benzenesulfonamide |
| 186 | 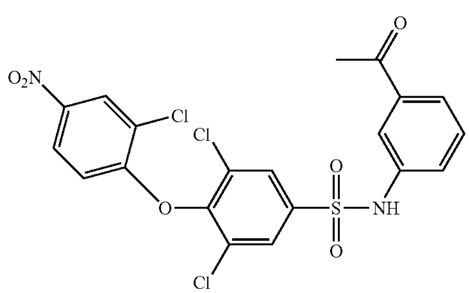 | N-(3-acetylphenyl)-3,5-dichloro-4-(2-chloro-4-nitrophenoxy)benzenesulfonamide |
| 187 | 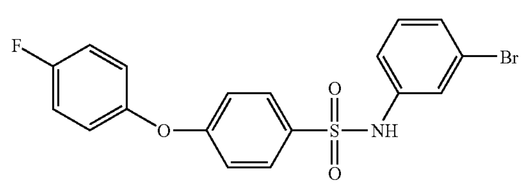 | N-(3-bromophenyl)-4-(4-fluorophenoxy)benzenesulfonamide |
| 188 | 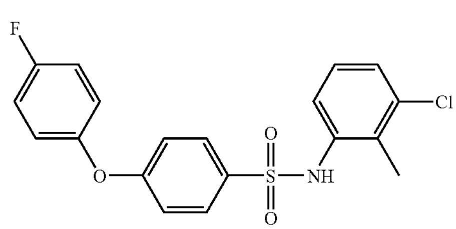 | N-(3-chloro-2-methylphenyl)-4-(4-fluorophenoxy)benzenesulfonamide |

-continued

| Example | Structure | Names |
| --- | --- | --- |
| 189 | 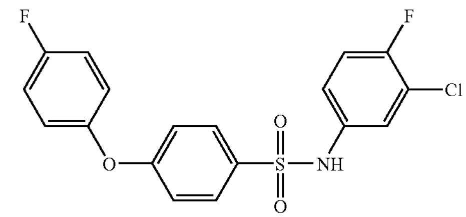 | N-(3-chloro-4-fluorophenyl)-4-(4-fluorophenoxy)benzenesulfonamide |
| 190 | 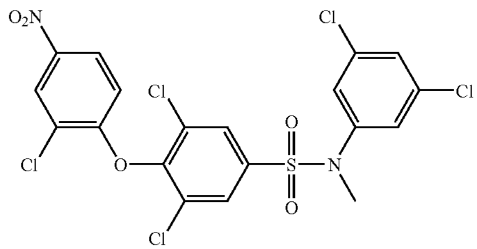 | 3,5-dichloro-4-(2-chloro-4-nitrophenoxy)-N-(3,5-dichlorophenyl)-N-methylbenzenesulfonamide |
| 191 | 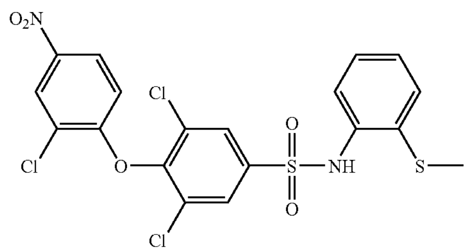 | 3,5-dichloro-4-(2-chloro-4-nitrophenoxy)-N-[2-(methylthio)phenyl]benzenesulfonamide |
| 192 | 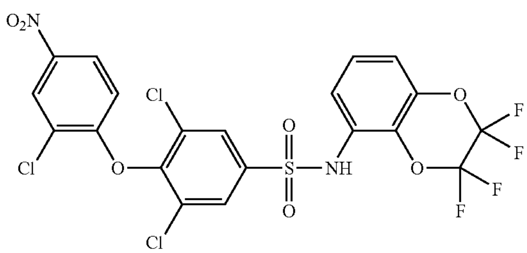 | 3,5-dichloro-4-(2-chloro-4-nitrophenoxy)-N-(2,2,3,3-tetrafluoro-2,3-dihydro-1,4-benzodioxin-5-yl)benzenesulfonamide |
| 193 | 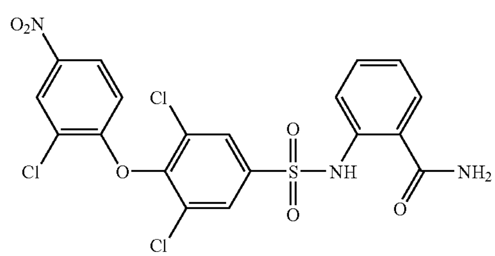 | 2-({[3,5-dichloro-4-(2-chloro-4-nitrophenoxy)phenyl]sulfonyl}amino)benzamide |
| 194 | 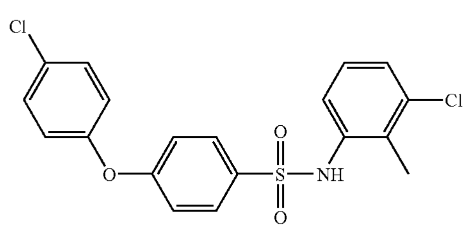 | N-(3-chloro-2-methylphenyl)-4-(4-chlorophenoxy)benzenesulfonamide |

-continued

| Example | Structure | Names |
|---|---|---|
| 195 | 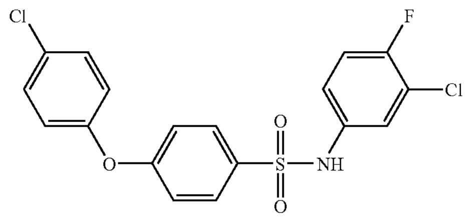 | N-(3-chloro-4-fluorophenyl)-4-(4-chlorophenoxy)benzenesulfonamide |
| 196 | 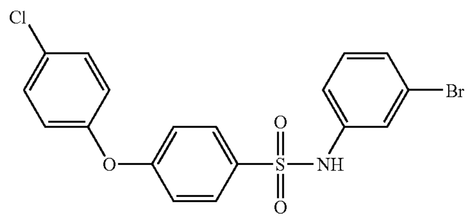 | N-(3-bromophenyl)-4-(4-chlorophenoxy)benzenesulfonamide |
| 197 | 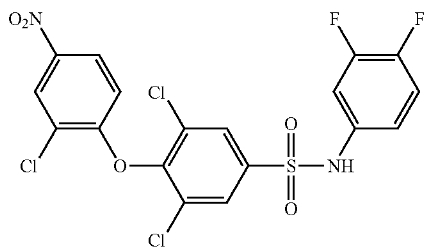 | 3,5-dichloro-4-(2-chloro-4-nitrophenoxy)-N-(3,4-difluorophenyl)benzenesulfonamide |
| 198 | 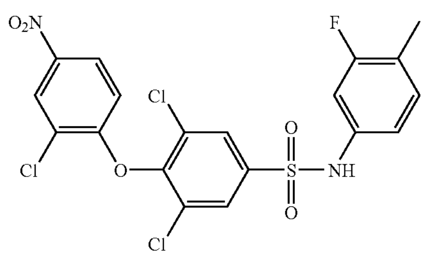 | 3,5-dichloro-4-(2-chloro-4-nitrophenoxy)-N-(3-fluoro-4-methylphenyl)benzenesulfonamide |
| 199 | 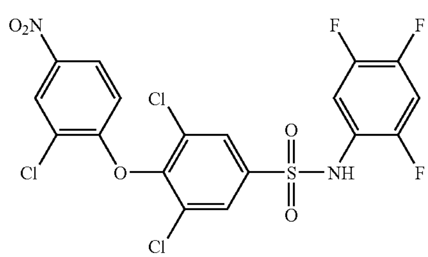 | 3,5-dichloro-4-(2-chloro-4-nitrophenoxy)-N-(2,4,5-trifluorophenyl)benzenesulfonamide |
| 200 | 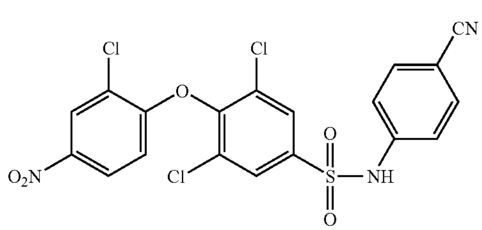 | 3,5-dichloro-4-(2-chloro-4-nitrophenoxy)-N-(4-cyanophenyl)benzenesulfonamide |

| Example | Structure | Names |
|---------|-----------|-------|
| 201 | 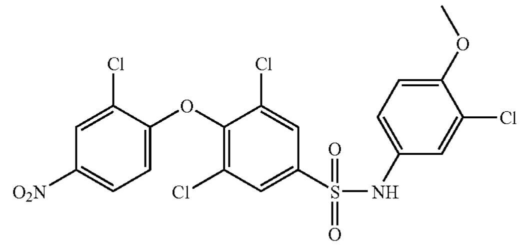 | 3,5-dichloro-N-(3-chloro-4-methoxyphenyl)-4-(2-chloro-4-nitrophenoxy)benzenesulfonamide |
| 202 | 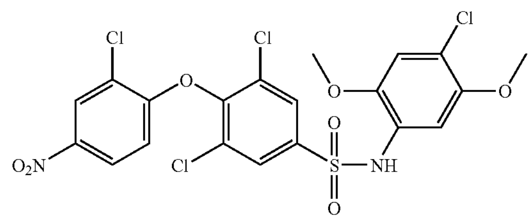 | 3,5-dichloro-N-(4-chloro-2,5-dimethoxyphenyl)-4-(2-chloro-4-nitrophenoxy)benzenesulfonamide |
| 203 | 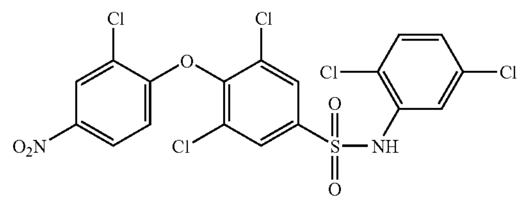 | 3,5-dichloro-4-(2-chloro-4-nitrophenoxy)-N-(2,5-dichlorophenyl)benzenesulfonamide |
| 204 | 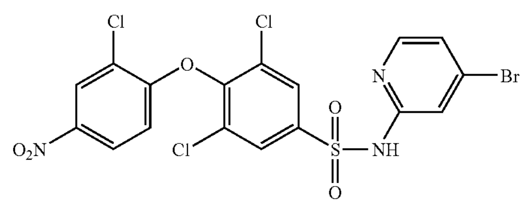 | N-(4-bromopyridin-2-yl)-3,5-dichloro-4-(2-chloro-4-nitrophenoxy)benzenesulfonamide |
| 205 | 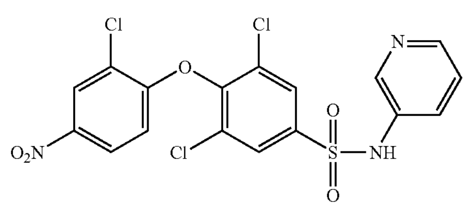 | 3,5-dichloro-4-(2-chloro-4-nitrophenoxy)-N-pyridin-3-ylbenzenesulfonamide |
| 206 | 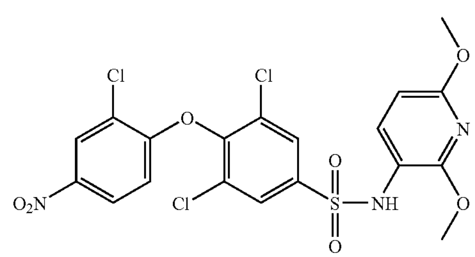 | 3,5-dichloro-4-(2-chloro-4-nitrophenoxy)-N-(2,6-dimethoxypyridin-3-yl)benzenesulfonamide |
| 207 | 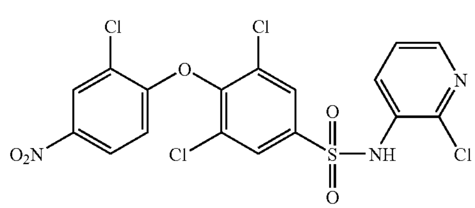 | 3,5-dichloro-4-(2-chloro-4-nitrophenoxy)-N-(2-chloropyridin-3-yl)benzenesulfonamide |

| Example | Structure | Names |
|---|---|---|
| 208 | 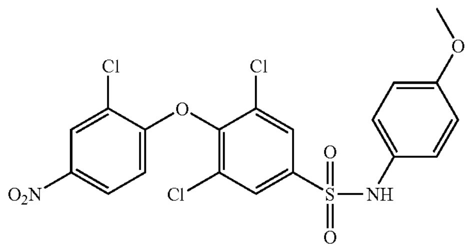 | 3,5-dichloro-4-(2-chloro-4-nitrophenoxy)-N-(4-methoxyphenyl)benzenesulfonamide |
| 209 | 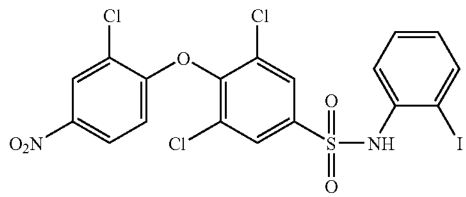 | 3,5-dichloro-4-(2-chloro-4-nitrophenoxy)-N-(2-iodophenyl)benzenesulfonamide |
| 210 | 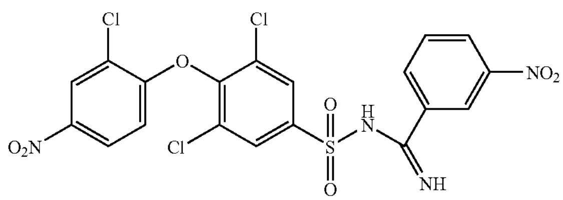 | N-{[3,5-dichloro-4-(2-chloro-4-nitrophenoxy)phenyl]sulfonyl}-3-nitrobenzenecarboximidamide |
| 211 | 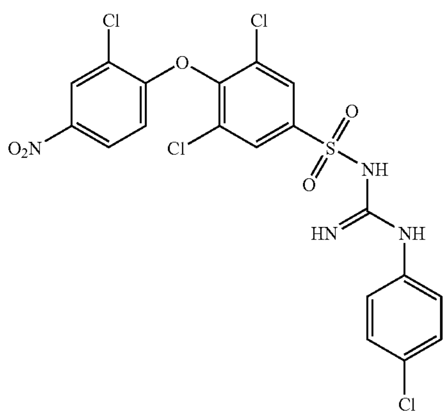 | 3,5-dichloro-4-(2-chloro-4-nitrophenoxy)-N-[[(4-chlorophenyl)amino](imino)methyl]benzenesulfonamide |
| 212 | 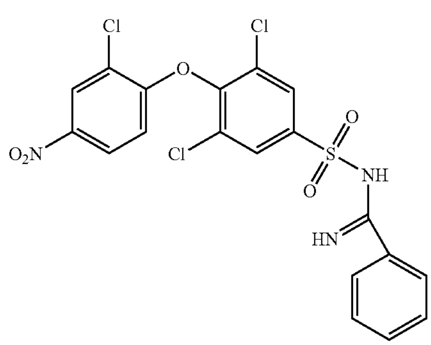 | N-{[3,5-dichloro-4-(2-chloro-4-nitrophenoxy)phenyl]sulfonyl}benzenecarboximidamide |

| Example | Structure | Names |
|---|---|---|
| 213 | 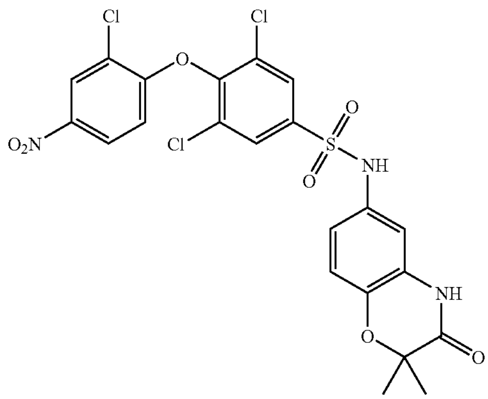 | 3,5-dichloro-4-(2-chloro-4-nitrophenoxy)-N-(2,2-dimethyl-3-oxo-3,4-dihydro-2H-1,4-benzoxazin-6-yl)benzenesulfonamide |
| 214 | 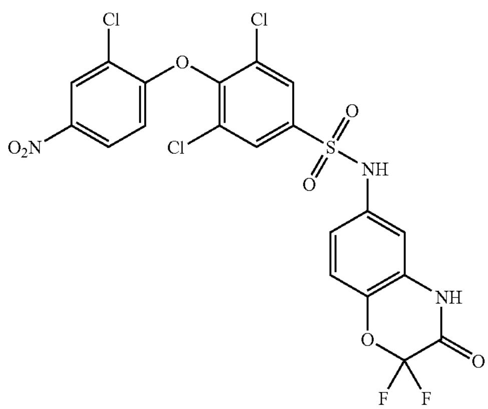 | 3,5-dichloro-4-(2-chloro-4-nitrophenoxy)-N-(2,2-difluoro-3-oxo-3,4-dihydro-2H-1,4-benzoxazin-6-yl)benzenesulfonamide |
| 215 | 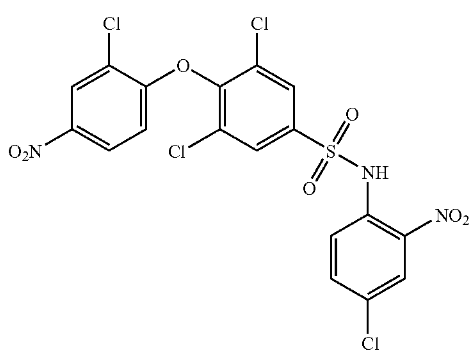 | 3,5-dichloro-4-(2-chloro-4-nitrophenoxy)-N-(4-chloro-2-nitrophenyl)benzenesulfonamide |
| 216 | 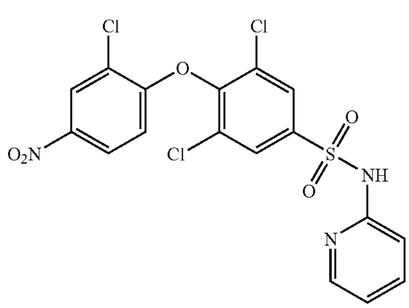 | 3,5-dichloro-4-(2-chloro-4-nitrophenoxy)-N-pyridin-2-ylbenzenesulfonamide |

| Example | Structure | Names |
|---|---|---|
| 217 | 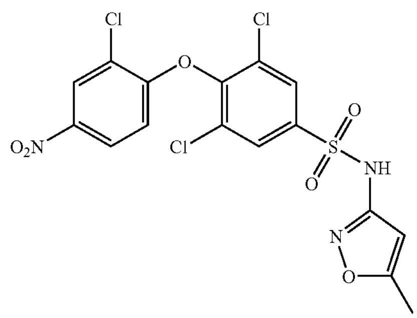 | 3,5-dichloro-4-(2-chloro-4-nitrophenoxy)-N-(5-methylisoxazol-3-yl)benzenesulfonamide |
| 218 | 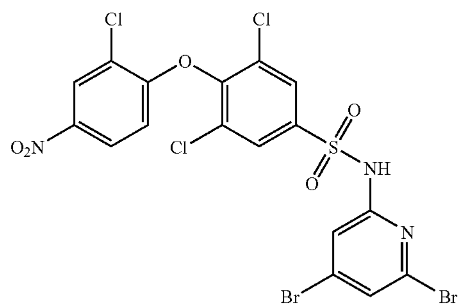 | 3,5-dichloro-4-(2-chloro-4-nitrophenoxy)-N-(4,6-dibromopyridin-2-yl)benzenesulfonamide |
| 219 | 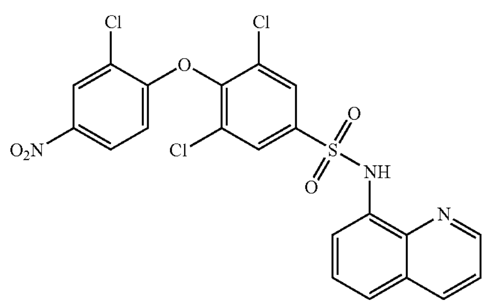 | 3,5-dichloro-4-(2-chloro-4-nitrophenoxy)-N-quinolin-8-ylbenzenesulfonamide |
| 220 | 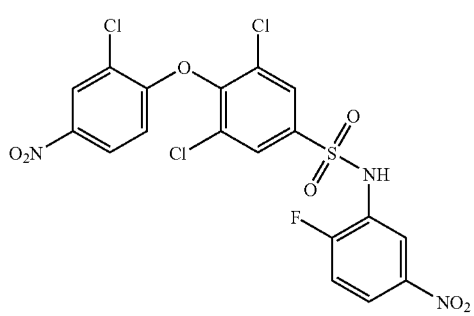 | 3,5-dichloro-4-(2-chloro-4-nitrophenoxy)-N-(2-fluoro-5-nitrophenyl)benzenesulfonamide |
| 221 | 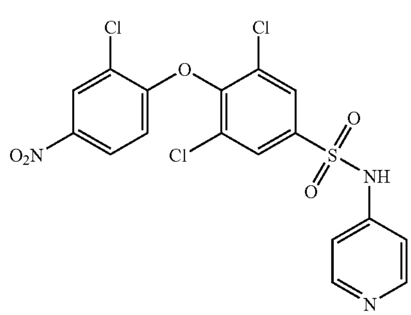 | 3,5-dichloro-4-(2-chloro-4-nitrophenoxy)-N-pyridin-4-ylbenzenesulfonamide |

| Example | Structure | Names |
|---|---|---|
| 222 | 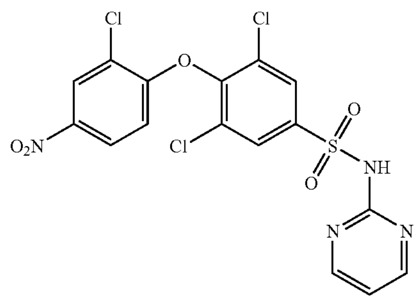 | 3,5-dichloro-4-(2-chloro-4-nitrophenoxy)-N-pyrimidin-2-ylbenzenesulfonamide |
| 223 | 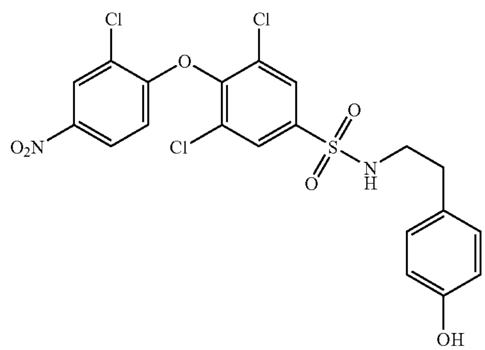 | 3,5-dichloro-4-(2-chloro-4-nitrophenoxy)-N-[2-(4-hydroxyphenyl)ethyl]benzenesulfonamide |
| 224 | 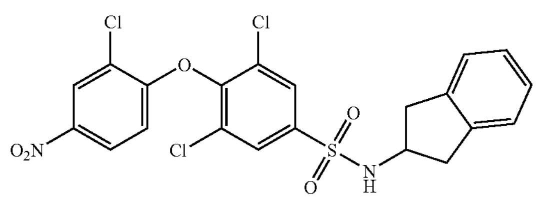 | 3,5-dichloro-4-(2-chloro-4-nitrophenoxy)-N-(2,3-dihydro-1H-inden-2-yl)benzenesulfonamide |
| 225 | 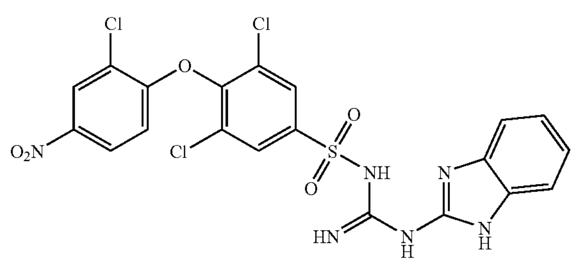 | N-[(1H-benzimidazol-2-ylamino)(imino)methyl]-3,5-dichloro-4-(2-chloro-4-nitrophenoxy)benzenesulfonamide |
| 226 | 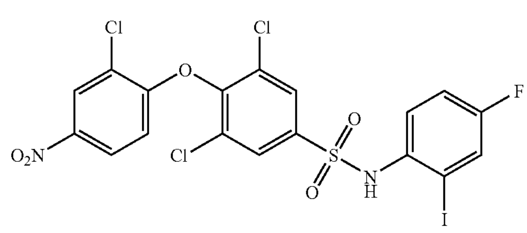 | 3,5-dichloro-4-(2-chloro-4-nitrophenoxy)-N-(4-fluoro-2-iodophenyl)benzenesulfonamide |
| 227 | 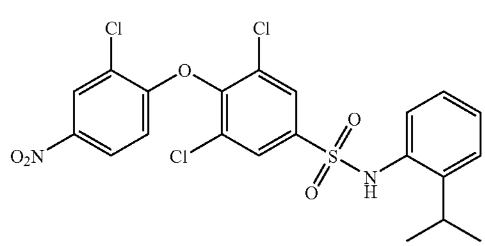 | 3,5-dichloro-4-(2-chloro-4-nitrophenoxy)-N-(2-isopropylphenyl)benzenesulfonamide |

-continued

| Example | Structure | Names |
|---|---|---|
| 228 | 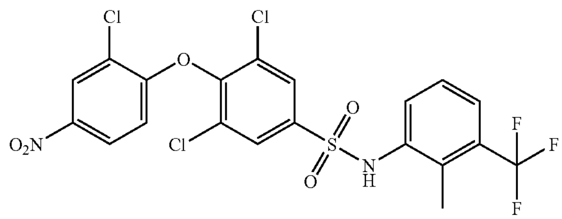 | 3,5-dichloro-4-(2-chloro-4-nitrophenoxy)-N-[2-methyl-3-(trifluoromethyl)phenyl]benzenesulfonamide |
| 229 | 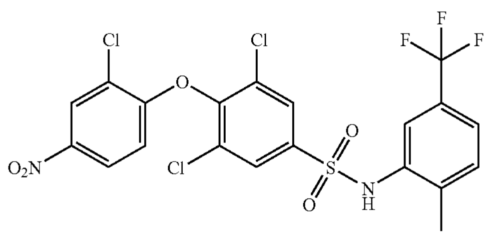 | 3,5-dichloro-4-(2-chloro-4-nitrophenoxy)-N-[2-methyl-5-(trifluoromethyl)phenyl]benzenesulfonamide |
| 230 | 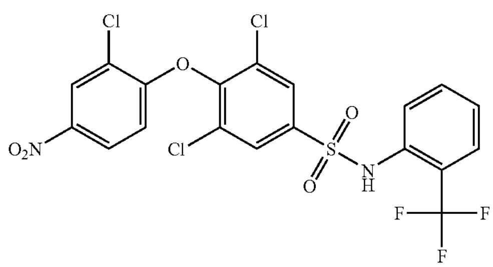 | 3,5-dichloro-4-(2-chloro-4-nitrophenoxy)-N-[2-(trifluoromethyl)phenyl]benzenesulfonamide |
| 231 | 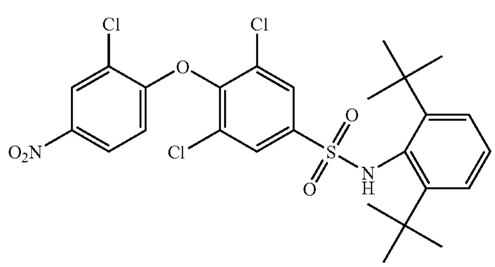 | 3,5-dichloro-4-(2-chloro-4-nitrophenoxy)-N-(2,6-di-tert-butylphenyl)benzenesulfonamide |
| 232 | 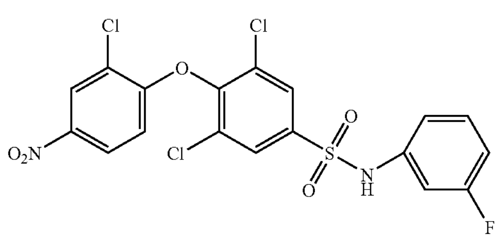 | 3,5-dichloro-4-(2-chloro-4-nitrophenoxy)-N-(3-fluorophenyl)benzenesulfonamide |
| 233 | 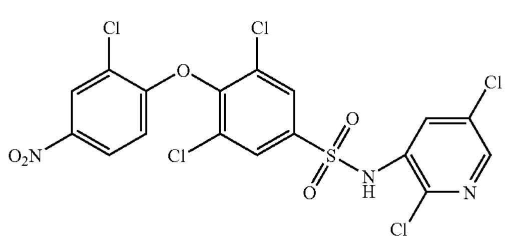 | 3,5-dichloro-4-(2-chloro-4-nitrophenoxy)-N-(2,5-dichloropyridin-3-yl)benzenesulfonamide |

-continued

| Example | Structure | Names |
|---|---|---|
| 234 | 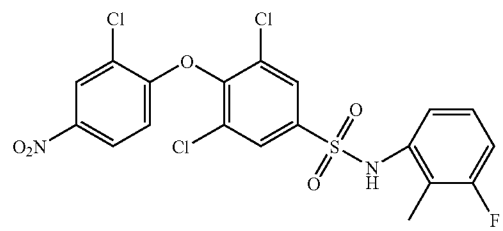 | 3,5-dichloro-4-(2-chloro-4-nitrophenoxy)-N-(3-fluoro-2-methylphenyl)benzene-sulfonamide |
| 235 | 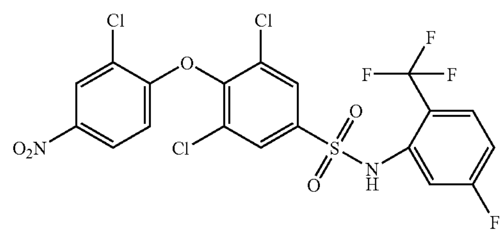 | 3,5-dichloro-4-(2-chloro-4-nitrophenoxy)-N-[5-fluoro-2-(trifluoromethyl)phenyl]benzenesulfonamide |
| 236 | 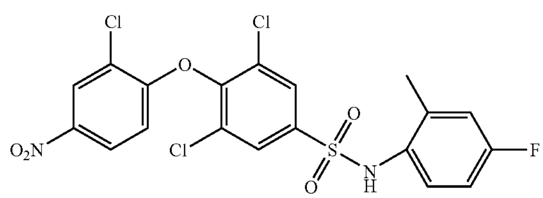 | 3,5-dichloro-4-(2-chloro-4-nitrophenoxy)-N-(4-fluoro-2-methylphenyl)benzene-sulfonamide |
| 237 | 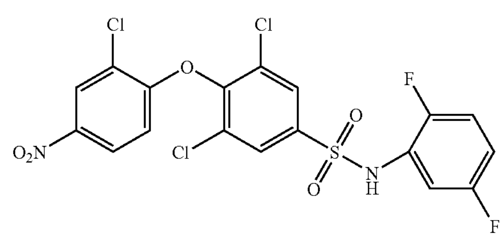 | 3,5-dichloro-4-(2-chloro-4-nitrophenoxy)-N-(2,5-difluorophenyl)benzenesulfonamide |
| 238 | 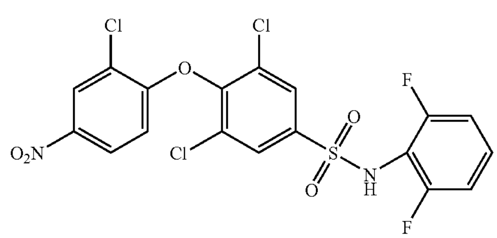 | 3,5-dichloro-4-(2-chloro-4-nitrophenoxy)-N-(2,6-difluorophenyl)benzenesulfonamide |
| 239 | 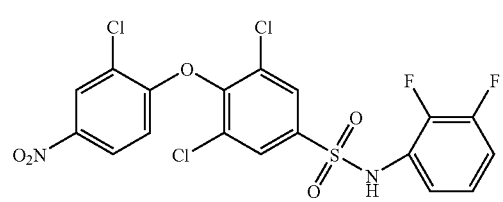 | 3,5-dichloro-4-(2-chloro-4-nitrophenoxy)-N-(2,3-difluorophenyl)benzenesulfonamide |
| 240 | 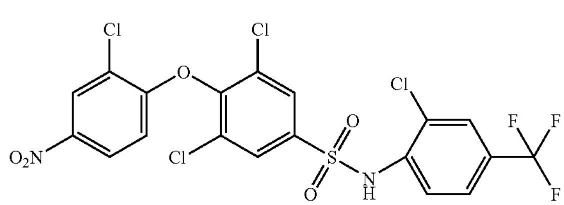 | 3,5-dichloro-4-(2-chloro-4-nitrophenoxy)-N-[2-chloro-4-(trifluoromethyl)phenyl]benzenesulfonamide |

| Example | Structure | Names |
|---|---|---|
| 241 | 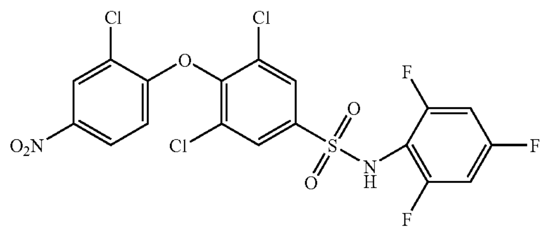 | 3,5-dichloro-4-(2-chloro-4-nitrophenoxy)-N-(2,4,6-trifluorophenyl)benzenesulfonamide |
| 242 | 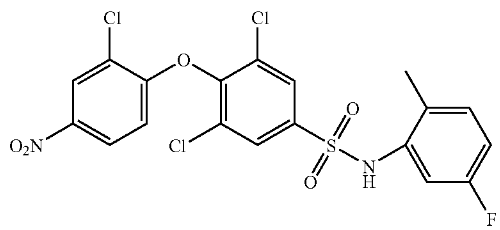 | 3,5-dichloro-4-(2-chloro-4-nitrophenoxy)-N-(5-fluoro-2-methylphenyl)benzenesulfonamide |
| 243 | 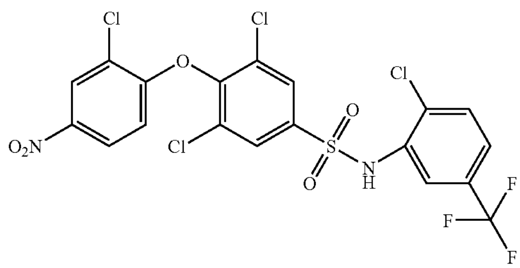 | 3,5-dichloro-4-(2-chloro-4-nitrophenoxy)-N-[2-chloro-5-(trifluoromethyl)phenyl]benzenesulfonamide |
| 244 | 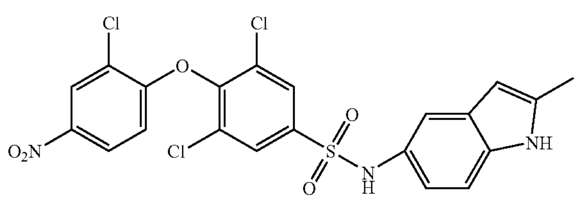 | 3,5-dichloro-4-(2-chloro-4-nitrophenoxy)-N-(2-methyl-1H-indol-5-yl)benzenesulfonamide |
| 245 | 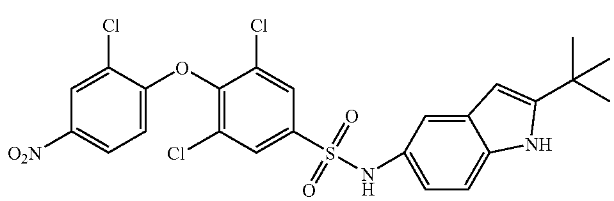 | N-(2-tert-butyl-1H-indol-5-yl)-3,5-dichloro-4-(2-chloro-4-nitrophenoxy)benzenesulfonamide |
| 246 | 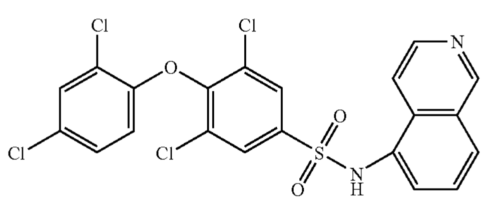 | 3,5-dichloro-4-(2,4-dichlorophenoxy)-N-isoquinolin-5-ylbenzenesulfonamide |
| 247 | 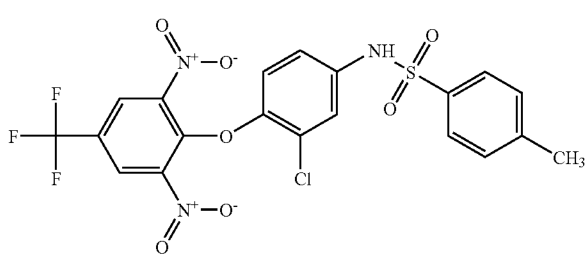 | N-{3-chloro-4-[2,6-dinitro-4-(trifluoromethyl)phenoxy]phenyl}-4-methylbenzenesulfonamide |

-continued

| Example | Structure | Names |
|---|---|---|
| 248 | 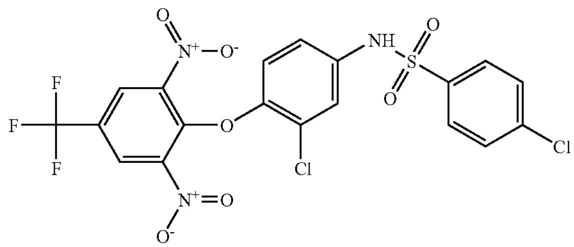 | 4-chloro-N-{3-chloro-4-[2,6-dinitro-4-(trifluoromethyl)phenoxy]phenyl}benzenesulfonamide |
| 249 | 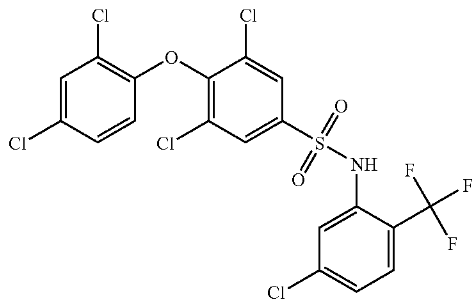 | 3,5-dichloro-N-[5-chloro-2-(trifluoromethyl)phenyl]4-(2,4-dichlorophenoxy)benzenesulfonamide |
| 250 | 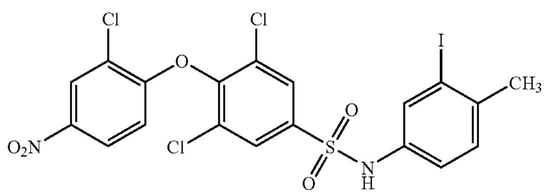 | 3,5-dichloro-4-(2-chloro-4-nitrophenoxy)-N-(3-iodo-4-methylphenyl)benzenesulfonamide |
| 251 | 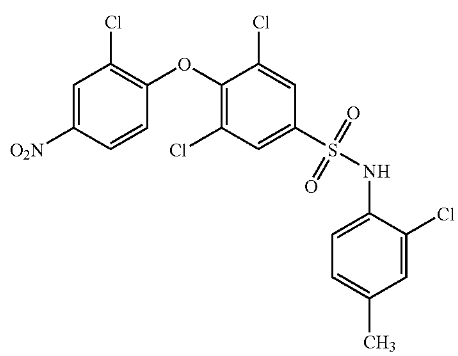 | 3,5-dichloro-N-(2-chloro-4-methylphenyl)-4-(2-chloro-4-nitrophenoxy)benzenesulfonamide |
| 252 | 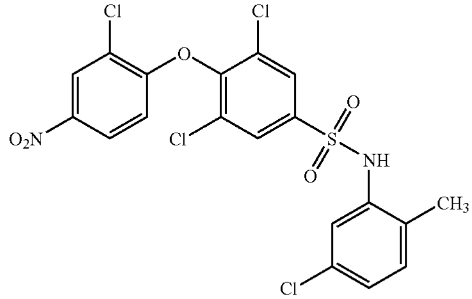 | 3,5-dichloro-N-(5-chloro-2-methylphenyl)-4-(2-chloro-4-nitrophenoxy)benzenesulfonamide |

-continued

| Example | Structure | Names |
| --- | --- | --- |
| 253 | 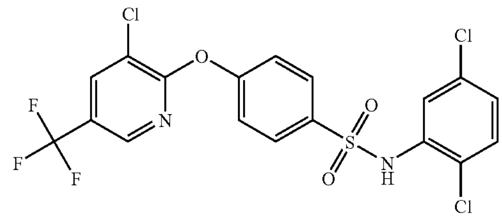 | 4-{[3-chloro-5-(trifluoromethyl)pyridin-2-yl]oxy}-N-(2,5-dichlorophenyl)benzenesulfonamide |
| 254 | 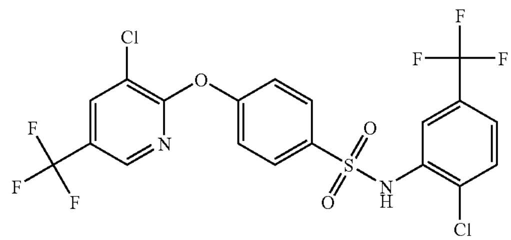 | N-[2-chloro-5-(trifluoromethyl)phenyl]-4-{[3-chloro-5-(trifluoromethyl)pyridin-2-yl]oxy}benzenesulfonamide |
| 255 | 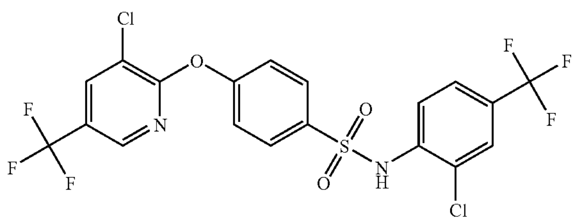 | N-[2-chloro-4-(trifluoromethyl)phenyl]-4-{[3-chloro-5-(trifluoromethyl)pyridin-2-yl]oxy}benzenesulfonamide |
| 256 | 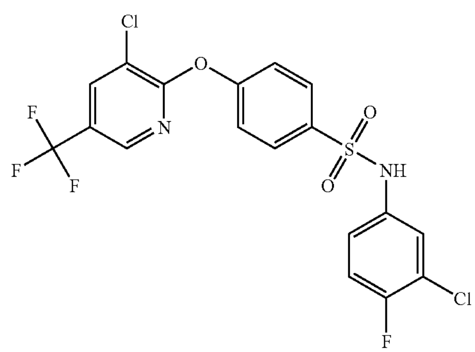 | N-(3-chloro-4-fluorophenyl)-4-{[3-chloro-5-(trifluoromethyl)pyridin-2-yl]oxy}benzenesulfonamide |
| 257 | 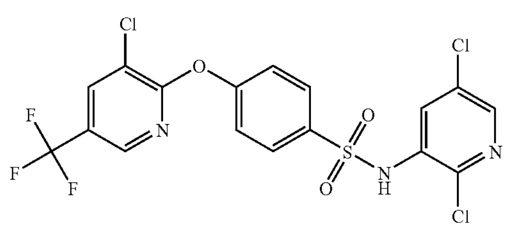 | 4-{[3-chloro-5-(trifluoromethyl)pyridin-2-yl]oxy}-N-(2,5-dichloropyridin-3-yl)benzenesulfonamide |
| 258 | 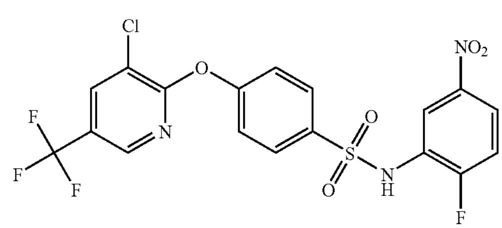 | 4-{[3-chloro-5-(trifluoromethyl)pyridin-2-yl]oxy}-N-(2-fluoro-5-nitrophenyl)benzenesulfonamide |

| Example | Structure | Names |
|---|---|---|
| 259 | 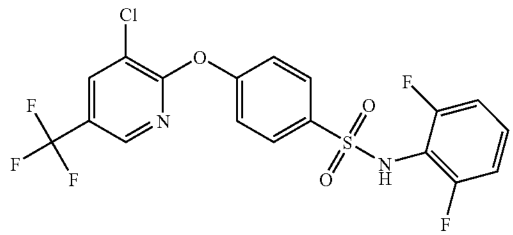 | 4-{[3-chloro-5-(trifluoromethyl)pyridin-2-yl]oxy}-N-(2,6-difluorophenyl)benzene-sulfonamide |
| 260 | 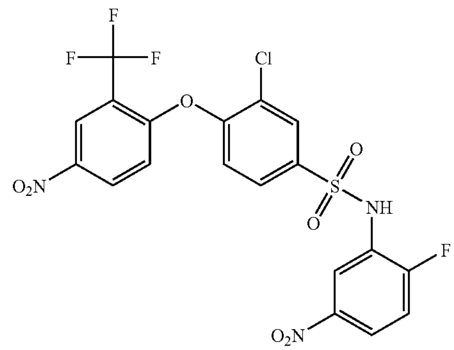 | 3-chloro-N-(2-fluoro-5-nitrophenyl)-4-[4-nitro-2-(trifluoromethyl)phenoxy]benzene-sulfonamide |
| 261 | 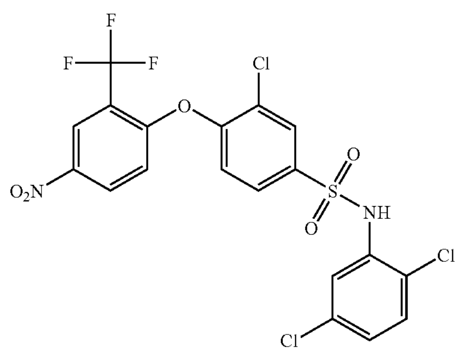 | 3-chloro-N-(2,5-dichlorophenyl)-4-(4-nitro-2-(trifluoromethyl)phenoxy]benzene-sulfonamide |
| 262 | 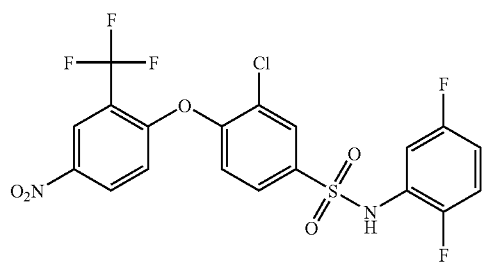 | 3-chloro-N-(2,5-difluorophenyl)-4-[4-nitro-2-(trifluoromethyl)phenoxy]benzene-sulfonamide |
| 263 | 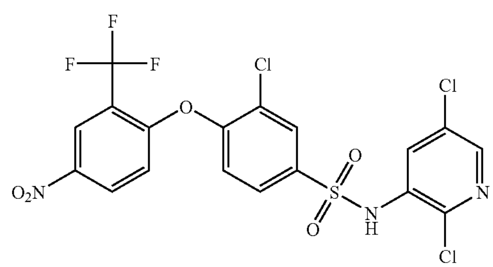 | 3-chloro-N-(2,5-dichloropyridin-3-yl)-4-[4-nitro-2-(trifluoromethyl)phenoxy]benzene-sulfonamide |

-continued

| Example | Structure | Names |
|---|---|---|
| 264 | 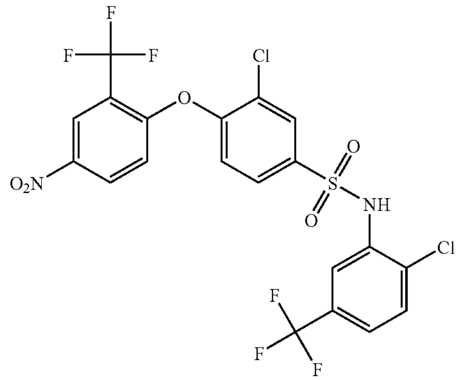 | 3-chloro-N-[2-chloro-5-(trifluoromethyl) phenyl]-4-[4-nitro-2-(trifluoromethyl) phenoxy]benzenesulfonamide |
| 265 | 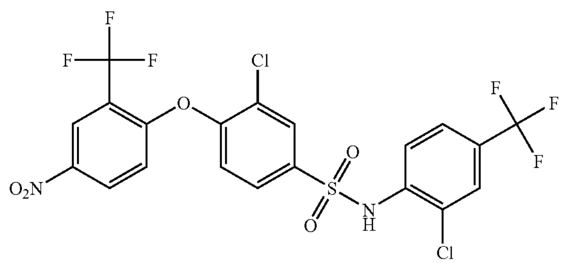 | 3-chloro-N-[2-chloro-4-(trifluoromethyl) phenyl]-4-[4-nitro-2-(trifluoromethyl) phenoxy]benzenesulfonamide |
| 266 | 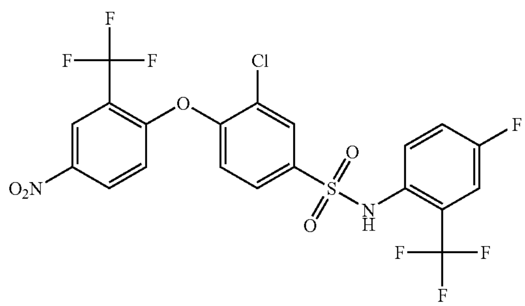 | 3-chloro-N-[4-fluoro-2-(trifluoromethyl) phenyl]-4-[4-nitro-2-(trifluoromethyl) phenoxy]benzenesulfonamide |
| 267 | 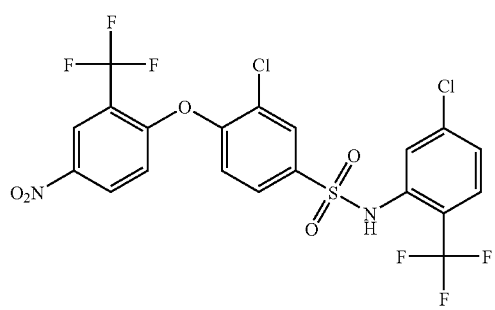 | 3-chloro-N-[5-chloro-2-(trifluoromethyl) phenyl]-4-[4-nitro-2-(trifluoromethyl) phenoxy]benzenesulfonamide |
| 268 | 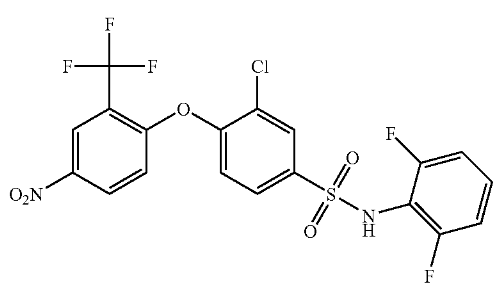 | 3-chloro-N-(2,6-difluorophenyl)-4-[4-nitro-2-(trifluoromethyl)phenoxy]benzene-sulfonamide |

-continued

| Example | Structure | Names |
| --- | --- | --- |
| 269 | 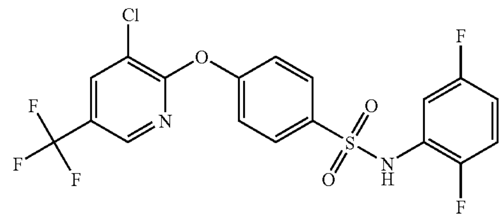 | 4-{[3-chloro-5-(trifluoromethyl)pyridin-2-yl]oxy}-N-(2,5-difluorophenyl)benzenesulfonamide |
| 270 | 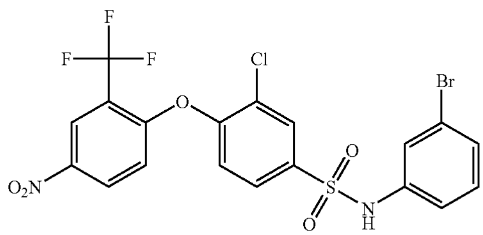 | N-(3-bRomophenyl)-3-chloro-4-[4-nitro-2-(trifluoromethyl)phenoxy]benzenesulfonamide |
| 271 | 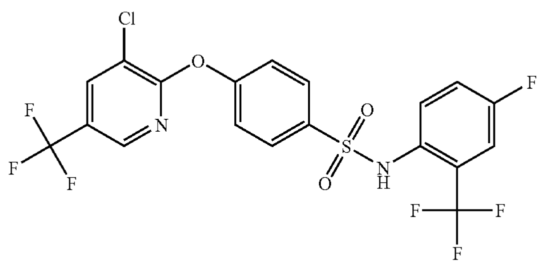 | 4-{[3-chloro-5-(trifluoromethyl)pyridin-2-yl]oxy}-N-[4-fluoro-2-(trifluoromethyl)phenyl]benzenesulfonamide |
| 272 | 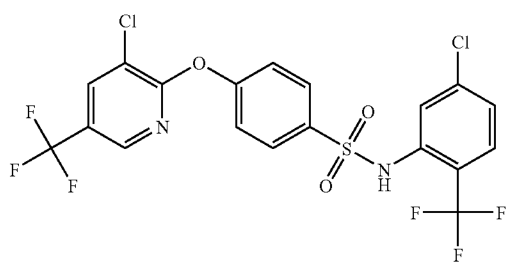 | N-[5-chloro-2-(trifluoromethyl)phenyl]-4-{[3-chloro-5-(trifluoromethyl)pyridin-2-yl]oxy}benzenesulfonamide |
| 273 | 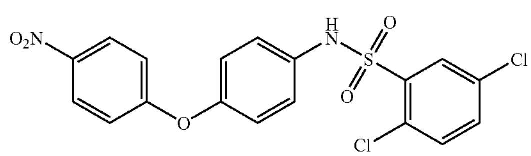 | 2,5-dichloro-N-[4-(4-nitrophenoxy)phenyl]benzenesulfonamide |
| 274 | 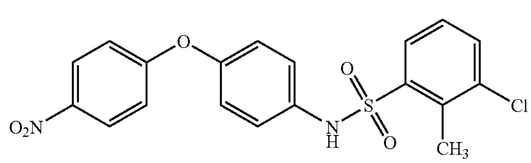 | 3-chloro-2-methyl-N-[4-(4-nitrophenoxy)phenyl]benzenesulfonamide |
| 275 | 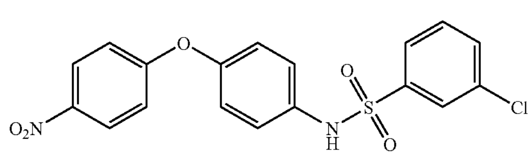 | 3-chloro-N-[4-(4-nitrophenoxy)phenyl]benzenesulfonamide |

-continued

| Example | Structure | Names |
|---|---|---|
| 276 | 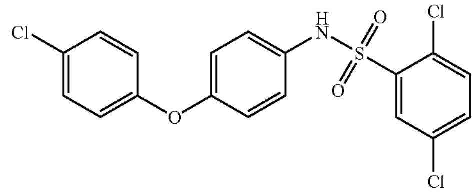 | 2,5-dichloro-N-[4-(4-chlorophenoxy)phenyl]benzenesulfonamide |
| 277 | 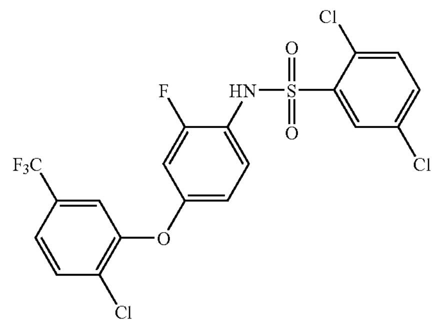 | 2,5-dichloro-N-{4-[2-chloro-5-(trifluoromethyl)phenoxy]-2-fluorophenyl}benzenesulfonamide |
| 278 | 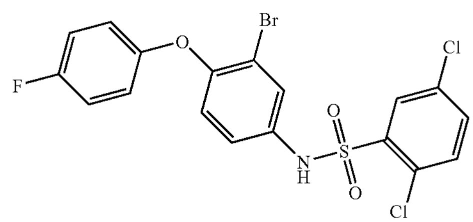 | N-[3-bRomo-4-(4-fluorophenoxy)phenyl]-2,5-dichlorobenzenesulfonamide |
| 279 | 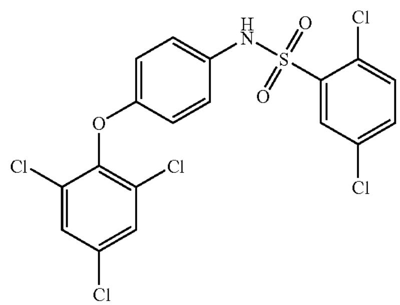 | 2,5-dichloro-N-[4-(2,4,6-trichlorophenoxy)phenyl]benzenesulfonamide |
| 280 | 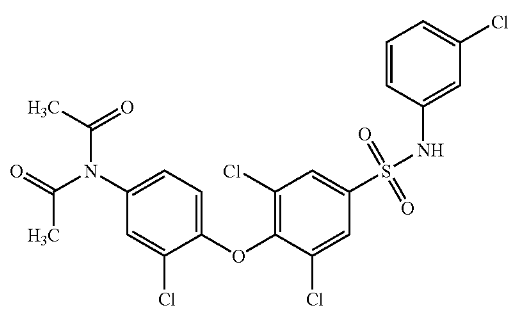 | N-acetyl-N-[3-chloro-4-(2,6-dichloro-4-{[(3-chlorophenyl)amino]sulfonyl}phenoxy)phenyl]acetamide |
| 281 | 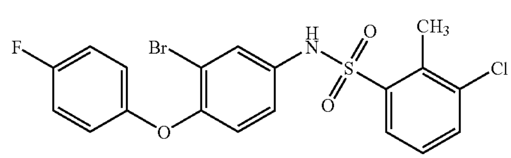 | N-[3-bRomo-4-(4-fluorophenoxy)phenyl]-3-chloro-2-methylbenzenesulfonamide |

-continued

| Example | Structure | Names |
|---|---|---|
| 282 | 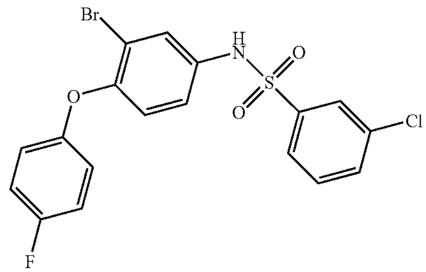 | N-[3-bRomo-4-(4-fluorophenoxy)phenyl]-3-chlorobenzenesulfonamide |
| 283 | 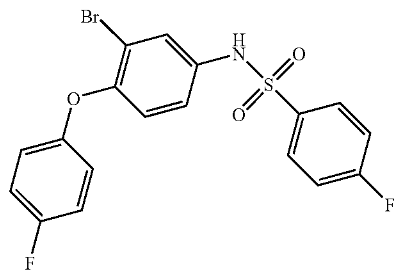 | N-[3-bRomo-4-(4-fluorophenoxy)phenyl]-4-fluorobenzenesulfonamide |
| 284 | 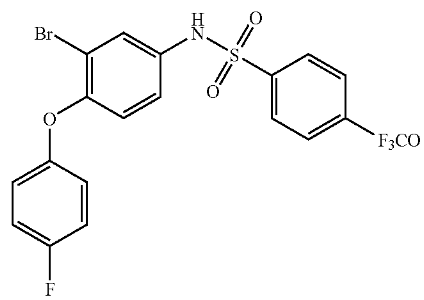 | N-[3-bRomo-4-(4-fluorophenoxy)phenyl]-4-(trifluoromethoxy)benzenesulfonamide |
| 285 | 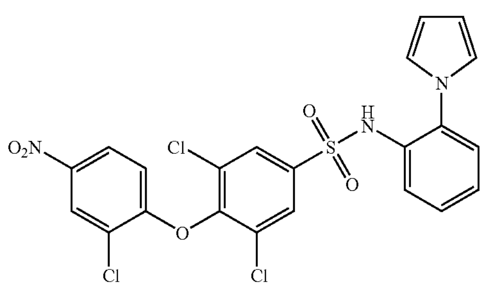 | 3,5-dichloro-4-(2-chloro-4-nitrophenoxy)-N-[2-(1H-pyRRol-1-yl)phenyl]benzene-sulfonamide |
| 286 | 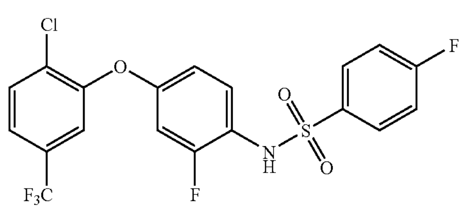 | N-{4-[2-chloro-5-(trifluoromethyl)phenoxy]-2-fluorophenyl)-4-fluorobenzenesulfonamide |
| 287 | 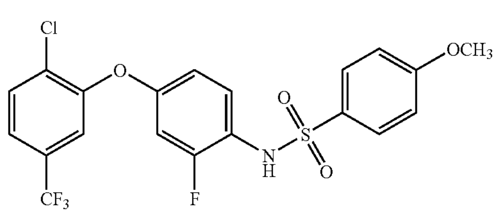 | N-{4-[2-chloro-5-(trifluoromethyl)phenoxy]-2-fluorophenyl)-4-methoxybenzenesulfonamide |

-continued

| Example | Structure | Names |
|---|---|---|
| 288 | 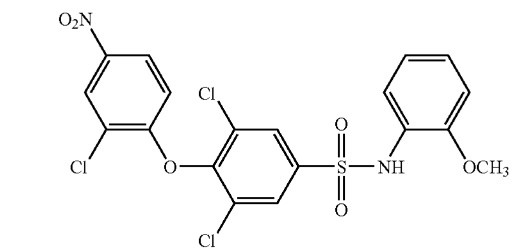 | 3,5-dichloro-4-(2-chloro-4-nitrophenoxy)-N-[2-(trifluoromethoxy)phenyl]benzene-sulfonamide |
| 289 | 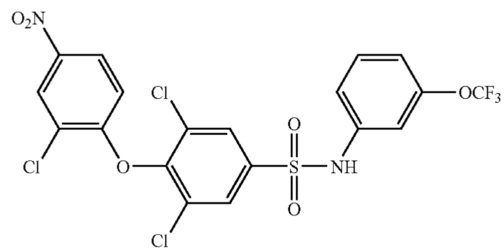 | 3,5-dichloro-4-(2-chloro-4-nitrophenoxy)-N-[3-(trifluoromethoxy)phenyl]benzene-sulfonamide |
| 290 | 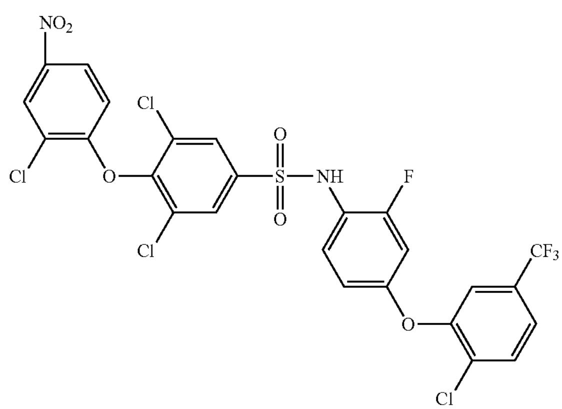 | 3,5-dichloro-4-(2-chloro-4-nitrophenoxy)-N-{4-[2-chloro-5-(trifluoromethyl)phenoxy]-2-fluorophenyl}benzenesulfonamide |
| 291 | 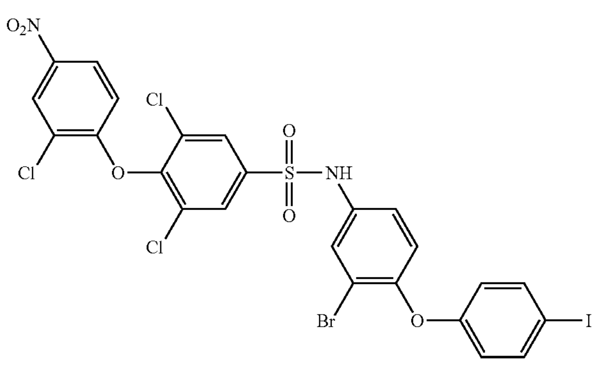 | N-[3-bRomo-4-(4-fluorophenoxy)phenyl]-3,5-dichloro-4-(2-chloro-4-nitrophenoxy)benzenesulfonamide |
| 292 | 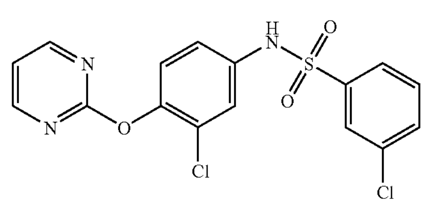 | 3-chloro-N-[3-chloro-4-(pyRimidin-2-yloxy)phenyl]benzenesulfonamide |

-continued

| Example | Structure | Names |
|---|---|---|
| 293 | 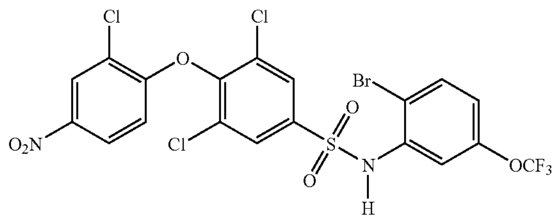 | N-(2-bromo-5-(trifluoromethoxy)phenyl)-3,5-dichloro-4-(2-chloro-4-nitrophenoxy)benzenesulfonamide |
| 294 | 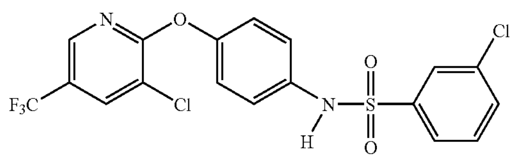 | 3-chloro-N-(4-(3-chloro-5-(trifluoromethyl)pyridin-2-yloxy)phenyl)benzenesulfonamide |
| 295 | 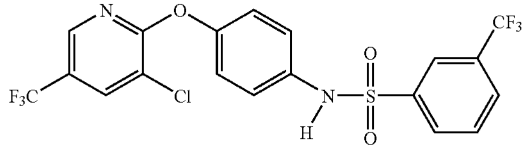 | N-(4-(3-chloro-5-(trifluoromethyl)pyridin-2-yloxy)phenyl)-3-(trifluoromethyl)benzenesulfonamide |
| 296 | 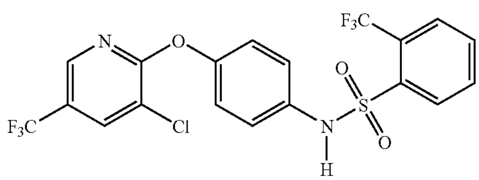 | N-(4-(3-chloro-5-(trifluoromethyl)pyridin-2-yloxy)phenyl)-2-(trifluoromethyl)benzenesulfonamide |
| 297 | 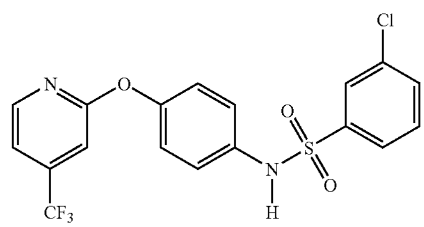 | 3-chloro-N-(4-(4-(trifluoromethyl)pyridin-2-yloxy)phenyl)benzenesulfonamide |
| 298 | 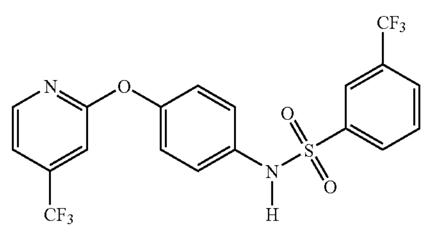 | 3-(trifluoromethyl)-N-(4-(4-(trifluoromethyl)pyridin-2-yloxy)phenyl)benzenesulfonamide |
| 299 | 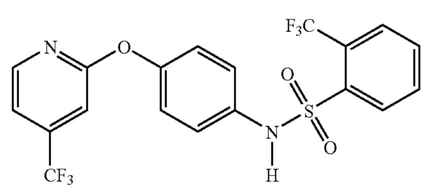 | 2-(trifluoromethyl)-N-(4-(4-(trifluoromethyl)pyridin-2-yloxy)phenyl)benzenesulfonamide |
| 300 | 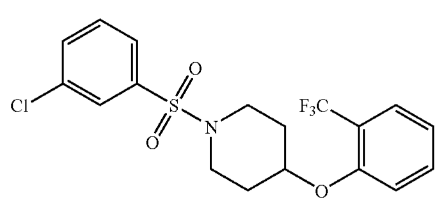 | 1-(3-chlorophenylsulfonyl)-4-(2-(trifluoromethyl)phenoxy)piperidine |

-continued

| Example | Structure | Names |
|---|---|---|
| 301 | 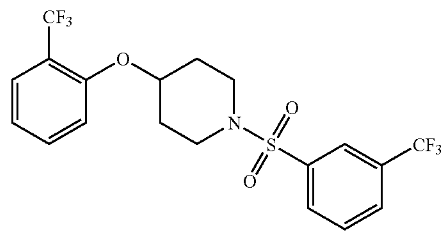 | 4-(2-(trifluoromethyl)phenoxy)-1-(3-(trifluoromethyl)phenylsulfonyl)piperidine |
| 302 | 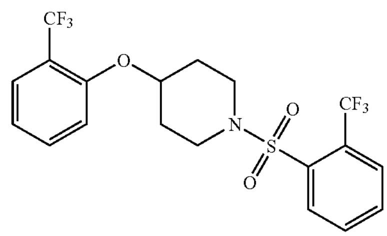 | 4-(2-(trifluoromethyl)phenoxy)-1-(2-(trifluoromethyl)phenylsulfonyl)piperidine |
| 303 | 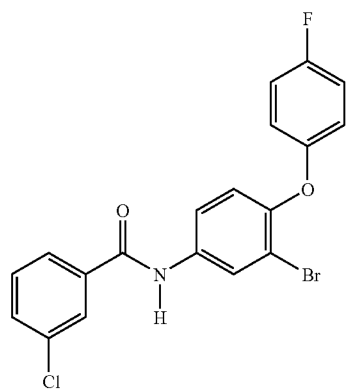 | N-(3-bromo-4-(4-fluorophenoxy)phenyl)-3-chlorobenzamide |
| 304 | 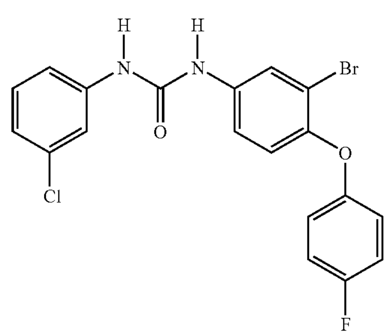 | 1-(3-bromo-4-(4-fluorophenoxy)phenyl)-3-(3-chlorophenyl)urea |
| 305 | 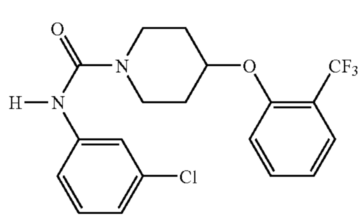 | N-(3-chlorophenyl)-4-(2-(trifluoromethyl)phenoxy)piperidine-1-carboxamide |

| Example | Structure | Names |
|---|---|---|
| 306 | 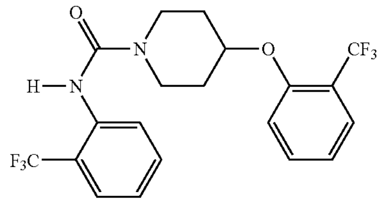 | 4-(2-(trifluoromethyl)phenoxy)-N-(2-(trifluoromethyl)phenyl)piperidine-1-carboxamide |
| 307 | 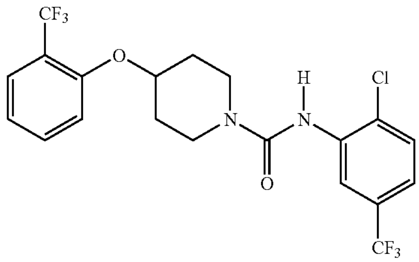 | N-(2-chloro-5-(trifluoromethyl)phenyl)-4-(2-(trifluoromethyl)phenoxy)piperidine-1-carboxamide |
| 308 | 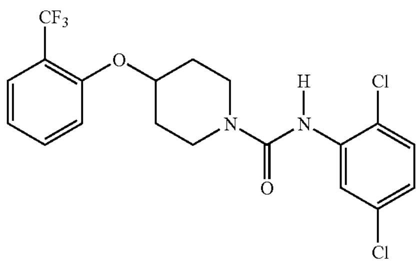 | N-(2,5-dichlorophenyl)-4-(2-(trifluoromethyl)phenoxy)piperidine-1-carboxamide |
| 309 | 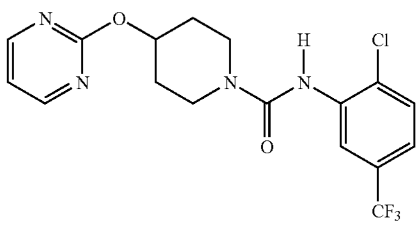 | N-(2-chloro-5-(trifluoromethyl)phenyl)-4-(pyrimidin-2-yloxy)piperidine-1-carboxamide |
| 310 | 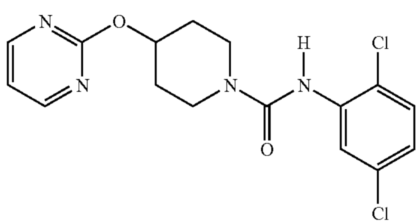 | N-(2,5-dichlorophenyl)-4-(pyrimidin-2-yloxy)piperidine-1-carboxamide |

Pharmaceutical Compositions

In a second aspect, the invention provides pharmaceutical compositions comprising an inhibitor of ubiquitination according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain preferred embodiments, compounds of the invention are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, flavors, dyes and other materials well known in the art. The preparation of pharmaceutically acceptable formulations is described in many well known references to one skilled in the art, for example, Remington's Pharmaceutical Sciences, 18th Edition, ed. A. Gennaro, Mack Publishing Co., Easton, Pa., 1990.

As used herein, the term pharmaceutically acceptable salts refers to salts that retain the desired biological activity of the compounds of the invention and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). Moreover, the compounds of the invention can also be administered as prodrugs which can be converted to the active form in vivo.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 500 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Inhibition of Ubiquitination

In a third aspect, the invention provides a method of inhibiting ubiquitination in a cell, comprising contacting a cell in which inhibition of ubiquitination is desired with an inhibitor of ubiquitination of the invention.

Measurement of the ubiquitination can be achieved using known methodologies that one skilled in the art would readily know where to find them.

Preferably, the method according to the third aspect of the invention causes an inhibition of cell proliferation of contacted cells. The phrase "inhibiting cell proliferation" is used to denote an ability of an inhibitor of ubiquitination to retard the growth of cells contacted with the inhibitor as compared to cells not contacted. An assessment of cell proliferation can be made by counting contacted and non-contacted cells using a Coulter Cell Counter (Coulter, Miami, Fla.), photographic analysis with Array Scan II (Cellomics) or a hemacytometer. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the inhibitor is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, an inhibitor of ubiquitination according to the invention that inhibits cell proliferation in a contacted cell may induce the contacted cell to undergo growth retardation, to undergo growth arrest, to undergo programmed cell death (i.e., to apoptose), or to undergo necrotic cell death.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the ubiquitination inhibitor induces cell differentiation in the contacted cell. Thus, a neoplastic cell, when contacted with an inhibitor of ubiquitination may be induced to differentiate, resulting in the production of a non-neoplastic daughter cell that is phylogenetically more advanced than the contacted cell.

Treatment for Cell Proliferative Diseases or Conditions

In some preferred embodiments, the contacted cell is in an animal. Thus, in a fourth aspect the invention provides a method for treating a cell proliferative disease or condition in an animal, comprising administering to an animal in need thereof an effective amount of an inhibitor of ubiquitination of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a ubiquitination inhibitor of the invention. Most preferably, the invention provides a method for treating cancer comprising administering to a patient in need thereof an effective amount of an inhibitor of ubiquitination of the invention.

The term "therapeutically effective amount" is meant to denote a dosage sufficient to cause inhibition of ubiquitination in the cells of the subject, or a dosage sufficient to inhibit cell proliferation or to induce cell differentiation in the subject. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

When administered systemically, the ubiquitination inhibitor is preferably administered at a sufficient dosage to attain a blood level of the inhibitor from about 0.01 µM to about 100 µM, more preferably from about 0.05 µM to about 50 µM, still more preferably from about 0.1 µM to about 25 µM, and still yet more preferably from about 0.5 µM to about 20 µM. For localized administration, much lower concentrations than this may be effective, and much higher concentrations may be tolerated. One of skill in the art will appreciate that the dosage of ubiquitination inhibitor necessary to produce a therapeutic effect may vary considerably depending on the tissue, organ, or the particular animal or patient to be treated.

The following examples are intended to further illustrate certain preferred embodiments of the invention, and are not intended to limit the scope of the invention.

General Synthetic Procedure

The compounds of the invention can be prepared according to the reaction schemes illustrated below utilizing methods known to one of ordinary skill in the art. These schemes serve to exemplify some procedures that can be used to make the compounds of the invention. One skilled in the art will recognize that other general synthetic procedures may be used. The starting components are readily prepared from benzene and phenols to which any kind of substitutions can be made according to procedures well known to those skilled in the art and commercially available.

As illustrated in Scheme 1, the synthesis of the compounds of the invention may start with the formation of the ether 3 via a Williamson synthesis by the reaction of the phenol 2 with the substituted fluorophenyl 1. The reactant 1 may be any halogenated aryl component or any other aryl compound capable of transferring the aryl group to the phenoxide formed from 2. Compound 3 can be converted to compound 4 via a sulfonation reaction in the presence of $ClSO_3H$. The formation of the sulfonamide 5 is achieved by reaction of the amine 5 with the compound 4.

Scheme 2 illustrates the general procedure for the synthesis of the compounds of the invention that have various $R^1$ and $R^2$ groups bound to the nitrogen of the sulfonamide moiety of compound 6 of Scheme 1. The sulfonamide 9 is reacted with the boronic acid of compound 10 in the presence of $Cu(OAC)_2$ to yield the sulfonamide 11. One skilled in the art will recognize that any $R^1$ and $R^2$ groups may be bound to the nitrogen of the solfonamide moiety by varying the identity of the boronic acid of compound 10.

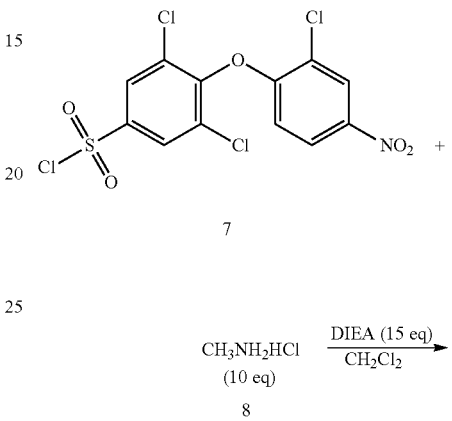

SCHEME 2

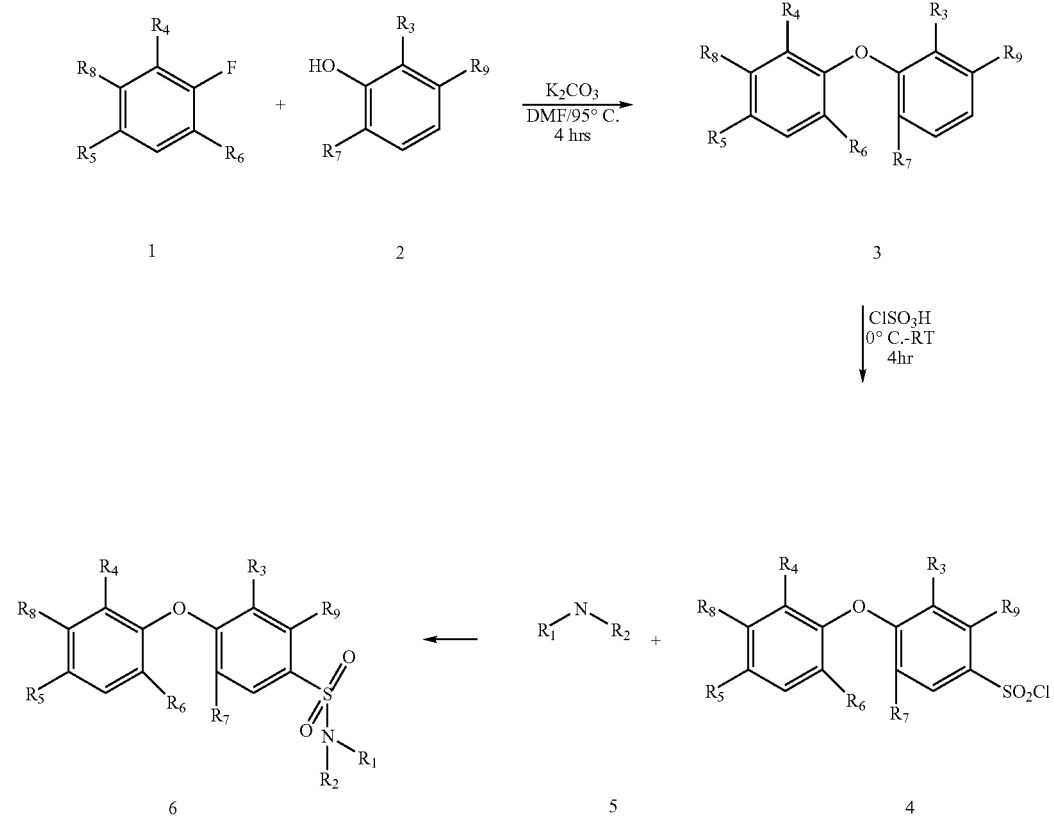

SCHEME 1

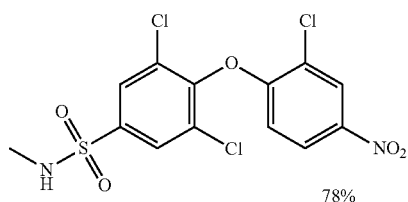

78%

9

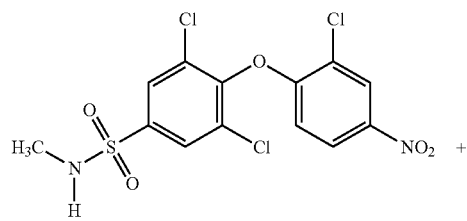

9

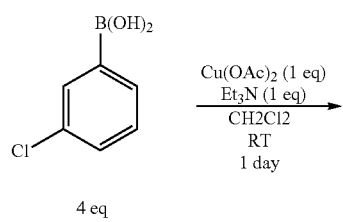

10

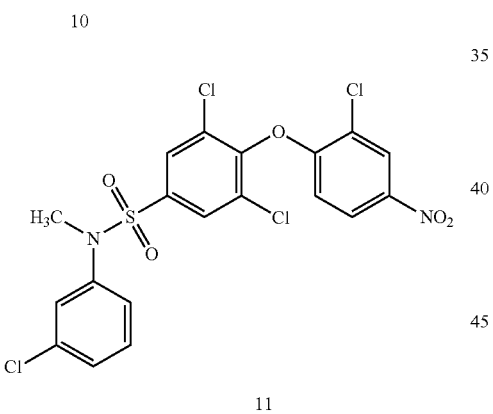

11

Procedure for the Synthesis of 3,5-dichloro-4-(2-chloro-4-nitrophenoxy)-N-(3-chlorophenyl)-N-methylbenzenesulfonamide (153) (Scheme 2)

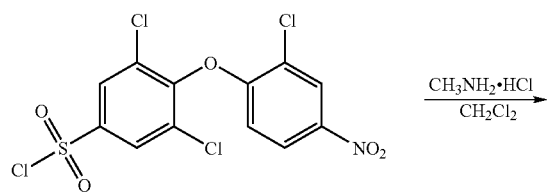

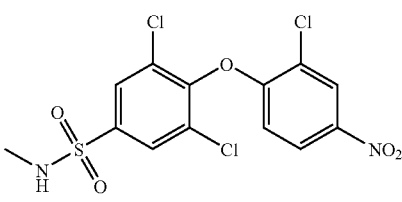

Step 1. Methyl amine hydrochloride (0.40 g, 6.0 mmol), 4-(2-chloro-4-nitrophenoxy)-3,5-dichloro-benzenesulfonyl chloride (0.25 g, 0.6 mmol), and N,N-diisopropylethylamine (1.6 mL, 9.2 mmol) were combined in dichloromethane (25 mL) and stirred at room temperature overnight. The mixture was diluted with dichloromethane and rinsed successively with 1N HCl, H$_2$O, NaHCO3 (sat.), and brine. The organic fraction was dried over MgSO4, filtered and concentrated to produce the sulfonamide (194 mg, 78%), which was used without purification for step 2.

Step 2. To a suspension of 3-chlorophenylboronic acid (19 mg, 0.12 mmol), Cu(OAc)$_2$ (24 mg, 0.12 mmol), and triethylamine (20 μL, 0.12 mmol) in dichloromethane (2 mL) was added the product from step 1 (50 mg, 0.12 mmol). The reaction was allowed to proceed with monitoring by TLC (1:3 ethyl acetate:hexanes) for 1 hour at which time additional 3-chloroboronic acid (57 mg, 0.36 mmol), and triethylamine (60 μL, 0.36 mmol) were added. After proceeding overnight, the mixture was diluted with dichloromethane and rinsed successively with 1N HCl, H$_2$O, NaHCO$_3$ (sat.), and brine. The organic fraction was dried over MgSO$_4$, filtered and concentrated to produce the crude product which was purified by radial silica gel chromatography (1:20 to 1:3 ethyl acetate:hexanes to afford the desired product (4.2 mg, 6.7%).

3,5-dichloro-4-(2-chloro-4-nitrophenoxy)-N-(3-chlorophenyl)-N-methylbenzenesulfonamide (153)

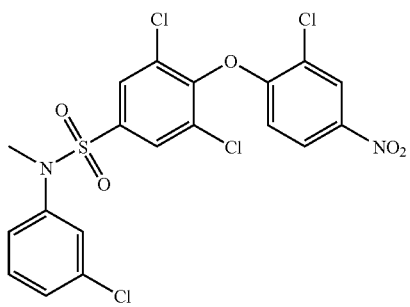

$^1$H NMR (CDCl$_3$, 300 MHz) δ 8.43 (dd, J=1.2, 2.7 Hz, 1H), 8.06 (ddd, J=0.9, 2.4, 9 Hz, 1H), 7.63 (s, 1H), 7.62 (s, 1H), 7.34-7.32 (m, 2H), 7.14-7.13 (m, 1H), 7.11-7.07 (m, 1H), 6.51 (dd, J=0.9, 9 Hz, 1H), 3.26 (s, 3H).
LCMS purity 98%. MS Found 521 (MH$^+$).

3,5-dichloro-4-(2-chloro-4-nitrophenoxy)-N-[3-(methylsulfonyl)phenyl]benzenesulfonamide (173)

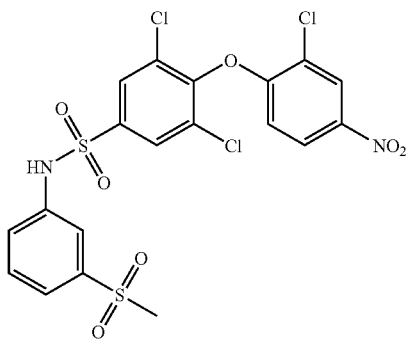

This compound was prepared according to the procedure for step 2 of the preparation of 153.
$^1$H NMR (CD$_3$OD, 300 MHz) δ 8.46 (d, J=2.7 Hz, 1H), 8.12 (dd, J=3, 9.3 Hz, 1H), 7.92 (s, 2H), 7.74 (app dt, J=1.5, 7.5 Hz, 1H), 7.64-7.60 (m, 3H), 6.70 (d, J=9.3 Hz, 1H), 3.10 (s, 3H).
LCMS purity 93%. MS (Negative ion) Found 549 (M-H$^+$).

3,5-dichloro-N-(5-chloro-2-methoxyphenyl)-(2-chloro-4-nitrophenoxy)lbenzenesulfonamide (164)

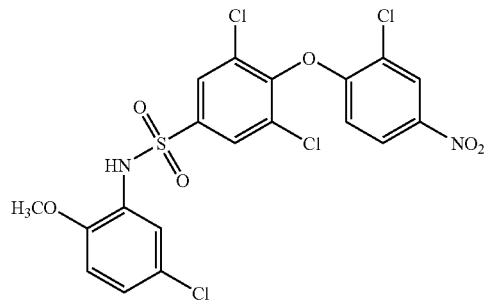

This compound was prepared according to the procedure for the preparation of 153
$^1$H NMR (CDCl$_3$, 300 MHz) δ 8.41 (d, J=2.7 Hz, 1H), 8.03 (dd, J=3, 9.3 Hz, 1H), 7.86 (s, 2H), 7.54 (d, J=2.4 Hz, 1H), 7.11 (dd, J=2.7, 8.7 Hz, 1H), 7.06 (s, 1H), 6.76 (d, J=8.7 Hz, 1H), 6.46 (d, J=9 Hz, 1H), 3.78 (s, 3H).
MS (negative ion) Found 535 (M-H$^+$).

3,5-dichloro-4-(2-chloro-4-nitrophenoxy)-N-(3,4-dichlorophenyl)benzenesulfonamide (167)

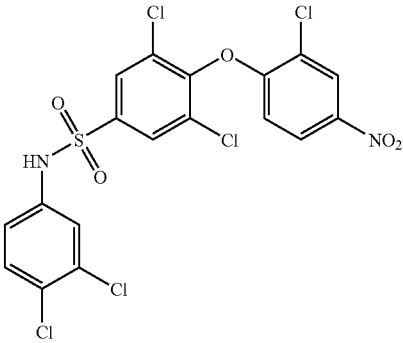

This compound was prepared according to the procedure for step 2 of the preparation of 153.
$^1$H NMR (CDCl$_3$, 300 MHz) δ 8.42 (d, J=2.7 Hz, 1H), 8.05 (dd, J=2.7, 9.3 Hz, 1H), 7.86 (s, 2H), 7.42 (d, J=8.7 Hz, 1H), 7.03 (dd, J=2.4, 8.7 Hz, 1H), 6.85 (br s, 1H), 6.49 (d, J=9 Hz, 1H).
LCMS purity 92%. MS (negative ion) Found 539 (M-H$^+$).

Procedure for the Synthesis of 3,5-dichloro-4-(2-chloro-4-nitrophenoxy)-N-(3-chlorophenyl)benzenesulfonamide (154)

A solution of 3-chloroaniline (38 µL, 0.35 mmol) and 4-(2-chloro-4-nitrophenoxy)-3,5-dichloro-benzenesulfonyl chloride (100 mg, 0.24 mmol), was stirred in pyridine (2 mL) at room temperature for three days. The reaction mixture was concentrated by rotary evaporator and dissolved in dichloromethane. The solution was washed successively with 1N HCl, and NaHCO$_3$ (sat.)/brine. The organic fraction was dried over MgSO$_4$, filtered, and concentrated. The compound was purified by radial silica gel chromatography (1:20 to 1:1 ethyl acetate:hexanes) to afford the product which was subsequently freeze-dried from H₂O/acetonitrile to produce a white solid which was 97% pure by LCMS analysis (67 mg, 55%).

3,5-dichloro-4-(2-chloro-4-nitrophenoxy)-N-(3-chlorophenyl)benzenesulfonamide (154)

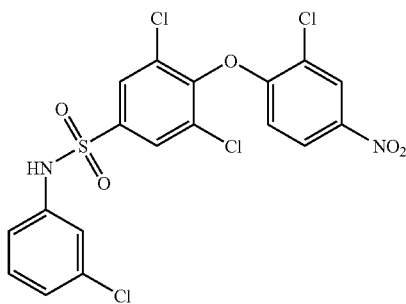

$^1$H NMR (DMSO-d$_6$, 300 MHz) δ 8.50 (dd, J=0.6, 2.7 Hz, 1H), 8.08 (ddd, J=0.9, 2.7, 9.3 Hz, 1H), 7.99 (s, 1H), 7.98 (s, 1H), 7.33 (app t, J=8 Hz, 1H), 7.21-7.09 (m, 3H), 6.94 (dd, J=0.9, 9 Hz, 1H).

LCMS purity 97%. MS (negative ion) Found 505 (M-H$^+$).

Procedure for the Synthesis of 2,5-dichloro-N-[4-(4-nitrophenoxy)phenyl]benzene sulfonamide (273)

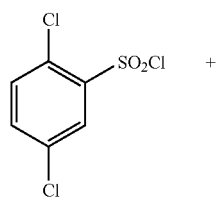

+

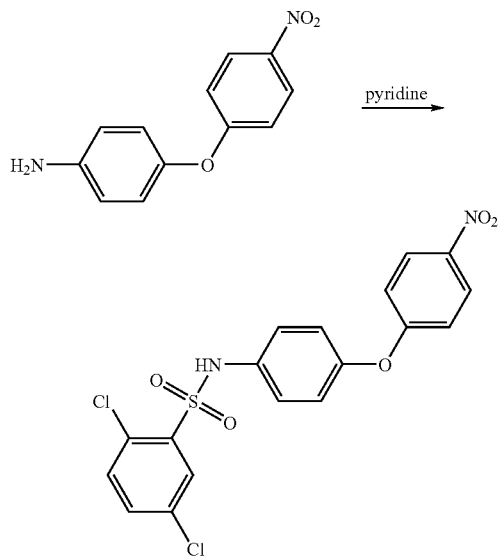

A solution of 444-nitrophenoxy)aniline (55 mg, 0.24 mmol) and 2,5-dichlorophenylsulfonyl chloride (29 mg, 0.12 mmol) was stirred in pyridine (2 mL) at room temperature overnight. The reaction mixture was concentrated by rotary evaporator and dissolved in dichloromethane. The solution was washed successively with 1N HCl, and NaHCO3 (sat.)/brine. The organic fraction was dried over MgSO₄, filtered, and concentrated. The compound was purified by radial silica gel chromatography (1:20 to 1:1 ethyl acetate:hexanes) to afford the product as an oil which was 94% pure by LCMS analysis (5 mg, 9%).

2,5-dichloro-N-[4-(4-nitrophenoxy)phenyl]benzene-sulfonamide (273)

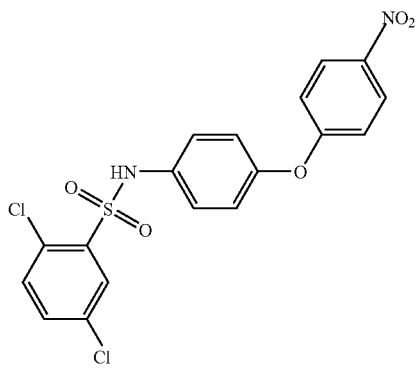

$^1$H NMR (DMSO-d$_6$, 300 MHz) δ 8.19 (d, J=9.3 Hz, 2H), 7.95 (d, J=2.4 Hz, 1H), 7.75-7.67 (m, 2H), 7.18-7.00 (m, 6H).

LCMS purity 94%. MS Found 480 (MH$^+$+CH$_3$CN). MS (negative) Found 437 (M-H$^+$).

N-[3-bromo-4-(4-fluorophenoxy)phenyl]-3-chlorobenzenesulfonamide (282)

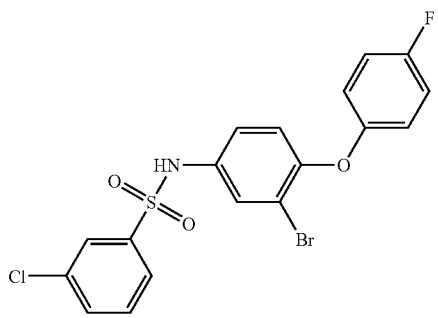

This compound was prepared according to the procedure for the preparation of 273.

$^1$H NMR (CDCl$_3$, 300 MHz) δ 7.74 (t, J=1.8 Hz, 1H), 7.63 (ddd, J=1.2, 1.5, 7.8 Hz, 1H), 7.55 (ddd, J=1.2, 1.8, 8.1 Hz, 1H), 7.43 (t, J=7.8 Hz, 1H), 7.35 (d, J=2.7 Hz, 1H), 7.05-6.87 (m, 5H), 6.77 (d, J=8.7 Hz, 1H), 6.61 (br s, 1H).

LCMS purity 98%. MS (negative ion) Found 454 (M-H$^+$).

N-{4-[2-chloro-5-(trifluoromethyl)phenoxy]-2-fluorophenyl}-4-methoxybenzenesulfonamide (287)

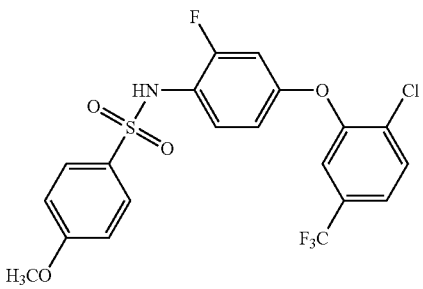

This compound was prepared according to the procedure for the preparation of 273.

$^1$H NMR (CDCl$_3$, 300 MHz) δ 7.73 (d, J=2.1 Hz, 1H), 7.68 (d, J=8.4 Hz, 2H), 7.57 (t, J=9 Hz, 1H), 7.49-7.46 (m, 1H), 6.99 (d, J=8.7 Hz, 1H), 6.90 (d, J=8.4 Hz, 2H), 6.78-6.74 (m, 1H), 6.64 (dd, J=2.7, 10.5 Hz, 1H), 6.54 (m, 1H).

LCMS purity 89%. MS (negative ion) Found 574 (M-H$^+$).

3-chloro-N-[3-chloro-4-(pyrimidin-2-yloxy)phenyl]benzenesulfonamide (292)

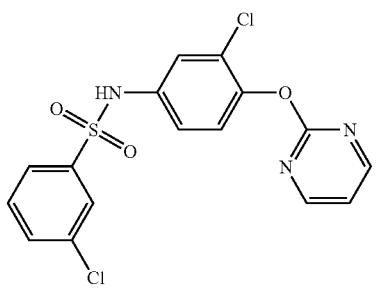

This compound was prepared according to the procedure for the preparation of 273.

$^1$H NMR (DMSO-d$_6$, 300 MHz) δ 10.70 (br s, 1H), 8.60 (d, J=5.1 Hz, 2H), 7.79-7.72 (m, 3H), 7.65-7.60 (m, 1H), 7.30-7.24 (m, 2H), 7.22 (d, J=2.7 Hz, 1H), 7.10 (dd, J=2.7, 8.7 Hz, 1H).

LCMS purity 95%. MS (negative ion) Found 394 (M-H$^+$).

3-chloro-N-(4-(3-chloro-5-(trifluoromethyl)pyridyn-2-yloxy)phenyl)benzenesulfonamide 1294)

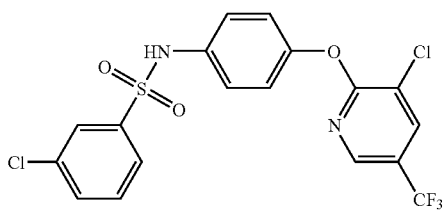

This compound was prepared according to the procedure for the preparation of 273.

$^1$H NMR (CDCl$_3$, 300 MHz) δ 8.23 (m, 1H), 7.97 (d, J=2.4 Hz, 1H), 7.77 (t, J=1.8 Hz, 1H), 7.61 (app dt, J=0.9, 7.5 Hz, 1H), 7.55-7.52 (m, 1H), 7.40 (t, J=7.8 Hz, 1H), 7.25-7.07 (m, 4H), 6.47 (s, 1H).

LCMS purity 96%. MS (negative ion) Found 461 (M-H$^+$).

N-3-bromo-4-(4-fluorophenoxy)phenyl)-3-chlorobenzenamide (303)

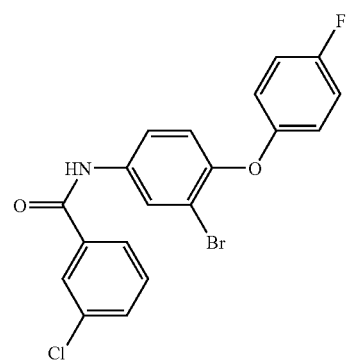

This compound was prepared in a fashion similar to the procedure for the preparation of 273 using 3-chlorobenzoyl chloride in place of the aryl sulfonyl chloride.

$^1$H NMR (DMSO-d$_6$, 300 MHz) δ 10.48 (s, 1H), 8.22 (m, 1H), 7.99 (m, 1H), 7.89 (d, J=8.1 Hz, 1H), 7.75 (d, J=8.7 Hz, 1H), 7.68-7.66 (m, 1H), 7.57 (t, J=7.5 Hz, 1H), 7.20 (app t, J=9 Hz, 2H), 7.10 (d, J=8.7 Hz, 1H), 6.99-6.94 (m, 2H).

LCMS purity 99%. MS (negative ion) Found 418 (M-H$^+$).

Procedure for the Synthesis of 1-(3-bromo-4-(4-fluorophenoxy)phenyl)-3-chlorophenyl)urea (304).

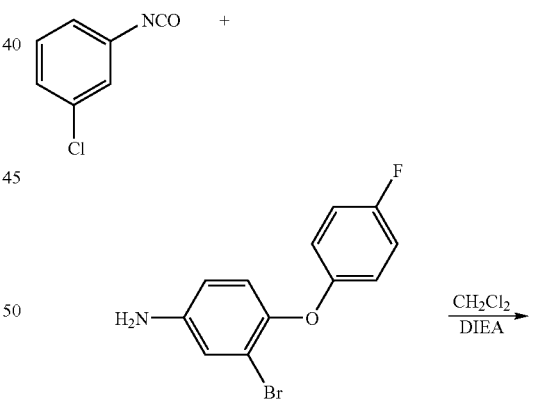

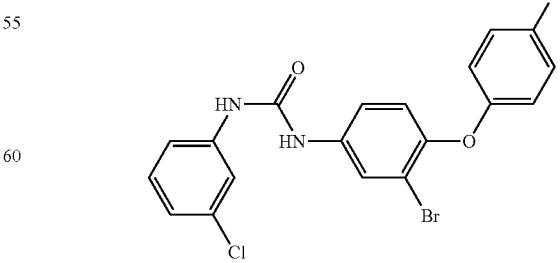

A solution of 3-bromo-4-(4-fluorophenoxy)aniline (42 mg, 0.15 mmol) and 3-chlorophenyl isocyanate (37 μL, 0.30 mmol was stirred in dichloromethane (2 mL) at room temperature for three days The resultant precipitate was filtered and washed with dichloromethane. The solid was dissolved in methanol and concentrated to afford the product, which was 98% pure by LCMS analysis (41 mg, 62%).

1-(3-bromo-4-(4-fluorophenoxy)phenyl)-3-chlorophenyl)urea (304)

$^1$H NMR (CDCl$_3$, 300 MHz) δ 7.88 (d, J=2.4 Hz, 1H), 7.61 (q, J=1.2 Hz, 1H), 7.34 (dd, J=2.4, 8.7 Hz, 1H), 7.26-7.24 (m, 2H), 7.08-6.95 (m, 4H), 6.91-6.87 (m, 2H).
LCMS purity 98%. MS Found 435 (MH$^+$).

Procedure for the Synthesis of N-(3-chlorophenyl)-4-(2-(trifluoromethyl)phenoxy)piperidine-1-carboxamide (305)

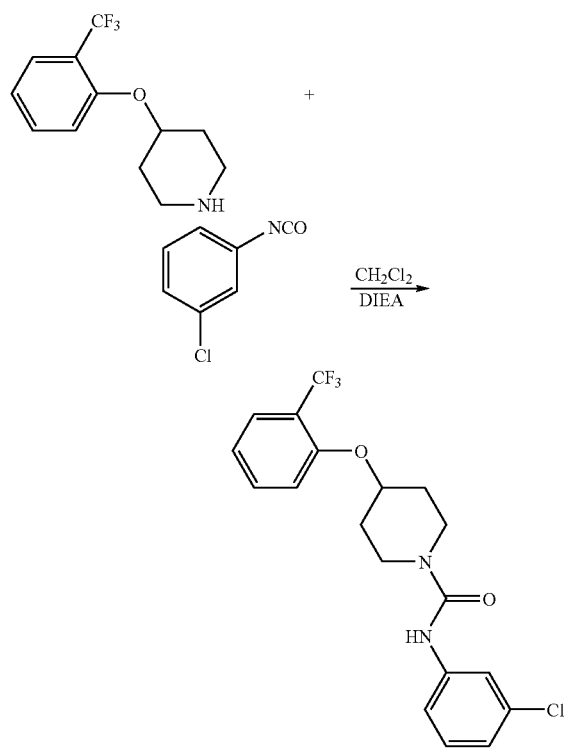

A solution of 4-(2-trifluoromethylphenoxy)piperidine hydrochloride (42 mg, 0.15 mmol), 3-chlorophenyl isocyanate (36 mg, 0.30 mmol), and N,N-diisopropylethylamine (78 μL, 0.45 mmol) was stirred in dichloromethane (2 mL) at room temperature for overnight. The reaction mixture was diluted with dichloromethane and the solution was washed successively with 1N HCl, and NaHCO$_3$ (sat.)/brine. The organic fraction was dried over MgSO$_4$, filtered, and concentrated. The compound was purified by radial silica gel chromatography (1:20 to 1:2 ethyl acetate:hexanes) to afford the product which was 98% pure by LCMS analysis (15.7 mg, 26%).

N-(3-chlorophenyl)-4-(2-(trifluoromethyl)phenoxy)piperidine-1-carboxamide (305)

$^1$H NMR (DMSO-d$_6$, 300 MHz) δ 8.71 (s, 1H), 7.63-7.57 (m, 2H), 7.38-7.32 (m, 2H), 7.23 (app t, J=8.1 Hz, 1H), 7.07 (app t, J=7.5 Hz, 1H), 6.97-6.93 (m, 1H), 4.87 (m, 1H), 3.65-3.57 (m, 2H), 3.51-3.39 (m, 2H), 1.98-1.91 (m, 2H), 1.69-1.64 (m, 2H). LCMS purity 98%. MS (negative ion) Found 397 (M-H$^+$).

N-(2,5-dichlorophenyl)-4-(pyrimidin-2-yloxy)piperidine-1-carboxamide (310)

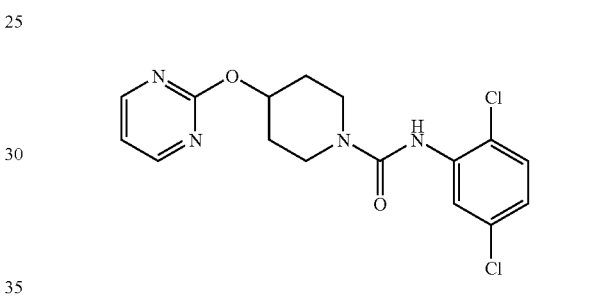

This compound was prepared according to the procedure for the preparation of compound 305.

$^1$H NMR (CDCl$_3$, 300 MHz) δ 8.52 (d, J=3.9 Hz, 2H), 8.32 (t, J=2.1 Hz, 1H), 7.26-7.22 (m, 1H), 7.07 (s, 1H), 6.97-6.90 (m, 2H), 5.31 (m, 1H), 3.87-3.81 (m, 2H), 3.59-3.52 (m, 2H), 2.12-2.10 (m, 2H), 2.02 (m, 2H).
LCMS purity 94%. MS Found 367 (MH$^+$).

Formation of the sulfonamide moieties of the compounds of the invention may be achieved by other procedures known to those skilled in the art. Scheme 3 illustrates some of these synthetic procedures but the formation of the sulfonamide moieties of the compounds of the invention are not limited to these procedures. Scheme 3 also shows how the thiourea and urea groups that are defined by the R$^1$ and R$^2$ groups can be formed.

SCHEME 3

Modification of sulfonamide portion

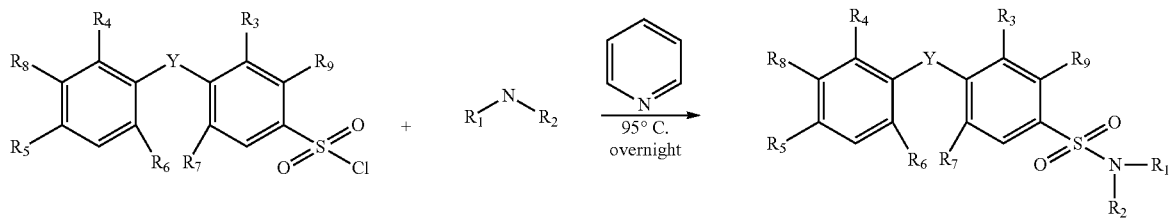

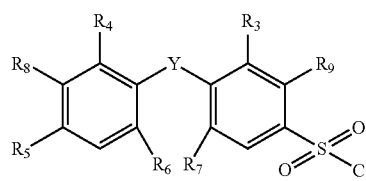 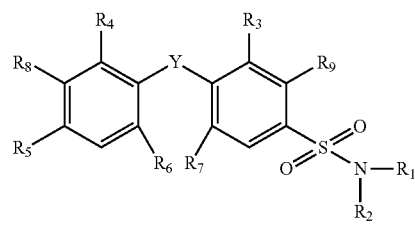

15     16     17 ureas and thioureas

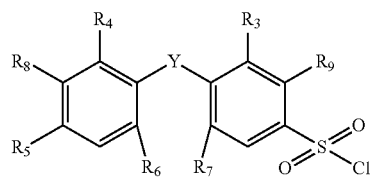 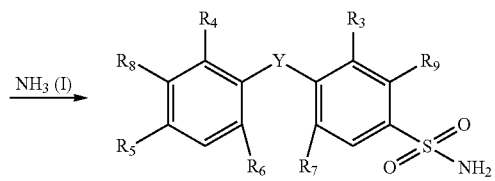

18     19

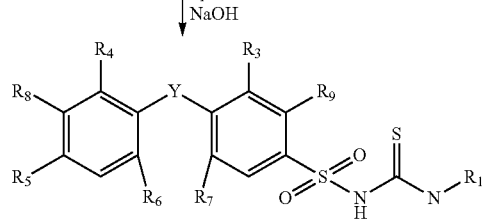

20

Synthesis of 1-Chloro-2-[4-Nitro-2-(Trifluoromethyl)phenoxy]benzene (Scheme-3)

1 g of 2-Fluoro-5-Nitro benzotrifluoride (4.78 m.moles) was dissolved in 3 ml of DMF. To this solution was added 640 mg (5 m.moles) of 2-chloro-phenol and 2.76 grams of potassium carbonate. The reaction mixture was heated for 4 hours at 100° C. The reaction was cooled to room temperature and 200 ml of water added. It was then extracted 4 times with methylene chloride. The combined organic layers were dried over anhydrous magnesium sulfate and the solvent evaporated to yield a pale yellow oil. It was purified using silica-gel column chromatography (1:3 ethyl acetate hexane) to yield 1.15 g (87.5% yield) of pure 1-Chloro-2-[4-Nitro-2-(Trifluoromethyl)phenoxy]benzene as product.

$^1$H NMR (CDCl$_3$) $\delta$ 6.67 (d, J=9.3 Hz, 1H), 7.20 (dd, J=1.5, 8 Hz, 1H), 7.54 (dd, J=1.5, 7.8 Hz, 1H), 7.35 (m, 2H) 8.28 (dd, J=2.7, 9.3 Hz, 1H), 8.6 (d, J=2.7 Hz, 1H).

MS Found 318 (MH$^+$)

Synthesis of 3-Chloro-4-[4-Nitro-2-(Trifluoromethyl)phenoxy]benzene sulfonyl chloride 1.15 g of 1-Chloro-2-[4-Nitro-2-(Trifluoromethyl)phenoxy]benzene was dissolved in 15 ml of dichloromethane and cooled to 0° C. To this cold mixture was added dropwise 0.5 ml of chlorosulfonic acid. The reaction was slowly warmed up to room temperature and stirred for 4 hours. The reaction mixture was concentrated and 200 ml of ether was added to it and the solution washed with water and then brine. The organic layer was dried over anhydrous sodium sulfate and the solvent evaporated to give 1.32 gm of a white solid which was the expected sulfonyl chloride by $^1$H NMR. (yield=88%)

$^1$HNMR (CDCl$_3$) $\delta$ 6.95 (d, J=9.3 Hz, 1H), 7.32 (d, J=8.7 Hz, 1H), 8.01 (dd, J=2.4, 8.4 Hz, 1H), 8.22 (d, J=2.4 Hz, 1H), 8.4 (dd, J=2.7, 9 Hz, 1H), 8.64 (d, J=2.7 Hz, 1H)

Synthesis of 3-chloro-N-[2-chloro-5-trifluoromethyl)phenyl]-4-[4-nitro-2-(trifluoromethyl)phenoxy]benzenesulfonamide (264)

To 50 mg of 3-Chloro-4-[4-Nitro-2-(Trifluoromethyl)phenoxy]benzene sulfonyl chloride (0.12 m.mole) was added 100 mg of 2-chloro-5-trifluoromethyl aniline and 3 ml of aniline. The mixture was heated at 98° C. overnight. The pyridine was then evaporated off under vacuum and the residue taken up in methylene chloride and washed with water and then brine. The organic layer was evaporated and the residue purified by radial silica-gel chromatography to yield 51.2 mg of the desired product in 97% purity by LC/MS. MS Found M−1 (573) (yield 74%)

$^1$H NMR (CDCl$_3$) $\delta$ 6.75 (d, J=9 Hz, 1H), 7.154 (br s, 1H), 7.20 (d, J=8.7 Hz, 1H), 7.4 (dd, J=0.6, 2.1 Hz, 1H), 7.465 (s, 1H), 7.74 (dd, J=2.4, 8.7 Hz, 1H), 7.93 (d, J=2.1 Hz, 1H), 7.99 (d, J=2.4 Hz, 1H), 8.34 (dd, J=2.7, 9 Hz, 1H), 8.61 (d, J=2.7 Hz, 1H).

Synthesis of Biaryl Ether Sulfonamides (Scheme-3)

Other biaryl ether sulfonamides were prepared by the reaction of the appropriate sulfonyl chloride and aniline (4-5 eq) in pyridine at 95° C. as described above for the synthesis of 3-chloro-N-[2-chloro-5-trifluoromethyl)phenyl]4-[4-nitro-2-(trifluoromethyl)phenoxy]benzenesulfonamide

3-chloro-N-[2-chloro-4-(trifluoromethyl)phenyl]-4-[4-nitro-2-(trifluoromethyl) phenoxy]benzenesulfonamide (265)

LC/MS purity 95.37% M−1 seen (573)
$^1$H NMR (CDCl$_3$) 6.75 (d, J=9.3 Hz), 7.2 (d, J=8.4 Hz, 1H), 7.318 (s, 1H), 7.55 (d, J=8.4 Hz, 1H), 7.62 (d, J=1.8 Hz, 1H), 7.78 (dd, J=2.1, 8.4 Hz, 1H), 7.775 (d, J=8.4 Hz, 1H), 8.02 (d, J=2.1 Hz, 1H), 8.35 (dd, J=2.4, 9 Hz, 1H), 8.62 (d, J=2.7 Hz, 1H).

3-chloro-N-[5-chloro-2-(trifluoromethyl)phenyl]-4-[4-nitro-2-(trifluoromethyl) phenoxy]benzenesulfonamide (267)

LC/MS purity 95.1% M−1 seen (573)
$^1$H NMR (CDCl$_3$): δ 6.75 (d, J=9 Hz, 1H), 6.325 (s, 1H), 7.2 (d, J=8.7 Hz, 1H), 7.553 (s, 1H), 7.57 (dd, J=2.4, 9 Hz, 1H), 7.75 (dd, J=2.1, 8.7 Hz, 1H), 7.83 (d, J=8.1 Hz, 1H), 7.93 (d, J=2.1 Hz, 1H), 8.34 (dd, J=2.7, 9 Hz, 1H), 8.6 (d, J=2.7 Hz, 1H).

N-[5-chloro-2-(trifluoromethyl)phenyl]-4-{[3-chloro-5-(trifluoromethyl)pyridin-2-yl]oxy}benzenesulfonamide (272)

LC/MS purity 97% M−1 seen (529)
$^1$H NMR (CDCl$_3$): δ 6.829 (br s, 1H), 7.25 (d, J=8.1 Hz, 2H), 7.5 (overlapping doublet and singlet, 2H), 7.8 (overlapping doublet and singlet, 3H), 8.005 (d, J=2.1 Hz, 1H), 8.25 (m, 1H).

3-chloro-N-(2,5-dichloropyridin-3-yl)-4-[4-nitro-2-(trifluoromethyl)phenoxy]benzenesulfonamide (2631

LC/MS purity 99.75%. M−1 and M+1 seen (542 and 544)
$^1$H NMR (CDCl$_3$) δ 6.8 (d, J=9 Hz, 1H), 7.24 (d, J=2.4 Hz, 1H), 7.75 (dd, J=2.1.9 Hz, 1H), 8.01 (d, J=2.4 Hz, 1H), 8.02 (d, J=2.4 Hz, 1H), 8.165 (d, J=2.4 Hz, 1H), 8.35 (dd, J=2.7, 9 Hz, 1H), 8.63 (d, J=2.7 Hz).

4-{[3-chloro-5-(trifluoromethy)pyridin-2-yl]oxy}-N-(2,6-difluorophenyl)benzene sulfonamide (259)

LC/MS purity 94.15% M−1 and M+1 seen (463 and 465)
$^1$H NMR (CDCl$_3$) δ 6.214 (s, 1H), 6.9 (d, J=6 Hz, 1H), 6.93 (d, J=6 Hz, 1H). 7.3 (overlapping peaks, 3H), 7.9 (d, J=8.7 Hz, 1H), 8.02 (d, J=2.1 Hz, 1H), 8.35 (m, 1H).

4-{[3-chloro-5-(trifluoromethyl)pyridin-2-yl]oxy}-N-(2,5-dichloropyridin-3-yl) benzenesulfonamide (257)

LC/MS purity 96.77% M+1 seen (498)
$^1$H NMR (CDCl$_3$) δ 7.042 (s, 1H), 7.32 (d, J=8.7 Hz, 2H), 7.9 (d, J=8.4 Hz, 1H), 8.03 (t, J=3 Hz, 2H), 8.1 (d, J=3 Hz, 1H), 8.27 (m, 1H).

3,5-dichloro-4-(2-chloro-4-nitrophenoxy)-N-pyridin-2-ylbenzenesulfonamide (216)

LC/MS purity 95.28% M−1 and M+1 seen (472 and 474)
$^1$H NMR (CDCl$_3$) δ 6.52 (d, J=9 Hz, 1H), 6.93 (t, J=7.2 Hz, 1H), 7.45 (d, J=9 Hz, 1H), 7.85 (ddd, J=1.5, 2.4, 7.2 Hz, 1H), 8.007 (d, J=3 Hz, 1H), 8.007 (s, 1H), 8.04 (d, J=1.5 Hz, 1H), 8.33 (d, J=3 Hz, 1H), 8.4 (d, J=2.4 Hz, 1H).

3,5-dichloro-4-(2-chloro-4-nitrophenoxy)-N-4-methoxyphenyl)benzenesulfonamide (208)

LC/MS purity 94.94% M−1 seen (501)
$^1$H NMR (CDCl$_3$) δ 3.8 (s, 3H), 6.46 (d, J=9 Hz, 2H), 6.84 (d, J=9 Hz, 2H), 6.5 (br, 1H), 7.02 (d, J=9 Hz), 7.778 (s, 2H), 8.03 (dd, J=2.4, 9 Hz, 1H), 8.405 (d, J=2.4 Hz, 1H)

3,5-dichloro-4-(2-chloro-4-nitrophenoxy)-N-(2,5-dichlorophenyl)benzene sulfonamide (203)

LC/MS purity 94.7% M−1 seen (539)
$^1$H NMR (CDCl$_3$) δ 6.47 (d, J=9 Hz, 1H), 6.997 (s, 1H), 7.185 (dd, J=2.4, 9.3 Hz, 1H), 7.283 (t, J=9 Hz, 1H), 7.7 (d, J=2.4 Hz, 1H), 7.843 (s, 2H), 8.04 (dd, J=2.4, 9 Hz, 1H), 8.42 (d, J=2.4 Hz, 1H).

3,5-dichloro-4-(2-chloro-4-nitrophenoxy)-N-pyridin-3-ylbenzene sulfonamide (204)

LC/MS purity 92.7% M−1 and M+1 seen (472 and 474)
$^1$H NMR (CDCl$_3$) δ 6.46 (d, J=9 Hz, 1H), 7.3 (m, 1H), 7.75 (m, 1H), 7.842 (s, 2H), 8.01 (dd, J=2.4, 9 Hz, 1H), 8.2 (br s, 1H), 8.32 (br m, 1H), 8.37 (d, J=2.4 Hz, 1H)

3,5-dichloro-4-(2-chloro-4-nitrophenoxy)-N-2-iodophenyl)benzenesulfonamide (209)

LC/MS purity 94.94% M−1 (501 seen)
$^1$H NMR (CDCl$_3$) δ 6.5 (d, J=9 Hz, 1H), 6.804 (s, 1H), 6.98 (td, J=1.5, 7.2 Hz, 1H), 7.42 (td, J=1.5, 7.2 Hz, 1H), 7.68 (dd, J=1.5, 8.1 Hz, 1H), 7.71 (dd, J=1.5, 8.1 Hz, 1H), 7.75 (s, 1H), 8.02 (dd, J=2.7, 9 Hz, 1H) 8.4 (d, J=2.7 Hz, 1H)

3,5-dichloro-4-(2-chloro-4-nitrophenoxy)-N-(2-methyl-1H-indol-5-yl)benzene sulfonamide 244)

LC/MS purity 93.9% M−1 seen (524)
$^1$H NMR (CDCl$_3$) δ 6.19 (s, 1H), 6.4 (d, J=9 Hz, 1H), 6.576 (s, 1H), 6.80 (dd, J=2.1, 8.4 Hz, 1H), 7.2 (dd, J=2.1, 8.4 Hz, 1H), 7.75 (s, 2H), 7.98 (s, 1H), 8.0 (dd, J=2.7, 9 Hz, 1H), 8.4 (d, J=2.4 Hz, 1H)

3,5-dichloro-4-(2-chloro-4-nitrophenoxy)-N-(5-fluoro-2-methylphenyl)benzene sulfonamide (242)

LC/MS purity 95.73% M−1 seen (503)
$^1$H NMR (CDCl$_3$) δ 6.475 (d, J=9.3 Hz, 1H), 6.651 (s, 1H), 6.887 (dt, J=2.4, 9.3 Hz, 1H) 7.112 (overlapping peaks, 2H), 7.86 (s, 2H), 8.0 (dd, J=2.7, 9 Hz, 1H), 8.4 (d, J=2.7 Hz, 1H)

3,5-dichloro-4-(2-chloro-4-nitrophenoxy)-N-(2-chloro-5-(trifluoromethyl)phenyl]benzenesulfonamide (243)

LC/MS purity 96.1% M−1 seen (575)
$^1$H NMR (CDCl$_3$) δ 7.122 (s, 1H, 7.49 (m, 2H), 7.842 (s, 2H), 7.94 (d, J=1.5 Hz, 1H), 8.04 (dd, J=2.7, 9 Hz, 1H), 8.41 (d, J=2.7 Hz, 1H).

3,5-dichloro-4-(2-chloro-4-nitrophenoxy)-N-(2-fluoro-5-nitrophenyl)benzene sulfonamide (220)

LC/MS purity 96.48% M−1 seen (534)
$^1$H NMR (CDCl$_3$) δ 6.5 (d, J=9.3 Hz, 1H), 7.275 (t, J=9 Hz, 1H), 7.932 (s, 2H), 8.05 (dd, J=2.7, 9 Hz, 1H), 8.1 (m, 1H), 8.42 (d, J=2.7 Hz, 1H), 8.5 (dd, J=2.4, 9 Hz, 1H)

3,5-dichloro-4-(2-chloro-4-nitrophenoxy)-N-(4-chloro-2-nitrophenyl)benzene sulfonamide (215)

LC/MS purity 97.45% M−1 seen (550)
$^1$H NMR (CDCl$_3$) δ 6.5 (d, J=9 Hz, 1H), 7.67 (dd, J=2.4, 9 Hz, 1H), 7.82 (d, J=9 Hz, 1H), 7.882 (s, 2H), 8.05 (dd, J=2.4, 9 Hz, 1H), 8.165 (d, J=2.4 Hz, 1H), 8.41 (d, J=2.4 Hz, 1H), 9.17 (s, 1H)

3,5-dichloro-N-[5-chloro-2-(trifluoromethyl)phenyl]-4-(2,4-dichlorophenoxy) benzenesulfonamide (249)

LC/MS purity 96.61% M−1 seen (573)
$^1$H NMR (CDCl$_3$) δ 6.42 (d, J=9.3 Hz, 1H), 7.582 (s, 1H), 7.6 (dd, J=2.7, 8.4 Hz, 1H), 7.791 (s, 2H), 7.8 (t, J=8.4 Hz, 1H), 8.02 (dd, J=2.7, 9.3 Hz, 1H), 8.41 (d, J=2.7 Hz, 1H)

3,5-dichloro-4-(2-chloro-4-nitrophenoxy)-N-[2-chloro-4-(trifluoromethyl)phenyl]benzenesulfonamide (240)

LC/MS purity 99.15% M−1 seen (592)
$^1$H NMR (CDCl$_3$) δ 6.475 (d, J=9 Hz, 1H), 7.6 (dd, J=2.4, 9.3 Hz, 1H), 7.65 (d, J=2.4 Hz, 1H), 7.8 (d, J=9 Hz, 1H), 7.878 (s, 2H), 8.03 (dd, J=2.7, 9.3 Hz, 1H), 8.4 (d, J=2.7 Hz)

N-[2-chloro-5-(trifluoromethyl)phenyl]-4-{[3-chloro-5-(trifluoromethyl)pyridin-2-yl]oxy}benzenesulfonamide (254)

LC/MS purity 95.85% M−1 seen (529)
$^1$H NMR (CDCl$_3$) δ 7.3 (overlapping m, 3H), 7.41 (d, J=8.4 Hz, 1H), 7.87 (d, J=8.7 Hz, 2H), 7.95 (d, J=1.5 Hz, 1H), 8.01 (d, J=2.1 Hz, 1H), 8.25 (m, 1H)

3,5-dichloro-4-2-chloro-4-nitrophenoxy)-N-[4,6-dibromopyridin-2-yl)benzene sulfonamide (218)

LC/MS purity 94.49% M−1 seen (630)
$^1$H NMR (CDCl$_3$) δ 6.53 (d, J=9 Hz, 1H), 7.7 (br, 1H), 7.98 (d, J=2.1 Hz, 1H), 8.05 (dd, J=2.7, 9 Hz, 1H) 8.259 (s, 2H), 8.27 (m, 1H), 8.42 (d, J=2.7 Hz, 1H)

Another procedure for synthesis of Biaryl ether sulfonamides:

Synthesis of 3,5-dichloro-4-(2-chloro-4-nitrophenoxy)-N-[4-isopropoxyphenyl]benzenesulfonamide (134)

To 100 mg of 3,5-Dichloro-4-(2-Chloro-4-Nitrophenoxy) Benzene-1-Sulfonyl Chloride (0.23 m.mol) was added 0.2 ml of DIEA, 5 ml of dichloromethane and 150 mg of 4-isopropoxyaniline. The mixture was maintained at 40° C. for 4 hours. The solvent was evaporated and the residue dissolved in ethyl acetate and washed with water and brine. The organic layer was dried over anhydrous Na$_2$SO$_4$ and the solvent evaporated. The residue as purified using radial silica-gel chromatography using 1:4 ethyl acetate:hexane as solvent. The purity of the product by LC/MS was 97.19%. M−1 (530) was seen in the mass spectrum. The yield of the product was 80.3 mg or 63% yield.

$^1$H NMR (CDCl$_3$) δ 1.31 (d, J=6 Hz, 6H), 4.5 (septuplet, J=6 Hz, 1H), 6.47 (d, J=9 Hz, 2H), 6.81 (d, J=9 Hz, 2H), 7.0 (d, J=9 Hz, 1H), 7.764 (s, 2H), 8.04 (dd, J=2.4, 9 Hz, 1H), 8.41 (d, J=2.4 Hz, 1H).

Synthesis of 3,5-dichloro-4-(2-chloro-4-nitro phenoxy)benzenesulfonamide (124)

2 m. moles of 3,5-Dichloro-4-(2-Chloro-4-Nitrophenoxy) Benzene-1-Sulfonyl Chloride (932 mg) in 5 ml of dichloromethane was cooled to −78° C. and 2 ml of ammonium hydroxide solution added to it. The reaction was stirred for 4 hours. The solvent was evaporated to give 755 mg (94% yield) of pure 3,5-dichloro-4-(2-chloro-4-nitro phenoxy) benzenesulfonamide.

$^1$H NMR (CDCl$_3$) δ 6.94 (d, J=9 Hz, 1H), 7.74 (s, 2H), 8.06 (s, 2H), 8.1 (dd, J=2.7, Hz, 1H), 8.52 (d, J=2.7 Hz).

Procedure for the Synthesis of Ureas and Thioureas (Scheme-3)

Synthesis of 3,5-dichloro-4-(2-chloro-4-nitrophenoxy)-N-{[(3,4-dichlorophenyl)amino]carbothioyl}benzenesulfonamide (148)

40 mg of 3,5-dichloro-4-(2-chloro-4-nitro phenoxy) benzenesulfonamide (0.1 m.mol) was dissolved in 2.5 ml of acetone. 0.5 ml of 1N NaOH was added to this and the mixture shaken for 30 mins at room temperature. 0.1 m.mole of 3,4-Dichlorophenyl isothiocyanate was added and the reaction stirred at 45° C. for 4 hours. The reaction mixture was neutralized by addition of 1N acetic acid. This was followed by addition of 3 ml of water. The white precipitate formed was extracted with ethyl acetate. The ethyl acetate was evaporated and the residue obtained was purified by radial silica-gel chromatography using 1:4 ethyl acetate:hexane as eluant to give 50.5 mg of desired product as a white solid (84% yield).

$^1$H NMR (CDCl$_3$) δ 6.5 (d, J=9 Hz, 1H), 7.01 (dd, J=2.4, 8.4 Hz, 1H), 7.2 (s, 1H), 7.4 (d, J=8.4 Hz, 1H), 7.85 (s, 2H), 8.06 (dd, J=2.4, 9 Hz, 1H), 8.42 (d, J=2.4 Hz, 1H)

Another synthetic procedure for producing the compounds of the invention involves starting with the sulfonamide phenol 21 and reacting with the boronic acid 22 to produce the ether sulfonamide 23.

SCHEME 4

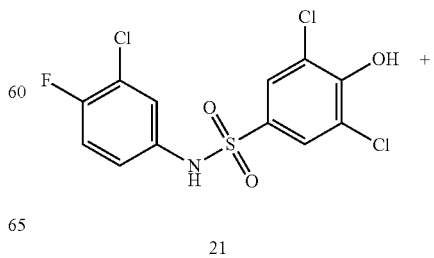

21

-continued

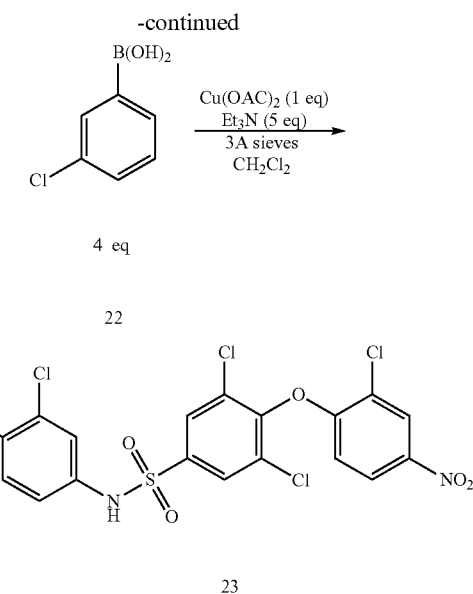

Examples 123 and 151

Compounds of Example 123, 151 and their analogs can be synthesized according to Scheme 5.

Scheme 5

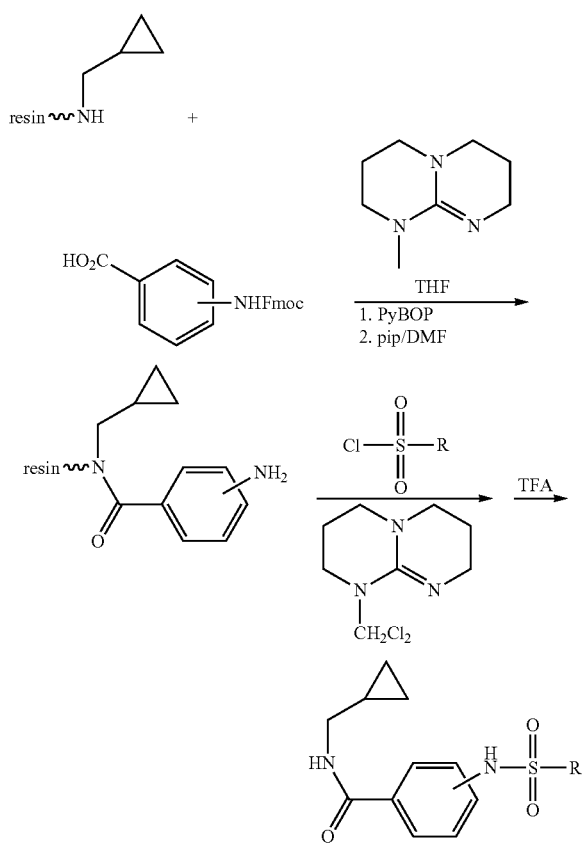

-continued

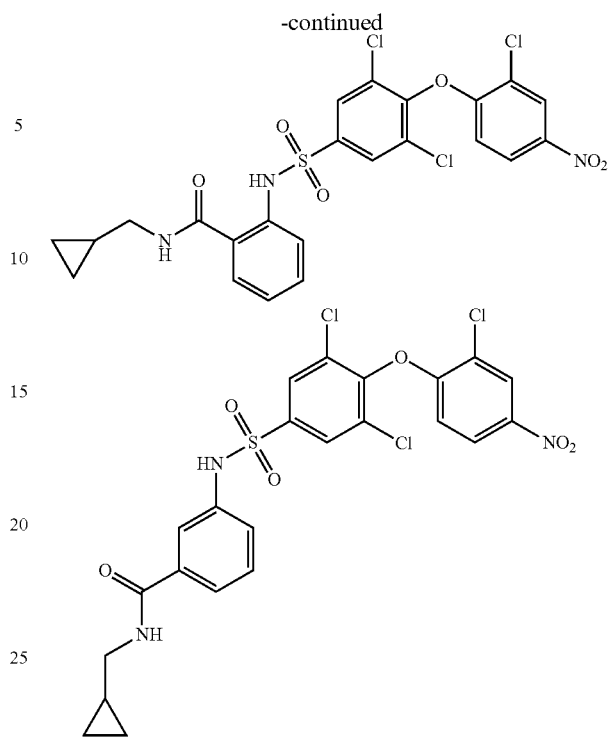

Procedure for the Resin-Based Synthesis of N-(cyclopropylmethyl)-3-({[3,5-dichloro-4-(2-chloro-4-nitrophenoxy)phenyl]sulfonyl}amino)benzamide (151) (Scheme 5)

Step 1. To cyclopropylaminomethyl resin (0.49 mmol) were added N-(9-fluorenylmethoxycarbonyl)-3-aminobenzoic acid (356 mg, 0.99 mmol), benzotriazole-1-yloxy-trispyrrolidinophosphonium hexafluorophosphate (PyBOP) (515 mg, 0.99 mmol), N,N-diisopropylethylamine (400 μL, 1.96 mmol), and THF (10 mL). The slurry was shaken at room temperature overnight. The resin was filtered, washed sequentially with dichloromethane, methanol, ethyl acetate, diethyl ether, and dried under vacuum. The resin was treated with piperidine in DMF (10% solution, 10 mL) for one hour at room temperature. The resin was filtered and rinsed with NMP, methanol, dichloromethane, diethyl ether and dried under vacuum and used for the next step.

Step 2. The resin-bound amine from step 1 (200 mg, 0.2 mmol) was combined with 4-(2-chloro-4-nitrophenoxy)-3,5- dichloro-benzenesulfonyl chloride (0.25 g, 0.6 mmol), and 1,3,4,6,7,8-hexahydro-1-methyl-2H-pyrimido[1,2-A]pyrimidine (0.1 mL, 0.6 mmol) were combined in dichloromethane (2 mL) and stirred at room temperature overnight. The resin was filtered and rinsed successively with dichloromethane, methanol, ethyl acetate, and diethyl ether, and dried under vacuum. The resin was treated with trifluoracetic acid, H$_2$O, and dichloromethane for one hour at room temperature. The resin was filtered and rinsed with dichloromethane. The filtrate was concentrated by rotary evaporator to afford the compound, which was purified by radial silica gel chromatography (1:3 ethyl acetate:hexanes) to afford compound, which was 96% pure by LCMS analysis (0.9 mg, 0.8%).

N-(cyclopropylmethyl)-3-({[3,5-dichloro-4-(2-chloro-4-nitrophenoxy)phenyl]sulfonyl}amino)benzamide (151)

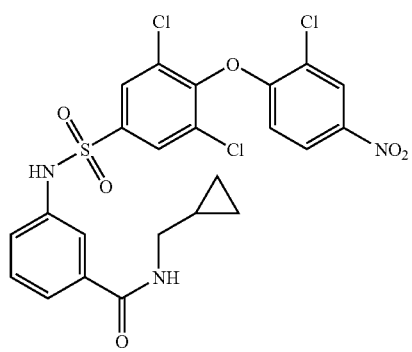

$^1$H NMR (CDCl$_3$, 300 MHz) δ 8.29 (d, J=2.7 Hz, 1H), 8.00 (dd, J=2.7, 9 Hz, 1H), 7.73-7.71 (m, 1H), 7.48-7.43 (m, 1H), 7.33 (t, J=2.1 Hz, 1H), 7.21 (ddd, J=0.9, 2.1, 7.8 Hz, 1H), 6.58 (d, J=9 Hz, 2H), 6.03 (br t, J=5.1 Hz, 1H), 3.16 (dd, J=5.4, 6.9 Hz, 2H), 0.91-0.84 (m, 1H), 0.51-0.38 (m, 2H), 0.15-0.10 (m, 2H).

LCMS purity 96%. MS (negative ion) Found 568 (M-H$^+$).

N-(cyclopropylmethyl)-1-{[3,5-dichloro-4-(2-chloro-4-nitrophenoxy)phenyl]sulfonyl}prolinamide (139)

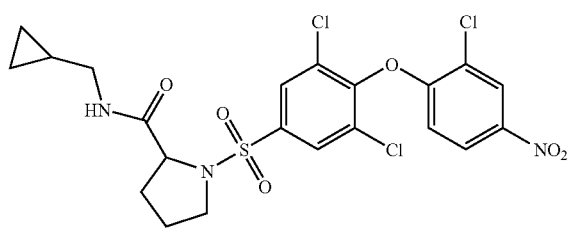

This compound was prepared according to the procedure for the preparation of 151.

$^1$H NMR (CDCl$_3$, 300 MHz) δ 8.43 (d, J=1.8 Hz, 1H), 8.06 (ddd, J=0.6, 2.4, 9 Hz, 1H), 7.93 (s, 2H), 6.85 (m, 1H), 6.53 (dd, J=0.6, 9 Hz, 1H), 4.164.13 (m, 1H), 3.68-3.62 (m, 1H), 3.32-3.24 (m, 1H), 3.21-3.15 (m, 2H), 2.31-2.27 (m, 1H), 1.97-1.80 (m, 3H), 1.04-0.98 (m, 1H), 0.60-0.54 (m, 2H), 0.29-0.24 (m, 2H).

LCMS purity 98%. MS Found 548 (MH$^+$).

Examples 120, 121, 122, 125-128, 129, 130-133 and 134

Compounds of Example 120, 121, 122, 125-128, 129, 130-133 and 134 and their analogs can be synthesized according to Scheme 6.

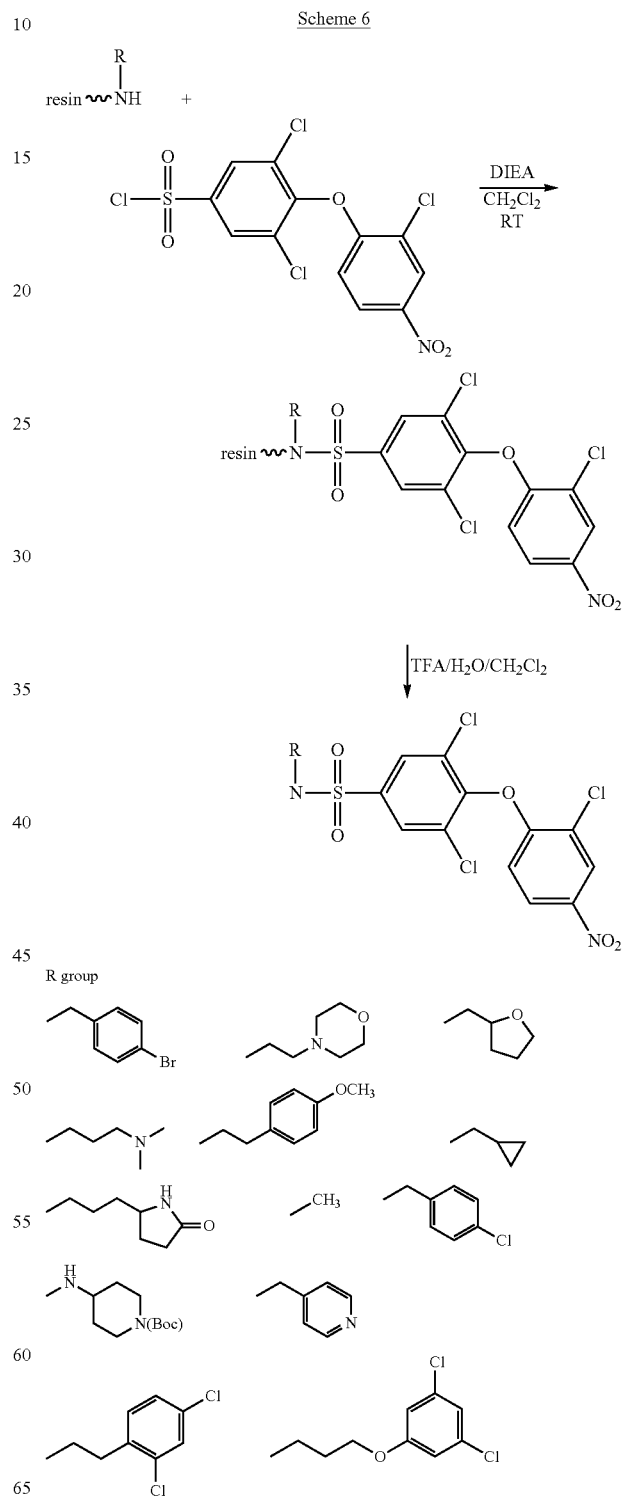

Procedure For The Resin-Based Synthesis Of N-(Cyclopropylmethyl)-3,5-Dichloro-4-(2-Chloro-4-Nitrophenoxy)Benzenesulfonamide (120) (Scheme 6)

To cyclopropylaminomethyl resin (0.20 mmol) were added 4-(2-chloro-4-nitrophenoxy)-3,5-dichloro-benzenesulfonyl chloride (165 mg, 0.40 mmol), N, N-diisopropylethylamine (200 µL, 1.00 mmol), and dichloromethane (2 mL). The slurry was shaken at room temperature overnight. The resin was filtered, washed sequentially with dichloromethane, methanol, ethyl acetate, diethyl ether and dried under vacuum. The desired compound was released from the resin by treatment with trifluoroacetic acid, water, and dichloromethane for one hour at room temperature. The resin was filtered and rinsed with dichloromethane and the filtrate concentrated by rotary evaporator to afford the compound as a white solid, which was 95% by LCMS analysis (7 mg, 7.7%).

N-(Cyclopropylmethyl)-3,5-Dichloro-4-(2-Chloro-4-Nitrophenoxy) Benzenesulfonamide (120)

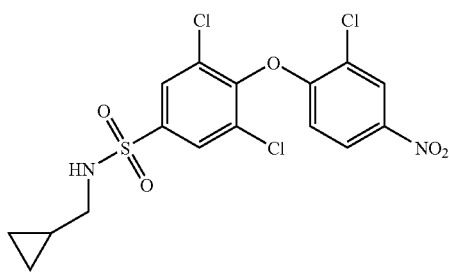

$^1$H NMR (CDCl$_3$, 300 MHz) δ 8.43 (d, J=3 Hz, 1H), 8.06 (dd, J=3, 9 Hz, 1H), 7.96 (s, 2H), 6.54 (d, J=9 Hz, 1H), 4.69 (t, J=6 Hz, 1H), 2.96 (dd, J=6, 7 Hz, 2H), 0.98-0.92 (m, 1H), 0.59-0.53 (m, 2H), 0.22-0.17 (m, 2H).

LCMS purity 95%. MS Found 451 (MH$^+$), 492 (MH$^+$+ CH$_3$CN).

N-(4-bromobenzyl)-3,5-dichloro-4-(2-chloro-4-nitrophenoxy)benzenesulfonamide (128)

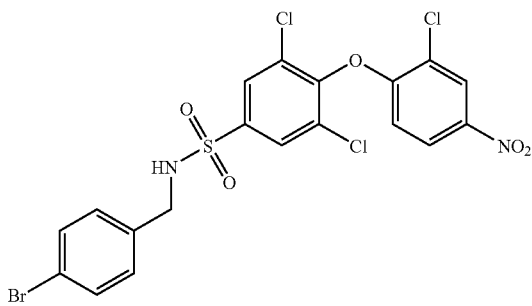

This compound was prepared according to the procedure for the preparation of 120 using 4-bromobenzylamine resin in place of the cyclopropylamino methyl resin.

$^1$H NMR (DMSO-d$_6$, 300 MHz) δ 8.59 (t, J=6.3 Hz, 1H), 8.52 (d, J=2.7 Hz, 1H), 7.87 (s, 2H), 7.48 (d, J=8.4 Hz, 2H), 7.19 (d, J=8.4 Hz, 2H), 6.87 (d, J=9 Hz, 1H), 4.13 (d, J=6 Hz, 2H).

LCMS purity 100%. MS (negative ion) Found 563 (M-H$^+$)

Biological Activity

The following examples illustrate the biological activity assays of the compounds of the invention. Various types of assays were used to show the inhibitory activity of the compounds of the invention towards ubiquitin ligases. The examples described below are not meant to limit in any way the use of the compounds of the invention as ubiquitin ligase inhibitors.

Example A

Plate-Based E3 Ligase Assay (APC FLAG)

E3 (His-APC11/APC2-"APC") auto-ubiquitination was measured as described in U.S. patent application Ser. No. 09/826,312 (Publication No. US-2002-0042083-A1), which is incorporated herein in its entirety. Details of the protocol are described below. Activity in the presence of the compound was determined relative to a parallel control in which only DMSO was added. Values of the IC$_{50}$ were typically determined using 6 or 8 different concentrations of the compound, although as few as 2 concentrations may be used to approximate the IC$_{50}$ value. Active compounds were those that exhibited an IC$_{50}$ values of 25 µM or lower.

Nickel-coated 96-well plates (Pierce 15242) were blocked for 1 hour with 100 µl of blocking buffer at room temperature. The plates were washed 4 times with 225 µl of 1×PBS and 80 µl of the reaction buffer were added that contained 100 ng/well of Flag-ubiquitin. To this, 10 µl of the test compound diluted in DMSO were added. After the test compound was added, 10 µl of E1 (human), E2 (Ubch5c), and APC in Protein Buffer was added to obtain a final concentration of 5 ng/well of E1, 20 ng/well of E2 and 100 ng/well of APC. The plate were shaken for 10 minutes and incubated at room temperature for 1 hour. After incubation, the plates were washed 4 times with 225 µl of 1×PBS and 100 µl/well of Antibody Mix were added to each well. The plates were incubate at room temperature for another hour after which they were washed 4 times with 225 µl of 1×PBS and 100 µl/well of Lumino substrate were added to each well. The luminescence was measured by using a BMG luminescence microplate reader.

To prepare the Blocking Buffer (1 liter; 1% Casein in 1×PBS), 10 grams of Casein (Hammersten Grade Casein from Gallard-Schlesinger Inc. #440203) were placed into 1 liter of 1×PBS, stirred on a hot plate and kept between 50-60° C. for an hour. The buffer was allowed to cool to room temperature and then filtered using a Buchner Funnel (Buchner filter funnel 83 mm 30310-109) and Whatman filter paper (Whatman Grade No. 1 Filter paper 28450-070). It was stored at 4° C. until used.

The reaction buffer consisted of 62.5 mM Tris pH 7.6 (Trizma Base—Sigma T-8524), 3 mM MgCl$_2$ (Magnesium Chloride—Sigma M-2393), 1 mM DTT (Sigma D-9779), 2.5 mM ATP (Roche Boehringer Mann Corp. 635-316), 100 ng/well of Flag-ubiquitin, 0.1% BSA (Sigma A-7906), and 0.05% Tween-20 (Sigma P-7949).

The Protein Buffer consisted of 20 mM Tris pH 7.6, 10% glycerol (Sigma G-5516) and 1 mM DTT.

The antibody mix consisted of 0.25% BSA (Sigma A-7906) in 1×PBS, 1/50,000 anti-Flag (Sigma F-3165), 1/100,000 of anti-Mouse IgG-HRP (Jackson Immunoresearch #115-035-146).

The substrate mix consisted of SuperSignal Substrate from Pierce (catalog number 37070ZZ) and was prepared by mixing 100 ml of the peroxide solution, 100 ml of the enhancer solution and 100 ml of Milli-Q® water.

In similar manner, autoubiquitination of the E3 MDM2 was determined (MDM2-FLAG). Further instruction in such assays can be found in U.S. patent application Ser. No. 10/108,767 (Publication No. US-2003-0104474 A1), which is incorporated herein in its entirety.

Example A2

Plate-Based MDM2 Substrate Ligation Assay (MDM2-P53-FLAG)

This assay was preformed essentially as described in WO 03/076899 (page 77, line 5 to page 80, line 13), hereby incorporated by reference in its entirety.

Example B

Cell Proliferation Assays

Cell Culture Preparation

A549 (ATCC# CCL-185), HeLa (ATCC# CCL-2), HCT116 (ATCC# CCL-247), and H1299 (ATCC# CRL-5803) cells were maintained in T175 flasks following the ATCC recommended media and handling procedures. Flasks reaching approximately 70% confluency were trypsinized and resuspended in RPMI media (Cell-Gro catalog number 10-040-CM) modified to contain 5% FBS, 100 ug/mlPen/Strep (Cell-Gro catalog number 30-002-CL), and 0.3 mg/ml L-Glutamine (Cell-Gro catalog number 25-003-CL). A 20,000 cells/ml solution was made for plating. Cells were plated in black Packard 96 well plates by placing 100 µl per well (2,000 cells per well).

Cell Treatment with Compounds

Compounds and additional media were added 24 hours after cell plating. A compound master plate was created with concentrations 500 times greater than the final concentration added to the cells. All compound testing was done in duplicate using 6.3 fold dilutions starting with 10 mM. All outside wells (and 4 internal wells) were DMSO controls. Taxol and at least one additional control were run on all plates. Three microliters of the compound master plate were added to deep well blocks containing 750 µl of RPMI media. One hundred microliters were transferred from the compound/media deep well blocks to the plated cells resulting in a 500 fold dilution of the compounds. Cells were grown at 37° C., 5% $CO_2$ for 48 hours.

Photographic Image Analysis of Proliferation, Apoptosis and Death (PAD Assay)

Cells to be analyzed by photography were fixed and stained. One hundred microliters of media were removed and 100 µl of 9.3% formamide was added to each well. Plates were left on the benchtop for 45 minutes. A staining solution containing 1.55 µl of 1 mg/ml DAPI added to 18.75 ml PBS was warmed for 15 minutes at 37° C. The cells were aspirated prior to washing with 100 µl of PBS. Seventy microliters of PBS were aspirated and 170 µl of the DAPI solution were added to each well of fixed cells. Plates were left at room temperature for one hour then aspirated and washed twice with 100 µl of PBS. The stained cells were left at 4° C. for a minimum of 16 hours before photographic analysis with Array Scan II (Cellomics). Analysis of the photographic images to determine numbers of live cells (proliferation), apoptotic cells and dead cells, were according to the methods described in U.S. Provisional Patent Application Ser. No. 60/406,714, which incorporated herein in its entirety.

Non-Photographic Proliferation Analysis

Some cell plates were treated with Promega Cell titer Aqueous 1 kit (promega—VWR catalog number G3580). In this case, 48 hours after the test compound were added, 100 µl of media were removed and 20 µl of cell titer reagent were added to all wells. Plates were incubated at 37° C. for 45 minutes prior to absorbance reads on the Wallac plate reader at 490 nm for 0.1 sec/well.

Example C

Gel-Based E2 Ligase Assay (Cell Titer-Aqueous)

E2 (Ubch5c) auto-ubiquitination was measured as described in U.S. patent application Ser. No. 09/826,312 (Publication No. US-2002-0042083-A1), which is incorporated herein in its entirety. Details of the protocol are described below. Activity in the presence of the test compound was determined relative to a parallel control in which only DMSO was added. The $IC_{50}$ values were typically determined using 6 or 8 different concentrations of compound, although as few as 2 concentrations may be used to approximate $IC_{50}$ values. Active compounds were those having $IC_{50}$ values of 25 µM or lower.

Corning 96-well plates (Corning 3650) were blocked with 100 µl of Blocking Buffer for 1 hour at room temperature. The plates were washed for 4 times with 225 µl of 1×PBS and 80 µl of the reaction buffer were added that contained 100 ng/well of Flag-ubiquitin. To this, 10 µl of the test compound diluted in DMSO were added. After the test compound was added, 10 µl of E1 (human) and E2 (Ubch5c) in Protein Buffer were added to obtain a final concentration of 5 ng/well of E1 and 20 ng/well of E2. The plates were shaken for 10 minutes and incubated at room temperature for 1 hour. After incubation, the reaction was stopped by adding 25 µl of loading buffer (non-reducing) per well and the plates were heated at 95° C. for 5 minutes. An aliquot of each well was run on a 10% NugePage Gel and analyzed by Western Blot using the antibody mix and Lumino substrate described below. The luminescence was measured using a BMG luminescence microplate reader.

To prepare the Blocking Buffer (1 liter; 1% Casein in 1×PBS), 10 grams of Casein (Hammersten Grade Casein from Gallard-Schlesinger Inc. #440203) were placed into 1 liter of 1×PBS, stirred on a hot plate and kept between 50-60° C. for an hour. The buffer was allowed to cool to room temperature and then filtered using a Buchner Funnel (Buchner filter funnel 83 mm 30310-109) and Whatman filter paper (Whatman Grade No. 1 Filter paper 28450-070). It was stored at 4° C. until used.

The reaction buffer consisted of 62.5 mM Tris pH 7.6 (Trizma Base—Sigma T-8524), 3 mM $MgCl_2$ (Magnesium Chloride—Sigma M-2393), 1 mM DTT (Sigma D-9779), 2.5 mM ATP (Roche Boehringer Mann Corp. 635-316), 100 ng/well of Flag-ubiquitin, 0.1% BSA (Sigma A-7906), and 0.05% Tween-20 (Sigma P-7949).

The Protein Buffer consisted of 20 mM Tris pH 7.6, 10% glycerol (Sigma G-5516) and 1 mM DTT.

The antibody mix consisted of 0.25% BSA (Sigma A-7906) in 1×PBS, 1/50,000 anti-Flag (Sigma F-3165), 1/100,000 of anti-Mouse IgG-HRP (Jackson Immunoresearch #115-035-146).

The substrate mix consisted of SuperSignal® Substrate from Pierce (catalog number 37070ZZ) and was prepared by mixing 100 ml of the peroxide solution, 100 ml of the enhancer solution and 100 ml of Milli-Q® water.

Example D

Gel-Based E3 Ligase Assay

E3 (His-APC11/APC2-"APC") auto-ubiquitination was measured as described in U.S. patent application Ser. No. 09/826,312 (Publication No. U.S. Pat. No. 2,002,0042083-A1), which is incorporated herein in its entirety. Details of the protocol are described below. Activity in the presence of compound was determined relative to a parallel control in which only DMSO is added. The $IC_{50}$ values were typically determined using 6 or 8 different concentrations of compound, although as few as 2 concentrations may be used to approximate the $IC_{50}$ values. Active compounds were those having $IC_{50}$ values of 25 μM or lower.

Corning 96-well plates (Corning 3650) were blocked with 100 μl of Blocking Buffer for 1 hour at room temperature. The plates were washed 4 times with 225 μl of 1×PBS and 80 μl of the reaction buffer were added that contained 100 ng/well of Flag-ubiquitin. To this, 10 μl of the test compound diluted in DMSO were added. After the test compound was added, 10 μl of E1 (human), E2 (Ubch5c) and APC in Protein Buffer were added to obtain a final concentration of 5 ng/well of E1, 20 ng/well of E2 and 100 ng/well APC. The plates were shaken for 10 minutes and incubated at room temperature for 1 hour. After incubation, the reaction was stopped by adding 25 μl of loading buffer (non-reducing) per well and the plates were heated at 95° C. for 5 minutes. An aliquot of each well was run on a 10% NugePage Gel and analyzed by Western Blot using the antibody mix and Lumino substrate described below. The luminescence was measured by using a BMG luminescence microplate reader.

To prepare the Blocking Buffer (1 liter; 1% Casein in 1×PBS), 10 grams of Casein (Hammersten Grade Casein from Gallard-Schlesinger Inc. #440203) were placed into 1 liter of 1×PBS, stirred on a hot plate and kept between 50-60° C. for an hour. The buffer was allowed to cool to room temperature and then filtered using a Buchner Funnel (Buchner filter funnel 83 mm 30310-109) and Whatman filter paper (Whatman Grade No. 1 Filter paper 28450-070). It was stored at 4° C. until used.

The reaction buffer consisted of 62.5 mM Tris pH 7.6 (Trizma Base—Sigma T-8524), 3 mM $MgCl_2$ (Magnesium Chloride—Sigma M-2393), 1 mM DTT (Sigma D-9779), 2.5 mM ATP (Roche Boehringer Mann Corp. 635-316), 100 ng/well of Flag-ubiquitin, 0.1% BSA (Sigma A-7906), and 0.05% Tween-20 (Sigma P-7949).

The Protein Buffer consisted of 20 mM Tris pH 7.6, 10% glycerol (Sigma G-5516) and 1 mM DTT.

The antibody mix consisted of 0.25% BSA (Sigma A-7906) in 1×PBS, 1/50,000 anti-Flag (Sigma F-3165), 1/100,000 of anti-Mouse IgG-HRP (Jackson Immunoresearch #115-035-146).

The substrate mix consisted of SuperSignal Substrate from Pierce (catalog number 37070ZZ) and was prepared by mixing 100 ml of the peroxide solution, 100 ml of the enhancer solution and 100 ml of Millie water.

The compounds in the table immediately below illustrate the inhibitory activity of the compounds of the invention. ("x pt" in the table below means that "x" concentrations were tested.)

| Ex. | APC Flag 8 pt | Cell Titer-Aqueous, A549 6 pt | Cell Titer-Aqueous, HCT116 6 pt | Cell Titer-Aqueous, HELA 6 pt | MDM2-Auto Flag 8 pt | MDM2-P53 Flag 8 pt | PAD Assay, A549 6 pt | PAD Assay, H1299 6 pt | PAD Assay, HCT116 6 pt | PAD Assay, HELA 6 pt |
|---|---|---|---|---|---|---|---|---|---|---|
| 7 | | | | | | − | | | | |
| 15 | − | | | | | | | | | |
| 16 | + | + | + | + | | | − | | | |
| 17 | + | | | | | | − | | | |
| 18 | − | | | | | | − | | | |
| 19 | − | | | | | | | | | |
| 20 | + | | | | | | | | | |
| 21 | − | | | | | | − | | | |
| 22 | − | | | | | | | | | |
| 23 | + | + | + | + | | − | + | | | + |
| 24 | + | | | | + | | − | | | |
| 25 | + | | | | | | − | | | |
| 26 | − | | | | | | + | | | |
| 27 | − | | | | | | − | | | |
| 29 | + | | | | | | + | | | |
| 31 | − | | | | | | + | | | |
| 34 | − | | | | | | | | | |
| 58 | + | + | + | + | + | + | + | | | + |
| 60 | − | | | | | | + | | | |
| 62 | − | + | + | + | | | + | | | + |
| 63 | − | | | | | | | | | |
| 119 | + | | | | | | | | | |
| 120 | + | | | | | | | | | |
| 121 | − | | | | | | | | | |
| 122 | + | | | | | | | | | |
| 123 | + | + | + | + | | − | + | | | + |
| 124 | + | | | | | | | | | |
| 125 | − | | | | | | | | | |
| 126 | − | | | | | | | | | |
| 127 | + | | | | | | | | | |
| 128 | − | | | | | | | | | |
| 129 | + | | | | | | | | | |
| 130 | − | | | | | | | | | |
| 131 | + | | | | | | | | | |

-continued

| Ex. | APC Flag 8 pt | Cell Titer-Aqueous, A549 6 pt | Cell Titer-Aqueous, HCT116 6 pt | Cell Titer-Aqueous, HELA 6 pt | MDM2-Auto Flag 8 pt | MDM2-P53 Flag 8 pt | PAD Assay, A549 6 pt | PAD Assay, H1299 6 pt | PAD Assay, HCT116 6 pt | PAD Assay, HELA 6 pt |
|---|---|---|---|---|---|---|---|---|---|---|
| 132 | − | | | | | | | | | |
| 133 | − | | | | | | | | | |
| 134 | + | | | | | | | | | |
| 135 | + | | | | | | | | | |
| 136 | + | | | | | | | | | |
| 137 | + | | | | | | | | | |
| 138 | + | | | | | | | | | |
| 139 | − | | | | | | | | | |
| 140 | + | − | − | − | | | | | | |
| 141 | − | | | | | | | | | |
| 142 | + | | | | | | | | | |
| 143 | + | | | | | | | | | |
| 144 | + | | | | | | | | | |
| 145 | + | − | − | − | | | | | | |
| 146 | + | + | + | + | | | + | | | + |
| 147 | + | + | + | + | | | + | | | + |
| 148 | + | − | | − | | | | | | |
| 149 | + | + | + | + | | | + | | | + |
| 150 | + | + | + | + | | | | | | |
| 151 | + | | | | | | | | | |
| 152 | + | | | | | | | | | |
| 153 | − | | | | | | | | | |
| 154 | + | + | − | + | | | − | | − | − |
| 155 | + | − | | − | | | + | | | |
| 156 | + | + | | + | | | | | | + |
| 157 | + | | | | | | | | | |
| 158 | − | | | | | | | | | |
| 159 | + | + | + | + | | | + | | | + |
| 160 | + | + | | + | | | + | | | + |
| 161 | + | | | | | | | | | |
| 162 | + | | | | | | | | | |
| 163 | + | | | | | | | | | |
| 164 | + | | | | | | | | | |
| 165 | + | + | | + | | | + | | | + |
| 166 | + | + | | + | | | | | | |
| 167 | + | + | | + | | | + | + | | + |
| 168 | + | + | | + | | | + | | | + |
| 169 | + | | | | | | | | | |
| 170 | + | + | | + | | | | | | |
| 171 | − | | | | | | + | | | − |
| 172 | + (gel) | + | | + | | | + | | | + |
| 173 | − (2 pt) | − | | − | | | − | | | − |
| 174 | + | + | | + | | | + | | | + |
| 175 | + | − | | − | | | | | | |
| 176 | − | | | | | | | | | |
| 177 | + | | | | | | | | | |
| 178 | + | | | | | | | | | |
| 179 | + | − | | + | | | | | | |
| 180 | − | | | | | | | | | |
| 181 | − | | | | | | | | | |
| 182 | − | | | | | | | | | |
| 183 | − | | | | | | | | | |
| 184 | − | | | | | | | | | |
| 185 | − | | | | | | | | | |
| 186 | − (2 pt) | | | | | | | | | |
| 187 | − (2 pt) | | | | | | | | | |
| 188 | − (2 pt) | | | | | | | | | |
| 189 | − (2 pt) | | | | | | | | | |
| 190 | − (2 pt) | | | | | | | | | |
| 191 | − (gel) | | | | | | + | | + | + |
| 192 | + | | | | | | − | | | − |
| 193 | − (gel) | | | | | | | | | |
| 194 | − (2 pt) | | | | | | | | | |
| 195 | − (2 pt) | | | | | | | | | |
| 196 | − (2 pt) | | | | | | | | | |
| 197 | + | | | | | | | | | |
| 198 | + | | | | | | | | | |
| 199 | + | | | | | | + | | | + |
| 200 | + | + | | + | | | + | | | + |
| 201 | + | + | | + | | | + | | | + |
| 202 | − | + | | + | | | + | | | + |
| 203 | + | + | | + | + | + | + | | + | + |
| 204 | + | + | | + | | | | | | |
| 205 | − | − | | − | | | | | | |
| 206 | − | + | | + | | | | | | |

| Ex. | APC Flag 8 pt | Cell Titer-Aqueous, A549 6 pt | Cell Titer-Aqueous, HCT116 6 pt | Cell Titer-Aqueous, HELA 6 pt | MDM2-Auto Flag 8 pt | MDM2-P53 Flag 8 pt | PAD Assay, A549 6 pt | PAD Assay, H1299 6 pt | PAD Assay, HCT116 6 pt | PAD Assay, HELA 6 pt |
|---|---|---|---|---|---|---|---|---|---|---|
| 207 | + | + |   | + |   |   |   |   |   |   |
| 208 | − | + |   | + |   |   | + |   |   | + |
| 209 | + | + |   | + |   |   | + |   |   | + |
| 210 | + | + |   | + |   |   | + |   |   | + |
| 211 | + |   |   |   |   |   |   |   |   |   |
| 212 | − |   |   |   |   |   |   |   |   |   |
| 213 | + | + |   | + |   |   |   |   |   |   |
| 214 | + | − |   | + |   |   | + |   |   | + |
| 215 | + | + |   | + | + | + | + |   | + | + |
| 216 | − (2 pt) |   |   |   |   |   | + |   |   | + |
| 217 | − (2 pt) |   |   |   |   |   | − |   |   | − |
| 218 | + | + |   | + | + | + | − |   | − | + |
| 219 | + | + |   | + |   |   | + |   | + | + |
| 220 | + | + |   | + | + | − | + |   | + | + |
| 221 | − (gel) | − |   | − |   |   | − |   |   | − |
| 222 | + | − |   | − |   |   |   |   |   |   |
| 223 | − (gel) | − |   | − |   |   |   |   |   |   |
| 224 | − (2 pt) | + |   | + |   |   |   |   |   |   |
| 225 | + |   |   |   |   |   |   |   |   |   |
| 226 | + |   |   |   |   |   | + |   | + | + |
| 227 | − (2 pt) |   |   |   |   |   |   |   |   |   |
| 229 | + |   |   |   |   |   | + |   |   | + |
| 230 | + |   |   |   |   |   | + |   | + | + |
| 231 | + |   |   |   |   |   | + |   |   | + |
| 232 | + |   |   |   |   |   | + |   |   | + |
| 233 | + |   |   |   |   |   |   |   |   |   |
| 234 | + |   |   |   |   |   | + |   |   | + |
| 235 | + |   |   |   |   |   | + | + |   | + |
| 236 | + |   |   |   |   |   | + |   |   | + |
| 237 | + |   |   |   |   |   | + |   |   | + |
| 238 | + |   |   |   |   |   | + |   |   | + |
| 239 | + |   |   |   |   |   |   |   |   |   |
| 240 | + |   |   |   |   |   | + |   |   | + |
| 241 | + |   |   |   |   |   | + |   |   | + |
| 242 | + |   |   |   |   |   | + |   |   | + |
| 243 | + |   |   |   |   |   | + | + | + | + |
| 244 | + |   |   |   |   |   | + |   |   | + |
| 245 | + |   |   |   |   |   | + |   |   | + |
| 246 | + |   |   |   |   |   | + |   |   | + |
| 247 | + |   |   |   |   |   |   |   |   |   |
| 248 | − |   |   |   |   |   |   |   |   |   |
| 249 | + |   |   |   |   |   | + | + |   | + |
| 250 | + |   |   |   |   |   | + |   |   | + |
| 251 | + |   |   |   |   |   | + |   | + | + |
| 252 | + |   |   |   |   |   | + |   |   | + |
| 253 | + |   |   |   |   |   | + | + | + | + |
| 254 | + |   |   |   |   |   | + | + | + | + |
| 255 | + |   |   |   |   |   | + |   | + | + |
| 256 | + |   |   |   |   |   | + |   |   | + |
| 257 | + |   |   |   |   |   | + |   |   | + |
| 258 | + |   |   |   |   |   | + |   |   | + |
| 259 | + |   |   |   |   |   | − |   |   | − |
| 260 | + |   |   |   |   |   |   |   |   |   |
| 261 | + |   |   |   |   |   | + |   |   | + |
| 264 | + |   |   |   |   |   | + | + |   | + |
| 265 | + |   |   |   |   |   | + |   |   | + |
| 266 | + |   |   |   |   |   | + |   |   | + |
| 267 | + |   |   |   |   |   | + |   |   | + |
| 268 | + |   |   |   |   |   | + |   |   | + |
| 269 | + |   |   |   |   |   | − |   |   | − |
| 270 | + |   |   |   |   |   | + |   |   | + |
| 271 |   |   |   |   |   |   | + |   |   | + |
| 272 | + |   |   |   |   |   | + |   |   | + |
| 273 | + |   |   |   |   |   | + |   |   | − |
| 274 | + |   |   |   |   |   | + |   |   | − |
| 275 | + |   |   |   |   |   | + |   |   | − |
| 276 | + |   |   |   |   |   | + |   |   | − |
| 277 | + |   |   |   |   |   | + |   |   | + |
| 278 | + |   |   |   |   |   | + |   |   | + |
| 279 | + |   |   |   |   |   | + |   |   | + |
| 280 | + |   |   |   |   |   |   |   |   |   |
| 281 | + |   |   |   |   |   | + |   |   | + |
| 282 | + |   |   |   |   |   | + |   |   | − |
| 283 | + |   |   |   |   |   | + |   |   | − |
| 284 | + |   |   |   |   |   | + |   |   | + |

-continued

| Ex. | APC Flag 8 pt | Cell Titer-Aqueous, A549 6 pt | Cell Titer-Aqueous, HCT116 6 pt | Cell Titer-Aqueous, HELA 6 pt | MDM2-Auto Flag 8 pt | MDM2-P53 Flag 8 pt | PAD Assay, A549 6 pt | PAD Assay, H1299 6 pt | PAD Assay, HCT116 6 pt | PAD Assay, HELA 6 pt |
|---|---|---|---|---|---|---|---|---|---|---|
| 285 | + | | | | | | + | | + | + |
| 286 | + | | | | | | + | | | + |
| 287 | + | | | | | | + | | | + |
| 290 | + | | | | | | + | | | + |
| 291 | + | | | | | | + | | | + |
| 292 | | | | | | | + | | | − |
| 293 | + | | | | | | | | | |
| 294 | | | | | | | + | | | + |
| 295 | | | | | | | + | | | + |
| 296 | − | | | | | | + | | | − |
| 297 | | | | | | | + | | | − |
| 298 | | | | | | | + | | | + |
| 299 | | | | | | | + | | | − |
| 300 | | | | | | | + | | | + |
| 301 | | | | | | | + | | | + |
| 302 | | | | | | | + | | | + |
| 303 | − | | | | | | + | | | + |
| 304 | + | | | | | | + | | | + |
| 305 | | | | | | | + | | | + |
| 306 | | | | | | | − | | | − |
| 307 | − | | | | | | | | | |
| 308 | − | | | | | | | | | |
| 309 | − | | | | | | | | | |
| 310 | − | | | | | | | | | |

"+" indicates that the compound exibits inhibitory activity; "−" indicates that low or no inhibitory activity was observed; a blank indicates that the compound was not tested.

We claim:

1. A compound having the structure:

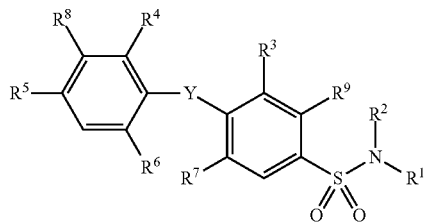

or a pharmaceutically acceptable salt thereof, wherein
$R^1$ is selected from $CF_3$-phenyl, 1-chloro-4-fluorophenyl, 2,4-difluorophenyl, 3,5-dichlorophenyl;
$R^2$ is H, $C_1$-$C_6$-hydrocarbyl, or aryl;
$R^3$ is —H, —Cl, or —$NO_2$;
$R^4$ is —H, —Cl, or —$NO_2$;
$R^5$ is —H or —$NO_2$;
$R^6$ is —H or —Cl;
$R^7$ is —H or —Cl;
$R^8$ is —H or —Cl;
$R^9$ is —H or —F;
$R^{18}$ is —H, $C_1$-$C_6$-hydrocarbyl, —C(O)$R^{19}$, —$SO_2R^{19}$, C(O)NH$R^{19}$, CSNH$R^{19}$, CNNH$R^{19}$, or $CO_2R^{19}$;
$R^{19}$ is —H, —OH, or $C_1$-$C_3$-hydrocarbyl; and
Y is —O—, —S—, —S(O)—, or —$SO_2$—;
  wherein each of the aryl, and hydrocarbyl group of $R^2$ is optionally substituted by one or more groups selected from halo, —OH, —$NH_2$, $C_1$-$C_6$-hydrocarbyl-C(O)—, oxo, $C_1$-$C_6$-hydrocarbyl-(O)—, mono- to per-halogenated $C_1$-$C_6$-hydrocarbyl-O—, $C_1$-$C_6$-hydrocarbyl, mono- to per-halogenated $C_1$-$C_6$-hydrocarbyl, —CN, —$NO_2$, —NO, —$NH_2$, —NH—C(O)$R^{18}$, or —$SO_2$; and provided that the compound is not the following combination:

| $R^1$ | $R^2$ | $R^3$ | $R^4$ | $R^5$ | $R^6$ | $R^7$ | $R^8$ | $R^9$ |
|---|---|---|---|---|---|---|---|---|
| 3,5-dichlorophenyl | H | Cl | Cl | $NO_2$ | H | Cl | H | H. |

2. A compound having the structure:

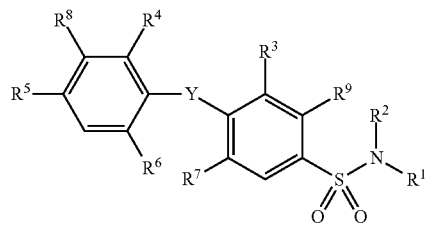

or a pharmaceutically acceptable salt thereof, wherein
$R^1$ and $R^2$ together with the nitrogen atom to which they are both attached form a piperidinyl which is optionally substituted by one or more groups selected from halo, —OH, —$NH_2$, $C_1$-$C_4$-hydrocarbyl-C(O)—, oxo, $C_1$-$C_3$-hydrocarbyl-(O)—, mono- to per-halogenated $C_1$-$C_3$-hydrocarbyl-O—, $C_1$-$C_3$-hydrocarbyl, mono- to per-halogenated $C_1$-$C_3$-hydrocarbyl, aryl-O—, —CN, —$NO_2$, or —$SO_2$;

$R^3$ is —H, —Cl, or —$NO_2$;
$R^4$ is —H, —Cl, or —$NO_2$;
$R^5$ is —H or —$NO_2$;
$R^6$ is —H or —Cl;
$R^7$ is —H or —Cl;
$R^8$ is —H or —Cl;
$R^9$ is —H or —F; and
Y is —O—, —S—, —S(O)—, or —$SO_2$—.

3. The compound according to claim 2 wherein the piperidinyl is 3,5-dimethylpiperidinyl.

4. A compound having the structure:

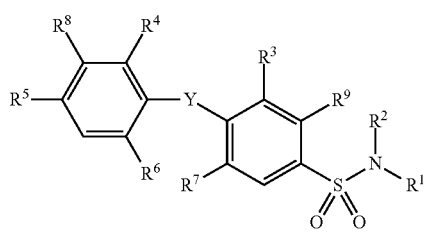

or a pharmaceutically acceptable salt thereof, wherein
$R^1$ is $C_1$-$C_3$-hydrocarbyl-C(=NH)- which is optionally substituted by one or more groups selected from halo, —OH, —$NH_2$, $C_1$-$C_4$-hydrocarbyl-C(O)—, oxo, $C_1$-$C_3$-hydrocarbyl-(O)—, mono- to per-halogenated $C_1$-$C_3$-hydrocarbyl-O—, $C_1$-$C_3$-hydrocarbyl, mono- to per-halogenated $C_1$-$C_3$-hydrocarbyl, aryl-O—, —CN, —$NO_2$, or —$SO_2$;
$R^2$ is H, $C_1$-$C_6$-hydrocarbyl, or aryl;
$R^3$ is —H, —Cl, or —$NO_2$;
$R^4$ is —H, —Cl, or —$NO_2$;
$R^5$ is —H or —$NO_2$;
$R^6$ is —H or —Cl;
$R^7$ is —H or —Cl;
$R^8$ is —H or —Cl;
$R^9$ is —H or —F;
$R^{18}$ is —H, $C_1$-$C_6$-hydrocarbyl, —C(O)$R^{19}$, —$SO_2R^{19}$, C(O)NH$R^{19}$, CSNH$R^{19}$, CNNH$R^{19}$, or $CO_2R^{19}$;
$R^{19}$ is —H, —OH, or $C_1$-$C_3$-hydrocarbyl; and
Y is —O—, —S—, —S(O)—, or —$SO_2$—;
  wherein each of the aryl, and hydrocarbyl group of $R^2$ is optionally substituted by one or more groups selected from halo, —OH, —$NH_2$, $C_1$-$C_6$-hydrocarbyl-C(O)—, oxo, $C_1$-$C_6$-hydrocarbyl-(O)—, mono- to per-halogenated $C_1$-$C_6$-hydrocarbyl-O—, $C_1$-$C_6$-hydrocarbyl, mono- to per-halogenated $C_1$-$C_6$-hydrocarbyl, —CN, —$NO_2$, —NO, —$NH_2$, —NH—C(O)$R^{18}$, or —$SO_2$;
  provided that the compound is not one of the following combinations:

5. The compound according to claim 4 wherein $R^1$ is $CH_3$—C(=NH)—.

6. A compound having the structure:

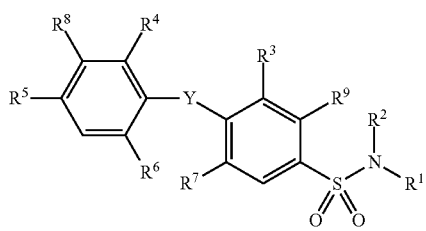

or a pharmaceutically acceptable salt thereof, wherein
$R^1$ is $C_4$-$C_{10}$-hydrocarbyl-NH—CO—$C_6H_4$- which is optionally substituted by one or more groups selected from halo, —OH, —$NH_2$, $C_1$-$C_4$-hydrocarbyl-C(O)—, oxo, $C_1$-$C_3$-hydrocarbyl-(O)—, mono- to per-halogenated $C_{1-3}$-hydrocarbyl-O—, $C_1$-$C_3$-hydrocarbyl, mono- to per-halogenated $C_1$-$C_3$-hydrocarbyl, aryl-O—, —CN, —$NO_2$, or —$SO_2$;
$R^2$ is H, $C_1$-$C_6$-hydrocarbyl, or aryl;
$R^3$ is —H, —Cl, or —$NO_2$;
$R^4$ is —H, —Cl, or —$NO_2$;
$R^5$ is —H or —$NO_2$;
$R^6$ is —H or —Cl;
$R^7$ is —H or —Cl;
$R^8$ is —H or —Cl;
$R^9$ is —H or —F;
$R^{18}$ is —H, $C_1$-$C_6$-hydrocarbyl, —C(O)$R^{19}$, —$SO_2R^{19}$, C(O)NH$R^{19}$, CSNH$R^{19}$, CNNH$R^{19}$, or $CO_2R^{19}$;
$R^{19}$ is —H, —OH, or $C_1$-$C_3$-hydrocarbyl; and
Y is —O—, —S—, —S(O)—, or —$SO_2$—;

| $R^1$ | $R^2$ | $R^3$ | $R^4$ | $R^5$ | $R^6$ | $R^7$ | $R^8$ | $R^9$ |
|---|---|---|---|---|---|---|---|---|
| ![NH/CH2Cl] | H | Cl | Cl | $NO_2$ | H | Cl | H | H. | wherein each of the aryl, and hydrocarbyl group of R² is optionally substituted by one or more groups selected from halo, —OH, —NH₂, C₁-C₆-hydrocarbyl-C(O)—, oxo, C₁-C₆-hydrocarbyl-(O)—, mono- to per-halogenated C₁-C₆-hydrocarbyl-O—, C₁-C₆-hydrocarbyl, mono- to per-halogenated C₁-C₆-hydrocarbyl, —CN, —NO₂, —NO, —NH₂, —NH—C(O)R¹⁸, or —SO₂.

7. The compound according to claim 4 wherein R¹ is cyclopropyl-CH₂—NH—CO-phenyl.

8. A compound having the structure:

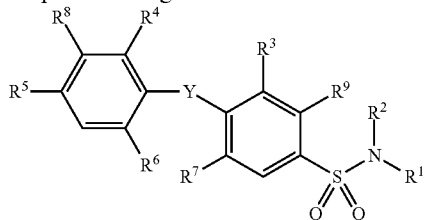

or a pharmaceutically acceptable salt thereof, wherein R¹ is selected from:

-continued
| —CH₃ | CH₃CH₂— | HC≡C—C(CH₃)₂— | CN—(CH₂)₂— |
|---|---|---|---|
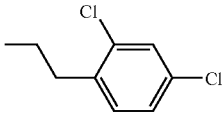 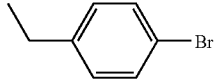 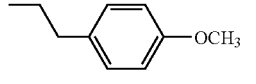 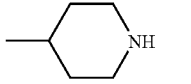 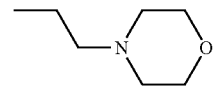
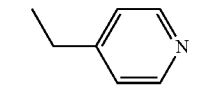 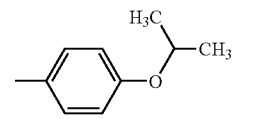 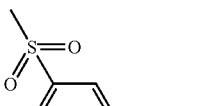  
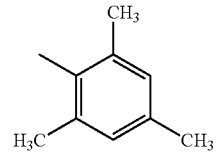 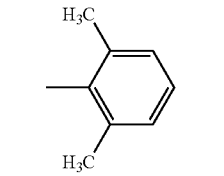 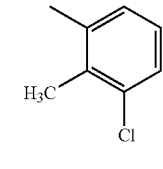 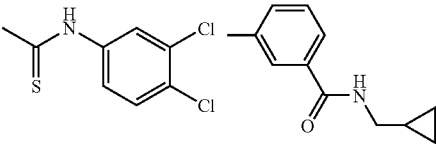 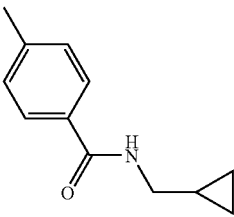
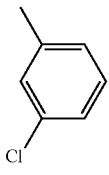 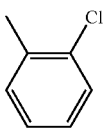 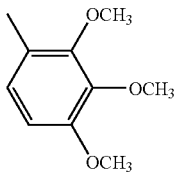 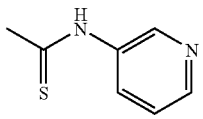 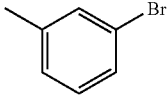
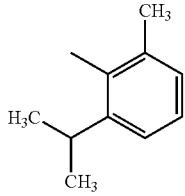 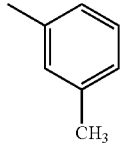 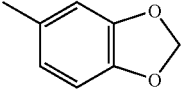 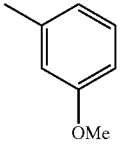 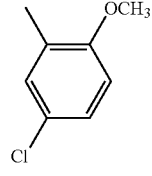
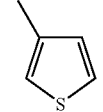  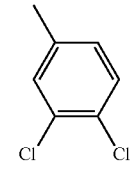 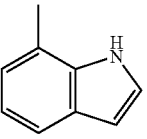 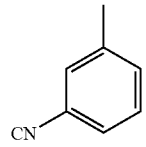
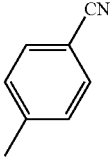 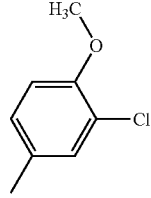 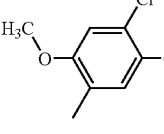 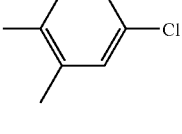

-continued
| —CH₃ | CH₃CH₂— | HC≡C—C(CH₃)₂— | CN—(CH₂)₂— |
|---|---|---|---|
| 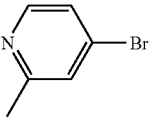 | 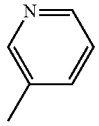 | 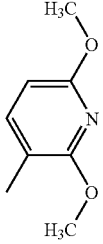 | 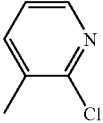 |  |
| 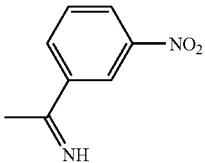 | 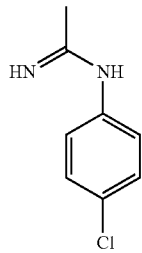 | 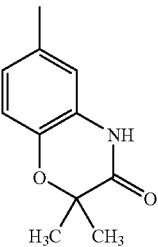 | 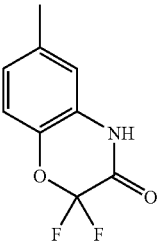 | 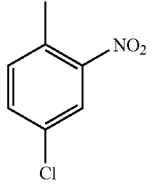 |
| 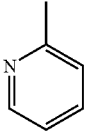 | 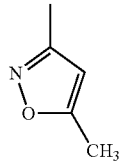 | 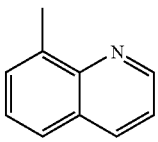 | 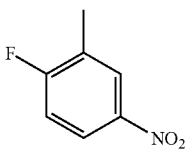 | 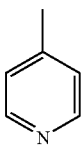 |
| 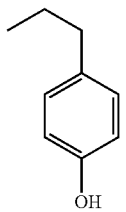 | 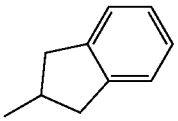 | 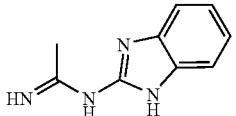 | 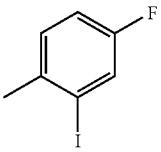 | 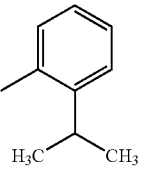 |
| 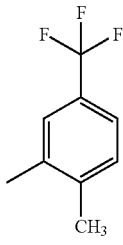 | 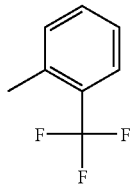 | 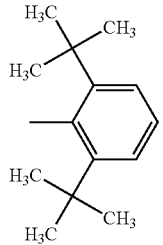 | 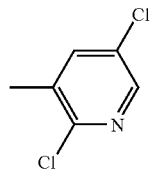 | 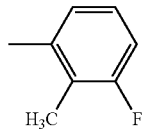 |

-continued
|  | —CH₃ | CH₃CH₂— | HC≡C—C(CH₃)₂— | CN—(CH₂)₂— |
|---|---|---|---|---|
| 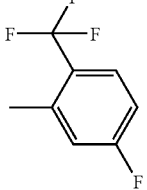 | 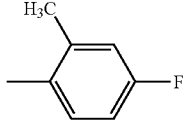 | 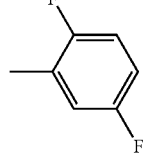 | 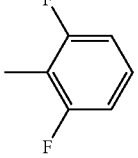 | 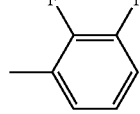 |
| 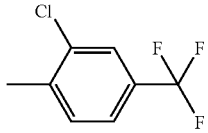 | 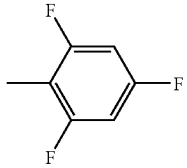 | 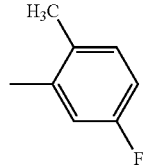 | 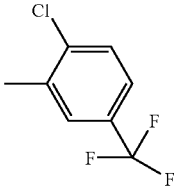 | 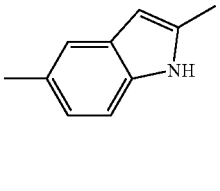 |
| 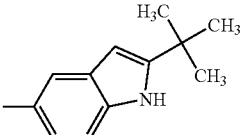 | 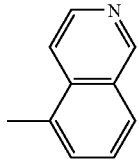 | 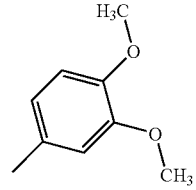 | 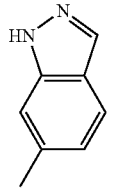 | 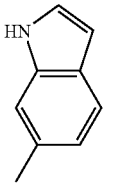 |
| 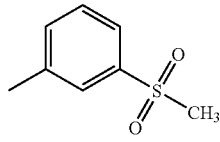 | 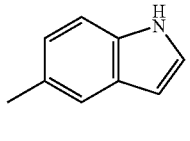 | 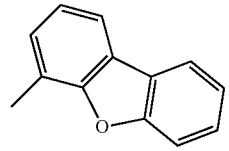 | 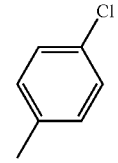 | 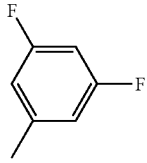 |
| 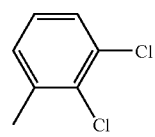 | 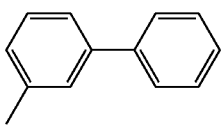 | 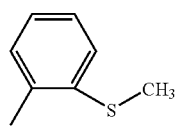 | 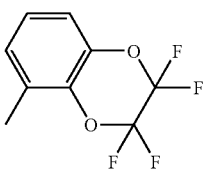 | 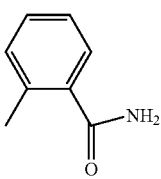 |
| 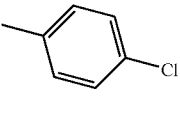 | 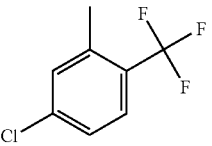 | 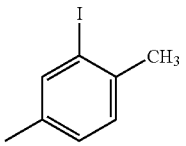 | 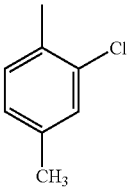 | 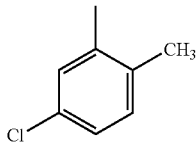 |
| 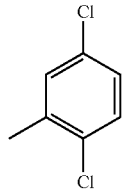 | 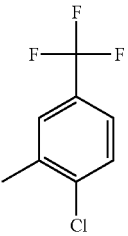 | 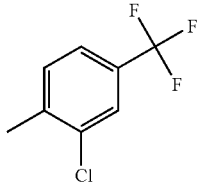 | 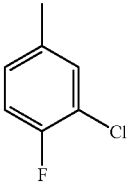 | 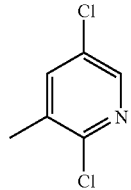 |

-continued
| —CH₃ | CH₃CH₂— | HC≡C—C(CH₃)₂— | CN—(CH₂)₂— |
|---|---|---|---|
| 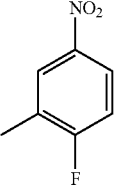 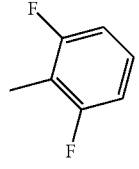 | 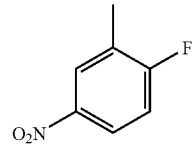 | 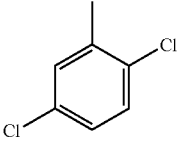 | 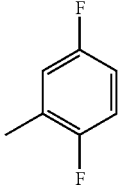 |
| 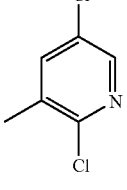 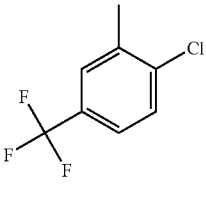 | 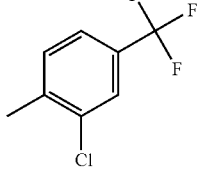 | 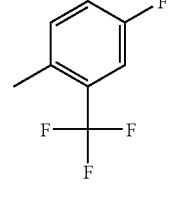 | 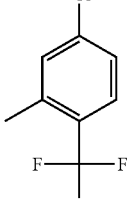 |
| 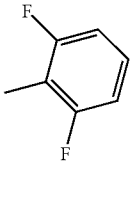 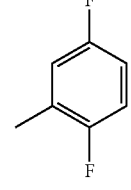 | 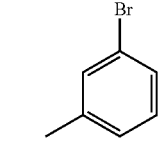 | 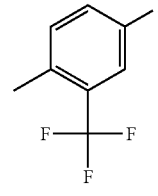 | 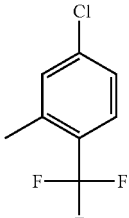 |
| 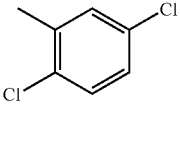 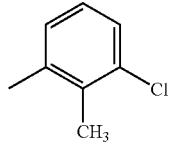 | 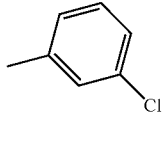 | 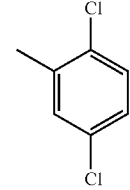 | 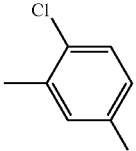 |
| 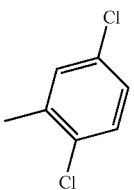 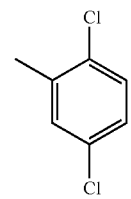 | 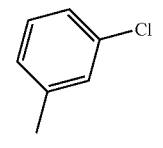 | 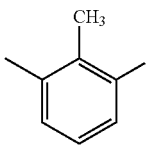 | 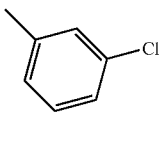 |
| 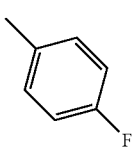 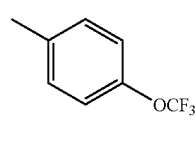 | 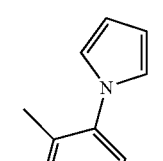 | 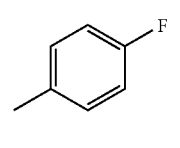 | 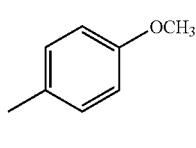 |
| 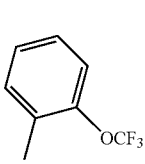 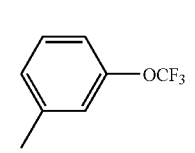 | 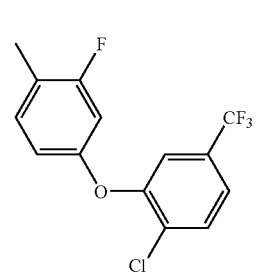 | 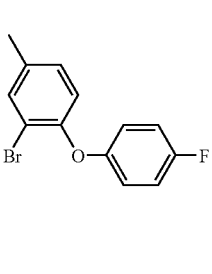 | 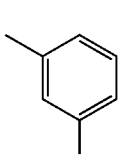 |

-continued

| —CH₃ | CH₃CH₂— | HC≡C—C(CH₃)₂— | CN—(CH₂)₂— |

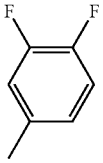 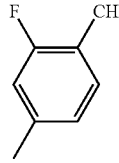 or 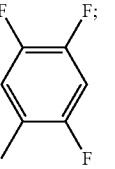

R² is H, C₁-C₆-hydrocarbyl, or aryl;
R³ is —H, —Cl, or —NO₂;
R⁴ is —H, —Cl, or —NO₂;
R⁵ is —H or —NO₂;
R⁶ is —H or —Cl;
R⁷ is —H or —Cl;
R⁸ is —H or —Cl;
R⁹ is —H or —F;
R¹⁸ is —H, C₁-C₆-hydrocarbyl, —C(O)R¹⁹, —SO₂R¹⁹, C(O)NHR¹⁹, CSNHR¹⁹, CNNHR¹⁹, or CO₂R¹⁹;
R¹⁹ is —H, —OH or C₁-C₃-hydrocarbyl; and
Y is —O—, —S—, —S(O)—, or —SO₂—;
  wherein each of the aryl, and hydrocarbyl group of R² is optionally substituted by one or more groups selected from halo, —OH, —NH₂, C₁-C₆-hydrocarbyl-C(O)—, oxo, C₁-C₆-hydrocarbyl-(O)—, mono- to per-halogenated C₁-C₆-hydrocarbyl-O—, C₁-C₆-hydrocarbyl, mono- to per-halogenated C₁-C₆-hydrocarbyl, —CN, —NO₂, —NO, —NH₂, —NH—C(O)R¹⁸, or —SO₂; and
provided that the compound is not one of the following combinations:

9. A compound having the structure:

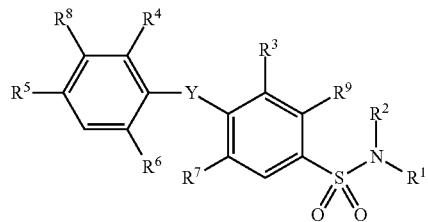

or a pharmaceutically acceptable salt thereof, wherein
R¹ is C₁₋₆-hydrocarbyl, C₅-C₁₂-heterocyclyl-C₀-C₆-hydrocarbyl, aryl-C₁-C₆-hydrocarbyl, C₅-C₁₂-heteroaryl-C₀-C₆-hydrocarbyl, —C(=X)-L¹-R¹⁰, C₄-C₁₀-hydrocarbyl-NH—C(O)—C₆H₄—, aryl-oxy-C₁-C₆-hydrocarbyl-, aryl-oxy-aryl-SO₂—, (CH₃)₂N—C₁-C₆-hydrocarbyl, (NH₂)(NH)C—NH—(CH₂)₃—CH(NH₂CO)—, or =C(R¹³)(R¹⁴);
X is =O, =S, or =NH;

| R¹ | R² | R³ | R⁴ | R⁵ | R⁶ | R⁷ | R⁸ | R⁹ |
|---|---|---|---|---|---|---|---|---|
| 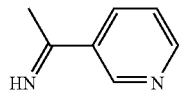 | H | Cl | Cl | NO₂ | H | Cl | H | H |
| 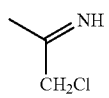 | H | Cl | Cl | NO₂ | H | Cl | H | H |
| 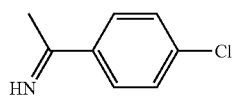 | H | Cl | H | NO₂ | H | Cl | H | H |
| 3,5-dichlorophenyl | H | Cl | Cl | NO₂ | H | Cl | H | H |
| 3-chloro,4-fluorophenyl | H | Cl | Cl | NO₂ | H | Cl | H | H |
| cyclohexyl | H | H | H | NO₂ | H | H | H | H |
| CH₃ | H | H | H | NO₂ | H | H | H | H. |

$L^1$ is a covalent bond, —NH—, —O—, —S—, or $C_1$-$C_3$-hydrocarbyl;

$R^{10}$ is —$C_1$-$C_6$-hydrocarbyl, $C_5$-$C_{12}$-heterocyclyl, aryl, or $C_5$-$C_{12}$-heteroaryl;

$R^2$ is selected from H—, —$CH_3$, —Cl, $CH_3CH_2$—,

 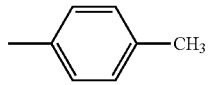

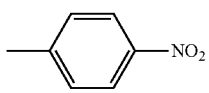 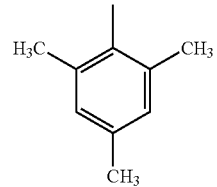

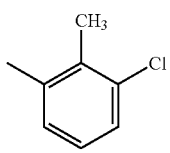 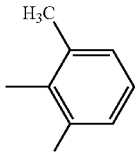 or

-continued $R^3$ is —H, —Cl, or —$NO_2$;
$R^4$ is —H, —Cl, or —$NO_2$;
$R^5$ is —H or —$NO_2$;
$R^6$ is —H or —Cl;
$R^7$ is —H or —Cl;
$R^8$ is —H or —Cl;
$R^9$ is —H or —F;
$R^{18}$ is —H, $C_1$-$C_6$-hydrocarbyl, —C(O)$R^{19}$, —$SO_2R^{19}$, C(O)NH$R^{19}$, CSNH$R^{19}$, CNNH$R^{19}$, or $CO_2R^{19}$;
$R^{19}$ is —H, —OH, or $C_1$-$C_3$-hydrocarbyl; and
Y is —O—, —S—, —S(O)—, or —$SO_2$—;
  wherein each of the aryl, heterocyclyl, and hydrocarbyl group of $R^1$ is optionally substituted by one or more groups selected from halo, —OH, —$NH_2$, $C_1$-$C_6$-hydrocarbyl-C(O)—, oxo, $C_1$-$C_6$-hydrocarbyl-(O)—, mono- to per-halogenated $C_1$-$C_6$-hydrocarbyl-O—, $C_1$-$C_6$-hydrocarbyl, mono- to per-halogenated $C_1$-$C_6$-hydrocarbyl, —CN, —$NO_2$, —NO, —$NH_2$, —NH—C(O)$R^{18}$, or —$SO_2$; and
provided that the compound is not one of the following combinations:

| $R^1$ | $R^2$ | $R^3$ | $R^4$ | $R^5$ | $R^6$ | $R^7$ | $R^8$ | $R^9$ |
|---|---|---|---|---|---|---|---|---|
| 3-acetylpyridyl imine | H | Cl | Cl | $NO_2$ | H | Cl | H | H |
| chloroacetyl imine (CH$_2$Cl) | H | Cl | Cl | $NO_2$ | H | Cl | H | H |
| 4-chlorophenyl acetyl imine | H | Cl | H | $NO_2$ | H | Cl | H | H |
| propyl dimethylamino | —$CH_3$ | $NO_2$ | H | $NO_2$ | H | H | H | H |
| —$CH_3$ | —$CH_3$ | Cl | H | $NO_2$ | H | H | H | H |
| 2-methylthiazolyl | H | H | H | $NO_2$ | H | H | H | H |
| 3,5-dichlorophenyl | H | Cl | Cl | $NO_2$ | H | Cl | H | H |
| 3-chloro,4-fluorophenyl | H | Cl | Cl | $NO_2$ | H | Cl | H | H |
| cyclohexyl | H | H | H | $NO_2$ | H | H | H | H |
| $CH_3$ | $CH_3$ | H | H | $NO_2$ | H | H | H | H |
| $CH_3$ | H | H | H | $NO_2$ | H | H | H | H |
| $CH_3CH_2$ | $CH_3$ | Cl | Cl | $NO_2$ | H | H | H | H |
| $CH_3$C=O | H | H | H | $NO_2$ | H | H | H | H. |

10. A compound having the structure:

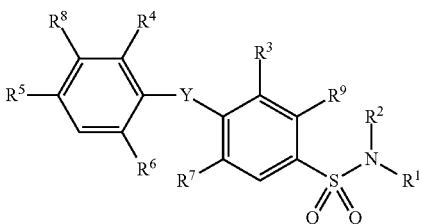

or a pharmaceutically acceptable salt thereof, wherein
$R^1$ and $R^2$ together with the nitrogen to which they are both covalently bound form a moiety selected from

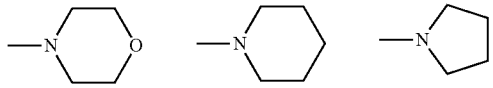

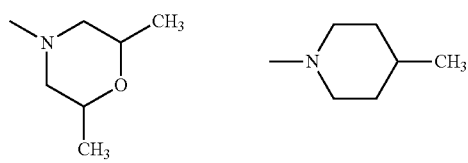

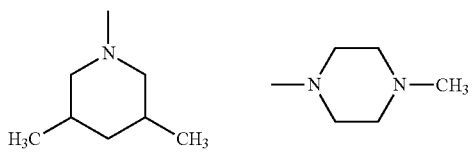

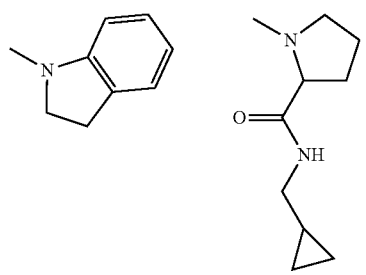

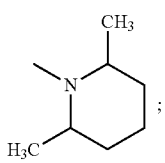

$R^3$ is —H, —Cl, or —NO$_2$;
$R^4$ is —H, —Cl, or —NO$_2$;
$R^5$ is —H or —NO$_2$;
$R^6$ is —H or —Cl;
$R^7$ is —H or —Cl;
$R^8$ is —H or —Cl;
$R^9$ is —H or —F; and
Y is —O—, —S—, —S(O)—, or —SO$_2$—.

11. A compound having the structure:

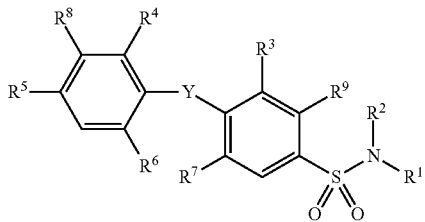

or a pharmaceutically acceptable salt thereof, wherein $R^1$ and $R^2$ together are

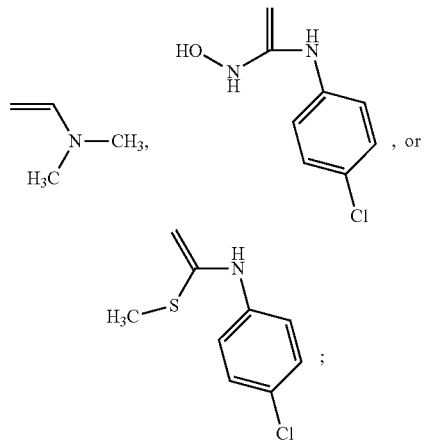

$R^3$ is —H, —Cl, or —NO$_2$;
$R^4$ is —H, —Cl, or —NO$_2$;
$R^5$ is —H or —NO$_2$;
$R^6$ is —H or —Cl;
$R^7$ is —H or —Cl;
$R^8$ is —H or —Cl;
$R^9$ is —H or —F; and
Y is —O—, —S—, —S(O)—, or —SO$_2$—.

12. A compound selected from:
4-(2-chloro-6-nitrophenoxy)-N-(4-fluorophenyl)benzenesulfonamide;
4-{[4-(2-chloro-6-nitrophenoxy)phenyl]sulfonyl}morpholine;
{3-chloro-2-[4-(morpholin-4-ylsulfonyl)phenoxy]phenyl}amine;
4-(2-amino-6-chlorophenoxy)-N-(4-fluorophenyl)benzenesulfonamide;
N-{3-chloro-2-[4-(morpholin-4-ylsulfonyl)phenoxy]phenyl}-2,2,2-trifluoroacetamide;
4-(2-chloro-6-nitrophenoxy)-N-(1-phenylethyl)benzenesulfonamide;
3,5-dichloro-4-(2-chloro-4-nitrophenoxy)-N-[3-(trifluoromethyl)phenyl]benzenesulfonamide;
4-(2-chloro-6-nitrophenoxy)-N-(1,1-dimethylpropyl)benzenesulfonamide;
N-(3-aminopropyl)-4-(2-chloro-6-nitrophenoxy)-N-methylbenzenesulfonamide;
4-{[3,5-dichloro-4-(4-nitrophenoxy)phenyl]sulfonyl}morpholine;
1-{[3,5-dichloro-4-(4-nitrophenoxy)phenyl]sulfonyl}piperidine;
1-{[3,5-dichloro-4-(4-nitrophenoxy)phenyl]sulfonyl}pyrrolidine;

4-{[3,5-dichloro-4-(4-nitrophenoxy)phenyl]sulfonyl}-2,6-dimethylmorpholine;
3,5-dichloro-N-(3-chloro-4-fluorophenyl)-4-(2-chloro-4-nitrophenoxy)benzenesulfonamide;
3,5-dichloro-4-(2-chloro-4-nitrophenoxy)-N-(2,4-difluorophenyl)benzenesulfonamide;
1-{[3,5-dichloro-4-(2-chloro-4-nitrophenoxy)phenyl]sulfonyl}-3,5-dimethylpiperidine;
3,5-dichloro-4-(2-chloro-4-nitrophenoxy)-N-(4-fluorophenyl)benzenesulfonamide;
3,5-dichloro-4-(2-chloro-4-nitrophenoxy)-N-(3,5-dichlorophenyl)benzenesulfonamide;
4-chloro-N-{[3,5-dichloro-4-(2-chloro-4-nitrophenoxy)phenyl]sulfonyl}benzene-carboximidamide;
2-chloro-N-{[3,5-dichloro-4-(2-chloro-4-nitrophenoxy)phenyl]sulfonyl}ethanimidamide;
N-{[3,5-dichloro-4-(4-nitrophenoxy)phenyl]sulfonyl}pyridine-3-carboximidamide;
N-{[3,5-dichloro-4-(4-nitrophenoxy)phenyl]sulfonyl}pyridine-4-carboximidamide;
N-{[3,5-dichloro-4-(4-nitrophenoxy)phenyl]sulfonyl}ethanimidamide;
4-(2-chloro-6-nitrophenoxy)benzenesulfonamide;
4-(2-chloro-6-nitrophenoxy)-N-[(1E)-(dimethylamino)methylene]benzenesulfonamide;
4-(2-chloro-6-nitrophenoxy)-N-(1,1-dimethylpropyl)benzenesulfonamide;
N-(3-aminopropyl)-4-(2-chloro-6-nitrophenoxy)-N-methylbenzenesulfonamide;
4-{[3,5-dichloro-4-(4-nitrophenoxy)phenyl]sulfonyl}morpholine;
1-{[3,5-dichloro-4-(4-nitrophenoxy)phenyl]sulfonyl}piperidine;
1-{[3,5-dichloro-4-(4-nitrophenoxy)phenyl]sulfonyl}pyrrolidine;
4-{[3,5-dichloro-4-(4-nitrophenoxy)phenyl]sulfonyl}-2,6-dimethylmorpholine;
4-{[3,5-dichloro-4-(2-chloro-4-nitrophenoxy)phenyl]sulfonyl}morpholine;
3,5-dichloro-N-(3-chloro-4-fluorophenyl)-4-(2-chloro-4-nitrophenoxy)benzene-sulfonamide;
3,5-dichloro-4-(2-chloro-4-nitrophenoxy)-N-(2,4-difluorophenyl)benzenesulfonamide;
4-{[3,5-dichloro-4-(2-chloro-4-nitrophenoxy)phenyl]sulfonyl}-2,6-dimethylmorpholine;
1-{[3,5-dichloro-4-(2-chloro-4-nitrophenoxy)phenyl]sulfonyl}-4-methylpiperidine;
1-{[3,5-dichloro-4-(2-chloro-4-nitrophenoxy)phenyl]sulfonyl}-3,5-dimethylpiperidine;
1-{[3,5-dichloro-4-(2-chloro-4-nitrophenoxy)phenyl]sulfonyl}piperidine;
1-{[3,5-dichloro-4-(2-chloro-4-nitrophenoxy)phenyl]sulfonyl}pyrrolidine;
3,5-dichloro-4-(2-chloro-4-nitrophenoxy)-N-(4-fluorophenyl)benzenesulfonamide;
3,5-dichloro-4-(2-chloro-4-nitrophenoxy)-N-(3,5-dichlorophenyl)benzenesulfonamide;
3,5-dichloro-N-(3-chloro-2-methylphenyl)-4-(2-chloro-4-nitrophenoxy)benzene-sulfonamide;
3,5-dichloro-4-(2-chloro-4-nitrophenoxy)-N-{[(3,4-dichlorophenyl)amino]carbonothioyl}benzene sulfonamide;
3,5-dichloro-4-(2-chloro-4-nitrophenoxy)-N-[(1Z)-[(4-chlorophenyl)amino](hydroxy-amino)methylene]benzenesulfonamide;
N-{[3,5-dichloro-4-(2-chloro-4-nitrophenoxy)phenyl]sulfonyl}pyridine-4-carboximidamide;
2-chloro-N-{[3,5-dichloro-4-(4-nitrophenoxy)phenyl]sulfonyl}ethanimidamide;
4-chloro-N-{[3,5-dichloro-4-(4-nitrophenoxy)phenyl]sulfonyl}benzenecarboximidamide;
N-(3-bromophenyl)-3,5-dichloro-4-(2-chloro-4-nitrophenoxy)benzenesulfonamide;
4-[2-(aminomethyl)-3-chlorophenoxy]-N-phenylbenzenesulfonamide;
{2-chloro-6-[4-(morpholin-4-ylsulfonyl)phenoxy]benzyl}amine;
4-[2-(aminomethyl)-3-chlorophenoxy]-N-(4-chlorobenzyl)benzenesulfonamide;
4-[2-(aminomethyl)-3-chlorophenoxy]-N-benzyl-N-methylbenzenesulfonamide;
{2-[4-(morpholin-4-ylsulfonyl)phenoxy]-1,3-phenylene}dimethanamine;
4-[2,6-bis(aminomethyl)phenoxy]-N-phenylbenzenesulfonamide;
4-(2-chloro-6-nitrophenoxy)-N-(4-fluorophenyl)benzenesulfonamide;
p4-{[4-(2-chloro-6-nitrophenoxy)phenyl]sulfonyl}morpholine;
3-chloro-2-[4-(morpholin-4-ylsulfonyl)phenoxy]aniline;
4-(2-amino-6-chlorophenoxy)-N-(4-fluorophenyl)benzenesulfonamide;
N-{3-chloro-2-[4-(morpholin-4-ylsulfonyl)phenoxy]phenyl}-2,2,2-trifluoroacetamide;
4-(2-chloro-6-nitrophenoxy)-N-(1-phenylethyl)benzenesulfonamide;
4-[2-(aminomethyl)-3-chlorophenoxy]-N-(2,4-dichlorophenyl)benzenesulfonamide;
3,5-dichloro-N-[(1E)-(dimethylamino)methylene]-4-(4-nitrophenoxy)benzene-sulfonamide;
4-[2-(aminomethyl)-3-chlorophenoxy]-N-(1,2,2-trimethylpropyl)benzenesulfonamide;
4-[2-(aminomethyl)-3-chlorophenoxy]-N-phenylbenzenesulfonamide;
1-{2-chloro-6-[4-(morpholin-4-ylsulfonyl)phenoxy]phenyl}methanamine;
4-[2-(aminomethyl)-3-chlorophenoxy]-N-(4-chlorobenzyl)benzenesulfonamide;
4-[2-(aminomethyl)-3-chlorophenoxy]-N-benzyl-N-methylbenzenesulfonamide;
{2-[4-(morpholin-4-ylsulfonyl)phenoxy]-1,3-phenylene}dimethanamine;
4-[2,6-bis(aminomethyl)phenoxy]-N-phenylbenzenesulfonamide;
3,5-dichloro-N-[(1E)-(dimethylamino)methylene]-4-(4-nitrophenoxy)benzene-sulfonamide;
4-[2-(aminomethyl)-3-chlorophenoxy]-N-(1,2,2-trimethylpropyl)benzenesulfonamide;
N-(3-fluorophenyl)-4-(4-nitrophenoxy)benzenesulfonamide;
4,4'-oxybis(N,N-diethylbenzenesulfonamide);
1-{[4-(4-nitrophenoxy)phenyl]sulfonyl}piperidine;
1-methyl-4-{[4-(4-nitrophenoxy)phenyl]sulfonyl}piperazine;
4-chloro-N-{4-[4-(morpholin-4-ylsulfonyl)phenoxy]phenyl}benzenesulfonamide;
N-cyclohexyl-4-(4-nitrophenoxy)benzenesulfonamide;
4-(4-nitrophenoxy)-N-phenylbenzenesulfonamide;
4,4'-oxybis[N-(3-nitrophenyl)benzenesulfonamide];
N-(3-nitrophenyl)-4-phenoxybenzenesulfonamide;
N-(3-acetylphenyl)-4-(4-nitrophenoxy)benzenesulfonamide;
N-(2-methoxyphenyl)-4-(4-nitrophenoxy)benzenesulfonamide;

1-{[4-(4-nitrophenoxy)phenyl]sulfonyl}indoline;
1,1'-[oxybis(4,1-phenylenesulfonyl)]dipiperidine;
4-{[4-(4-nitrophenoxy)phenyl]sulfonyl}morpholine;
N,N-diethyl-4-(4-nitrophenoxy)benzenesulfonamide;
4,4'-oxybis(N,N-diethylbenzenesulfonamide);
1,1'-[oxybis(4,1-phenylenesulfonyl)]dipiperidine;
N-{4-[4-(morpholin-4-ylsulfonyl)phenoxy]phenyl}-4-phenoxybenzamide;
N-{4-[4-(morpholin-4-ylsulfonyl)phenoxy]phenyl}-4-nitrobenzamide;
4,4'-oxybis[N-(4-methylphenyl)benzenesulfonamide];
4-{[4-(4-nitrophenoxy)phenyl]sulfonyl}morpholine;
N-(3-nitrophenyl)-4-phenoxybenzenesulfonamide;
N-(3-acetylphenyl)-4-(4-nitrophenoxy)benzenesulfonamide;
4-({4-[2,6-dinitro-4-(trifluoromethyl)phenoxy]phenyl}sulfonyl)morpholine;
1-({4-[2,6-dinitro-4-(trifluoromethyl)phenoxy]phenyl}sulfonyl)-4-methylpiperazine;
4-[2,6-dinitro-4-(trifluoromethyl)phenoxy]-N-(pyridin-2-ylmethyl)benzenesulfonamide;
N-(5-chloropyridin-2-yl)-4-phenoxybenzenesulfonamide;
1-{[4-(2,4-dichlorophenoxy)-2-fluorophenyl]sulfonyl}piperidine;
N-(cyclopropylmethyl)-2-({[3,5-dichloro-4-(2-chloro-4-nitrophenoxy)phenyl]sulfonyl}amino)benzamide;
3,5-dichloro-4-(2-chloro-4-nitrophenoxy)-N-[3-(3,5-dichlorophenoxy)propyl]benzene-sulfonamide;
3,5-dichloro-4-(2-chloro-4-nitrophenoxy)-N-[2-(2,4-dichlorophenyl)ethyl]benzene-sulfonamide;
3,5-dichloro-4-(2-chloro-4-nitrophenoxy)-N-(pyridin-4-ylmethyl)benzenesulfonamide;
3,5-dichloro-4-(2-chloro-4-nitrophenoxy)-N-(4-isopropoxyphenyl)benzenesulfonamide;
3,5-dichloro-4-(2-chloro-4-nitrophenoxy)-N-methylbenzenesulfonamide;
3,5-dichloro-4-(2-chloro-4-nitrophenoxy)-N-(4-cyanophenyl)-N-(1,3-dichloro-2-(2-chloro-4-nitrophenoxy)-5-sulfonylbenzene)-benzenesulfonamide;
3,5-dichloro-4-(2-chloro-4-nitrophenoxy)-N-(4-methylphenyl)-N-(1,3-dichloro-2-(2-chloro-4-nitrophenoxy)-5-sulfonylbenzene)benzenesulfonamide;
3,5-dichloro-4-(2-chloro-4-nitrophenoxy)-N-(1,3-dichloro-2-(2-chloro-4-nitrophenoxy)-5-sulfonylbenzene)-N-(4-nitrophenyl)benzenesulfonamide;
1-{[3,5-dichloro-4-(2-chloro-4-nitrophenoxy)phenyl]sulfonyl}-2,6-dimethylpiperidine
3,5-dichloro-4-(2-chloro-4-nitrophenoxy)-N-mesityl-N-(1,3-dichloro-2-(2-chloro-4-nitrophenoxy)-5-sulfonylbenzene)benzenesulfonamide;
3,5-dichloro-N-(3-chloro-2-methylphenyl)-4-(2-chloro-4-nitrophenoxy)-N-(1,3-dichloro-2-(2-chloro-4-nitrophenoxy)-5-sulfonylbenzene)benzenesulfonamide;
3,5-dichloro-4-(2-chloro-4-nitrophenoxy)-N-mesitylbenzenesulfonamide;
3,5-dichloro-4-(2-chloro-4-nitrophenoxy)-N-(2,6-dimethylphenyl)-N-(1,3-dichloro-2-(2-chloro-4-nitrophenoxy)-5-sulfonylbenzene)benzenesulfonamide;
3,5-dichloro-4-(2-chloro-4-nitrophenoxy)-N-(2,6-dimethylphenyl)benzenesulfonamide;
3,5-dichloro-N-(3-chloro-2-methylphenyl)-4-(2-chloro-4-nitrophenoxy)benzene-sulfonamide;
3,5-dichloro-4-(2-chloro-4-nitrophenoxy)-N-{[(3,4-dichlorophenyl)amino]carbonothioyl}benzene sulfonamide;
methylN-(4-chlorophenyl)-N'-{[3,5-dichloro-4-(2-chloro-4-nitrophenoxy)phenyl]sulfonyl}imidothio carbamate;
3,5-dichloro-4-(2-chloro-4-nitrophenoxy)-N-[(1Z)-[(4-chlorophenyl)amino](hydroxyamino)methylene]benzenesulfonamide;
N-(cyclopropylmethyl)-3-({[3,5-dichloro-4-(2-chloro-4-nitrophenoxy)phenyl]sulfonyl}amino)benzamide;
N-(cyclopropylmethyl)-4-({[3,5-dichloro-4-(2-chloro-4-nitrophenoxy)phenyl]sulfonyl}amino)benzamide;
3,5-dichloro-4-(2-chloro-4-nitrophenoxy)-N-(3-chlorophenyl)benzenesulfonamide;
3,5-dichloro-N-(3-chloro-4-methoxyphenyl)-4-(2-chloro-4-nitrophenoxy)-N-(1,3-dichloro-2-(2-chloro-4-nitrophenoxy)-5-sulfonylbenzene)benzenesulfonamide;
3,5-dichloro-4-(2-chloro-4-nitrophenoxy)-N-(2-chlorophenyl)benzenesulfonamide;
3,5-dichloro-4-(2-chloro-4-nitrophenoxy)-N-(2,3,4-trimethoxyphenyl)benzene-sulfonamide;
N-(3-bromophenyl)-3,5-dichloro-4-(2-chloro-4-nitrophenoxy)benzenesulfonamide;
3,5-dichloro-4-(2-chloro-4-nitrophenoxy)-N-(2-isopropyl-6-methylphenyl)benzene-sulfonamide;
3,5-dichloro-4-(2-chloro-4-nitrophenoxy)-N-(3-methylphenyl)benzenesulfonamide;
N-1,3-benzodioxol-5-yl-3,5-dichloro-4-(2-chloro-4-nitrophenoxy)benzenesulfonamide;
3,5-dichloro-4-(2-chloro-4-nitrophenoxy)-N-(3-methoxyphenyl)benzenesulfonamide;
3,5-dichloro-N-(5-chloro-2-methoxyphenyl)-4-(2-chloro-4-nitrophenoxy)benzene-sulfonamide;
3,5-dichloro-4-(2-chloro-4-nitrophenoxy)-N-3-thienylbenzenesulfonamide;
3,5-dichloro-4-(2-chloro-4-nitrophenoxy)-N-(2-fluoro-3-methoxyphenyl)benzene-sulfonamide;
3,5-dichloro-4-(2-chloro-4-nitrophenoxy)-N-(3,4-dichlorophenyl)benzenesulfonamide;
3,5-dichloro-4-(2-chloro-4-nitrophenoxy)-N-1H-indol-7-ylbenzenesulfonamide;
3,5-dichloro-4-(2-chloro-4-nitrophenoxy)-N-(3-cyanophenyl)benzenesulfonamide;
3,5-dichloro-4-(2-chloro-4-nitrophenoxy)-N-(3,4-dimethoxyphenyl)benzenesulfonamide;
3,5-dichloro-4-(2-chloro-4-nitrophenoxy)-N-1H-indol-6-ylbenzenesulfonamide;
3,5-dichloro-4-(2-chloro-4-nitrophenoxy)-N-1H-indol-5-ylbenzenesulfonamide;
3,5-dichloro-4-(2-chloro-4-nitrophenoxy)-N-dibenzo[b,d]furan-4-ylbenzenesulfonamide;
3,5-dichloro-4-(2-chloro-4-nitrophenoxy)-N-(3,5-difluorophenyl)benzenesulfonamide;
3,5-dichloro-4-(2-chloro-4-nitrophenoxy)-N-(2,3-dichlorophenyl)benzenesulfonamide;
N-biphenyl-3-yl-3,5-dichloro-4-(2-chloro-4-nitrophenoxy)benzenesulfonamide;
3,5-dichloro-4-(2-chloro-4-nitrophenoxy)-N-(2,2,3,3-tetrafluoro-2,3-dihydro-1,4-benzodioxin-5-yl)benzenesulfonamide;
3,5-dichloro-4-(2-chloro-4-nitrophenoxy)-N-(3,4-difluorophenyl)benzenesulfonamide;
3,5-dichloro-4-(2-chloro-4-nitrophenoxy)-N-(3-fluoro-4-methylphenyl)benzene-sulfonamide;
3,5-dichloro-4-(2-chloro-4-nitrophenoxy)-N-(2,4,5-trifluorophenyl)benzenesulfonamide;
3,5-dichloro-4-(2-chloro-4-nitrophenoxy)-N-(4-cyanophenyl)benzenesulfonamide;

3,5-dichloro-N-(3-chloro-4-methoxyphenyl)-4-(2-chloro-4-nitrophenoxy)benzene-sulfonamide;
3,5-dichloro-N-(4-chloro-2,5-dimethoxyphenyl)-4-(2-chloro-4-nitrophenoxy)benzene-sulfonamide;
3,5-dichloro-4-(2-chloro-4-nitrophenoxy)-N-(2,5-dichlorophenyl)benzenesulfonamide;
N-(4-bromopyridin-2-yl)-3,5-dichloro-4-(2-chloro-4-nitrophenoxy)benzenesulfonamide;
3,5-dichloro-4-(2-chloro-4-nitrophenoxy)-N-(2,6-dimethoxypyridin-3-yl)benzene-sulfonamide;
3,5-dichloro-4-(2-chloro-4-nitrophenoxy)-N-(2-chloropyridin-3-yl)benzenesulfonamide;
3,5-dichloro-4-(2-chloro-4-nitrophenoxy)-N-(4-methoxyphenyl)benzenesulfonamide;
3,5-dichloro-4-(2-chloro-4-nitrophenoxy)-N-(2-iodophenyl)benzenesulfonamide;
N-{[3,5-dichloro-4-(2-chloro-4-nitrophenoxy)phenyl]sulfonyl}-3-nitrobenzene-carboximidamide;
3,5-dichloro-4-(2-chloro-4-nitrophenoxy)-N-[[(4-chlorophenyl)amino](imino)methyl]benzene sulfonamide;
3,5-dichloro-4-(2-chloro-4-nitrophenoxy)-N-(2,2-dimethyl-3-oxo-3,4-dihydro-2H-1,4-benzoxazin-6-yl)benzenesulfonamide;
3,5-dichloro-4-(2-chloro-4-nitrophenoxy)-N-(2,2-difluoro-3-oxo-3,4-dihydro-2H-1,4-benzoxazin-6-yl)benzenesulfonamide;
3,5-dichloro-4-(2-chloro-4-nitrophenoxy)-N-(4-chloro-2-nitrophenyl)benzene-sulfonamide;
3,5-dichloro-4-(2-chloro-4-nitrophenoxy)-N-pyridin-2-ylbenzenesulfonamide;
3,5-dichloro-4-(2-chloro-4-nitrophenoxy)-N-(4,6-dibromopyridin-2-yl)benzene-sulfonamide;
3,5-dichloro-4-(2-chloro-4-nitrophenoxy)-N-quinolin-8-ylbenzenesulfonamide;
3,5-dichloro-4-(2-chloro-4-nitrophenoxy)-N-(2-fluoro-5-nitrophenyl)benzene-sulfonamide;
3,5-dichloro-4-(2-chloro-4-nitrophenoxy)-N-(2,3-dihydro-1H-inden-2-yl)benzene-sulfonamide;
N-[(1H-benzimidazol-2-ylamino)(imino)methyl]-3,5-dichloro-4-(2-chloro-4-nitrophenoxy)benzene sulfonamide;
3,5-dichloro-4-(2-chloro-4-nitrophenoxy)-N-[2-methyl-3-(trifluoromethyl)phenyl]benzenesulfonamide;
3,5-dichloro-4-(2-chloro-4-nitrophenoxy)-N-[2-methyl-5-(trifluoromethyl)phenyl]benzenesulfonamide;
3,5-dichloro-4-(2-chloro-4-nitrophenoxy)-N-[2-(trifluoromethyl)phenyl]benzenesulfonamide;
3,5-dichloro-4-(2-chloro-4-nitrophenoxy)-N-(2,6-di-tert-butylphenyl)benzenesulfonamide;
3,5-dichloro-4-(2-chloro-4-nitrophenoxy)-N-(3-fluorophenyl)benzenesulfonamide;
3,5-dichloro-4-(2-chloro-4-nitrophenoxy)-N-(3-fluoro-2-methylphenyl)benzenesulfonamide;
3,5-dichloro-4-(2-chloro-4-nitrophenoxy)-N-[5-fluoro-2-(trifluoromethyl)phenyl]benzene sulfonamide;
3,5-dichloro-4-(2-chloro-4-nitrophenoxy)-N-(4-fluoro-2-methylphenyl)benzene-sulfonamide;
3,5-dichloro-4-(2-chloro-4-nitrophenoxy)-N-(2,6-difluorophenyl)benzenesulfonamide;
3,5-dichloro-4-(2-chloro-4-nitrophenoxy)-N-(5-fluoro-2-methylphenyl)benzene-sulfonamide;
N-{3-chloro-4-[2,6-dinitro-4-(trifluoromethyl)phenoxy]phenyl}-4-methylbenzenesulfonamide;
4-chloro-N-{3-chloro-4-[2,6-dinitro-4-(trifluoromethyl)phenoxy]phenyl}benzene-sulfonamide;
3,5-dichloro-N-[5-chloro-2-(trifluoromethyl)phenyl]-4-(2,4-dichlorophenoxy)benzene-sulfonamide;
3,5-dichloro-4-(2-chloro-4-nitrophenoxy)-N-(3-iodo-4-methylphenyl)benzene-sulfonamide;
3,5-dichloro-N-(2-chloro-4-methylphenyl)-4-(2-chloro-4-nitrophenoxy)benzene-sulfonamide;
3,5-dichloro-N-(5-chloro-2-methylphenyl)-4-(2-chloro-4-nitrophenoxy)benzene-sulfonamide;
3-chloro-N-(2-fluoro-5-nitrophenyl)-4-[4-nitro-2-(trifluoromethyl)phenoxy]benzene-sulfonamide;
3-chloro-N-(2,5-dichlorophenyl)-4-[4-nitro-2-(trifluoromethyl)phenoxy]benzene-sulfonamide;
3-chloro-N-(2,5-difluorophenyl)-4-[4-nitro-2-(trifluoromethyl)phenoxy]benzene-sulfonamide;
3-chloro-N-(2,5-dichloropyridin-3-yl)-4-[4-nitro-2-(trifluoromethyl)phenoxy]benzene-sulfonamide;
3-chloro-N-[2-chloro-5-(trifluoromethyl)phenyl]-4-[4-nitro-2-(trifluoromethyl)phenoxy]benzene sulfonamide;
3-chloro-N-[2-chloro-4-(trifluoromethyl)phenyl]-4-[4-nitro-2-(trifluoromethyl)phenoxy]benzene sulfonamide;
3-chloro-N-[4-fluoro-2-(trifluoromethyl)phenyl]-4-[4-nitro-2-(trifluoromethyl)phenoxy]benzene sulfonamide;
3-chloro-N-[5-chloro-2-(trifluoromethyl)phenyl]-4-[4-nitro-2-(trifluoromethyl)phenoxy]benzene sulfonamide;
3-chloro-N-(2,6-difluorophenyl)-4-[4-nitro-2-(trifluoromethyl)phenoxy]benzene-sulfonamide;
N-(3-bromophenyl)-3-chloro-4-[4-nitro-2-(trifluoromethyl)phenoxy]benzene-sulfonamide;
2,5-dichloro-N-[4-(4-nitrophenoxy)phenyl]benzene-sulfonamide;
3-chloro-2-methyl-N-[4-(4-nitrophenoxy)phenyl]benzenesulfonamide;
3-chloro-N-[4-(4-nitrophenoxy)phenyl]benzenesulfonamide;
2,5-dichloro-N-[4-(4-chlorophenoxy)phenyl]benzene-sulfonamide;
2,5-dichloro-N-{4-[2-chloro-5-(trifluoromethyl)phenoxy]-2-fluorophenyl}benzene-sulfonamide;
N-[3-bromo-4-(4-fluorophenoxy)phenyl]-2,5-dichlorobenzenesulfonamide;
2,5-dichloro-N-[4-(2,4,6-trichlorophenoxy)phenyl]benzenesulfonamide;
N-acetyl-N-[3-chloro-4-(2,6-dichloro-4-{[(3-chlorophenyl)amino]sulfonyl}phenoxy)phenyl]acetamide;
N-[3-bromo-4-(4-fluorophenoxy)phenyl]-3-chloro-2-methylbenzenesulfonamide;
N-[3-bromo-4-(4-fluorophenoxy)phenyl]-3-chlorobenzenesulfonamide;
N-[3-bromo-4-(4-fluorophenoxy)phenyl]-4-fluorobenzenesulfonamide;
N-[3-bromo-4-(4-fluorophenoxy)phenyl]-4-(trifluoromethoxy)benzenesulfonamide;
3,5-dichloro-4-(2-chloro-4-nitrophenoxy)-N-[2-(1H-pyrrol-1-yl)phenyl]benzene-sulfonamide;
N-{4-[2-chloro-5-(trifluoromethyl)phenoxy]-2-fluorophenyl}-4-fluorobenzene-sulfonamide;
N-{4-[2-chloro-5-(trifluoromethyl)phenoxy]-2-fluorophenyl}-4-methoxybenzene-sulfonamide;
3,5-dichloro-4-(2-chloro-4-nitrophenoxy)-N-[2-(trifluoromethoxy)phenyl]benzene-sulfonamide;
3,5-dichloro-4-(2-chloro-4-nitrophenoxy)-N-[3-(trifluoromethoxy)phenyl]benzene-sulfonamide;
3,5-dichloro-4-(2-chloro-4-nitrophenoxy)-N-{4-[2-chloro-5-(trifluoromethyl)phenoxy]-2-fluorophenyl}benzenesulfonamide;
N-[3-bromo-4-(4-fluorophenoxy)phenyl]-3,5-dichloro-4-(2-chloro-4-nitrophenoxy) benzenesulfonamide;
or a pharmaceutically acceptable salt thereof.

13. A compound having the structure:

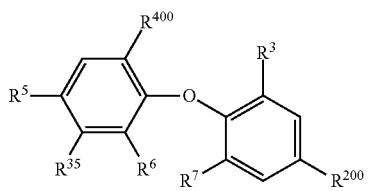

or a pharmaceutically acceptable salt thereof, wherein
$R^{200}$ is —S(O)$_2$—N(R$^1$)(R$^2$);
$R^1$ is phenyl substituted with halogen, trifluoromethoxy or both,
$R^2$ is hydrogen;
$R^3$ is halo;
$R^{400}$ is halo;
$R^5$ is NO$_2$;
$R^{35}$ is —H;
$R^6$ is —H;
$R^7$ is halo;
$R^{17}$ is —H or —C$_1$-C$_6$-hydrocarbyl;
$R^{18}$ is —H, C$_1$-C$_6$-hydrocarbyl, —C(O)R$^{19}$, —SO$_2$R$^{19}$, C(O)NHR$^{19}$, CSNHR$^{19}$, CNNHR$^{19}$, or CO$_2$R$^{19}$;
$R^{19}$ is —H, —OH, or C$_1$-C$_3$-hydrocarbyl;

wherein each of the aryl, heteroaryl, heterocyclyl, and hydrocarbyl groups above is optionally substituted by one or more groups selected from halo, —OH, —NH$_2$, C$_1$-C$_6$-hydrocarbyl-C(O)—, oxo, C$_1$-C$_6$-hydrocarbyl-(O)—, mono- to per-halogenated C$_1$-C$_6$-hydrocarbyl-O—, C$_1$-C$_6$-hydrocarbyl, mono- to per-halogenated C$_1$-C$_6$-hydrocarbyl, —CN, —NO$_2$, —NO, —NH$_2$, —NH—C(O)R$^{18}$, or —SO$_2$;

provided that when R$^{35}$ is H, the compound is not one of the following combinations:

| R$^1$ | R$^2$ | R$^3$ | R$^{400}$ | R$^5$ | R$^6$ | R$^7$ |
|---|---|---|---|---|---|---|
| 3,5-dichlorophenyl | H | Cl | Cl | NO$_2$ | H | Cl |
| 3-chloro-4-fluorophenyl | H | Cl | Cl | NO$_2$ | H | Cl. |

14. A compound selected from:
N-(2-bromo-5-(trifluoromethoxy)phenyl)-3,5-dichloro-4-(2-chloro-4-nitrophenoxy)benzenesulfonamide;
N-(3-bromo-4-(4-fluorophenoxy)phenyl)-3-chlorobenzamide; and
1-(3-bromo-4-(4-fluorophenoxy)phenyl)-3-(3-chlorophenyl)urea.

* * * * *